US011827720B2

(12) United States Patent
Ruker et al.

(10) Patent No.: US 11,827,720 B2
(45) Date of Patent: *Nov. 28, 2023

(54) MULTIVALENT IMMUNOGLOBULINS

(71) Applicant: F-star Therapeutics Limited, Cambridge (GB)

(72) Inventors: Florian Ruker, Vienna (AT); Gottfried Himmler, Gross-Enzersdorf (AT); Gordana Wozniak-Knopp, Vienna (AT)

(73) Assignee: F-star Therapeutics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/677,667

(22) Filed: Aug. 15, 2017

(65) Prior Publication Data
US 2018/0051095 A1  Feb. 22, 2018

Related U.S. Application Data

(63) Continuation of application No. 12/307,578, filed as application No. PCT/AT2007/000313 on Jun. 26, 2007, now abandoned.

(30) Foreign Application Priority Data

Jul. 5, 2006  (AT) .................. A 1147/2006

(51) Int. Cl.
*C07K 16/00* (2006.01)
*C07K 16/46* (2006.01)
*C07K 16/28* (2006.01)

(52) U.S. Cl.
CPC .......... *C07K 16/468* (2013.01); *C07K 16/005* (2013.01); *C07K 16/28* (2013.01); *C07K 16/2887* (2013.01); *C07K 2317/52* (2013.01)

(58) Field of Classification Search
CPC .................................................. C07K 2317/52
See application file for complete search history.

(56) References Cited

U.S. PATENT DOCUMENTS

| | | | |
|---|---|---|---|
| 5,223,409 A | 6/1993 | Ladner et al. |
| 5,395,750 A | 3/1995 | Dillon et al. |
| 5,475,100 A | 12/1995 | Hashino et al. |
| 5,536,814 A | 7/1996 | Ruoslahti et al. |
| 5,723,323 A | 3/1998 | Kauffman et al. |
| 5,759,817 A | 6/1998 | Barbas et al. |
| 5,763,192 A | 6/1998 | Kauffman et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,844,094 A | 12/1998 | Hudson et al. |
| 5,892,019 A | 4/1999 | Schlom et al. |
| 6,057,098 A | 5/2000 | Buechler et al. |
| 6,180,104 B1 | 1/2001 | Davis et al. |
| 6,294,654 B1 | 9/2001 | Bogen et al. |
| 6,352,842 B1 | 3/2002 | Short et al. |
| 6,358,709 B1 | 3/2002 | Short et al. |
| 6,361,974 B1 | 3/2002 | Short et al. |
| 6,365,377 B1 | 4/2002 | Patten et al. |
| 6,376,246 B1 | 4/2002 | Crameri et al. |
| 6,562,617 B1 | 5/2003 | Anderson et al. |
| 6,602,684 B1 | 8/2003 | Umaña et al. |
| 7,442,778 B2 | 10/2008 | Gegg et al. |
| 7,632,497 B2 | 12/2009 | Stavenhagen |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,750,127 B2 | 7/2010 | Gegg et al. |
| 7,750,128 B2 | 7/2010 | Gegg et al. |
| 7,858,090 B2 | 12/2010 | Koide |
| 8,008,453 B2 | 8/2011 | Gegg et al. |
| 8,580,927 B2 | 11/2013 | Dimitrov |
| 8,921,279 B2 | 12/2014 | Himmler et al. |
| 9,045,528 B2 | 6/2015 | Ruker et al. |
| 9,255,149 B2 | 2/2016 | Himmler et al. |
| 2002/0103345 A1 | 8/2002 | Zhu |
| 2002/0106370 A1 | 8/2002 | Cardy et al. |
| 2003/0027213 A1 | 2/2003 | Zhu et al. |
| 2003/0129188 A1 | 7/2003 | Barbas et al. |

(Continued)

FOREIGN PATENT DOCUMENTS

AU  2005/289685  9/2005
AU  2006/204459  1/2006
(Continued)

OTHER PUBLICATIONS

Ngo et al., in The Protein Folding Problem and Tertiary Structure Prediction, Merz, et al., (ed.), Birkhauser, Boston, MA, pp. 433 and 492-495. (Year: 1994).*
Burgess et al., J of Cell Bio. 111:2129-2138. (Year: 1990).*
Lazar et al. Molecular and Cellular Bioloav. 8:1247-1252. (Year: 1988).*
Ying et al. J. Biol. Chem., 287(23):19399-19408. (Year: 2012).*
National Science Foundation Award Abstract # 1262435. (Year: 2012).*
Bowie et al. Science, 247:1306-1310. (Year: 1990).*

(Continued)

*Primary Examiner* — Hong Sang
(74) *Attorney, Agent, or Firm* — Nutter McClennen & Fish LLP

(57) ABSTRACT

The present invention provides a multivalent immunoglobulin or part thereof binding specifically to at least two cell surface molecules of a single cell with at least one modification in at least one structural loop region of the immunoglobulin determining binding to an epitope of the cell surface molecules wherein the unmodified immunoglobulin does not significantly bind to the epitope, its use and methods for producing it.

5 Claims, No Drawings

Specification includes a Sequence Listing.

(56) References Cited

U.S. PATENT DOCUMENTS

| | | | |
|---|---|---|---|
| 2003/0148372 | A1 | 8/2003 | Tomlinson et al. |
| 2003/0157091 | A1 | 8/2003 | Hoogenboom |
| 2004/0018508 | A1 | 1/2004 | Friedman |
| 2004/0043424 | A1 | 3/2004 | Baughn et al. |
| 2004/0063924 | A1 | 4/2004 | Tang et al. |
| 2004/0071690 | A1 | 4/2004 | Hudson et al. |
| 2004/0082508 | A1 | 4/2004 | Yue et al. |
| 2004/0097711 | A1 | 5/2004 | Yue et al. |
| 2004/0101905 | A1 | 5/2004 | Brekke et al. |
| 2004/0132101 | A1 | 7/2004 | Lazar et al. |
| 2004/0146976 | A1 | 7/2004 | Wittrup et al. |
| 2005/0009025 | A1 | 1/2005 | Jakobsen et al. |
| 2005/0054832 | A1 | 3/2005 | Lazar et al. |
| 2005/0069549 | A1 | 3/2005 | Herman |
| 2005/0158829 | A1 | 7/2005 | Fandl et al. |
| 2005/0244403 | A1 | 11/2005 | Lazar et al. |
| 2005/0255548 | A1 | 11/2005 | Lipovsek et al. |
| 2005/0266000 | A1 | 12/2005 | Bond et al. |
| 2006/0140934 | A1 | 6/2006 | Gegg et al. |
| 2008/0227958 | A1* | 9/2008 | Thompson ............. C07K 16/00 530/387.3 |
| 2009/0298195 | A1 | 12/2009 | Ruker et al. |
| 2010/0048877 | A1 | 2/2010 | Ruker et al. |
| 2011/0046355 | A1 | 2/2011 | Himmler et al. |
| 2011/0251375 | A1 | 10/2011 | Rüker et al. |
| 2012/0010388 | A1 | 1/2012 | Himmler |
| 2012/0028839 | A1 | 2/2012 | Rüker et al. |
| 2012/0094874 | A1 | 4/2012 | Rüker et al. |
| 2012/0276104 | A1 | 11/2012 | Woisetschlager |
| 2014/0087957 | A1 | 3/2014 | Vuskovic et al. |
| 2015/0153359 | A1 | 6/2015 | Himmler et al. |

FOREIGN PATENT DOCUMENTS

| | | |
|---|---|---|
| CN | 1606566 | 4/2005 |
| EP | 1 752 471 | 2/2007 |
| EP | 1 772 465 | 4/2007 |
| EP | 2 028 193 | 2/2009 |
| EP | 1 699 826 | 3/2009 |
| EP | 2 407 487 | 1/2012 |
| JP | 2002-058479 | 2/2002 |
| JP | 2003-518377 | 6/2003 |
| JP | 2015-28078 | 2/2015 |
| WO | WO 90/07861 | 7/1990 |
| WO | WO 92/09690 | 6/1992 |
| WO | WO 93/08278 | 4/1993 |
| WO | WO 93/23537 | 11/1993 |
| WO | WO 96/22377 | 7/1996 |
| WO | WO 97/20858 | 6/1997 |
| WO | WO 97/34631 | 9/1997 |
| WO | WO 98/39482 | 9/1998 |
| WO | WO 00/42561 | 7/2000 |
| WO | WO 00/71694 | 11/2000 |
| WO | WO 01/01748 | 1/2001 |
| WO | WO 01/48145 | 7/2001 |
| WO | WO 01/55366 | 8/2001 |
| WO | WO 01/57211 | 8/2001 |
| WO | WO 01/62908 | 8/2001 |
| WO | WO 01/70947 | 9/2001 |
| WO | WO 01/83525 | 11/2001 |
| WO | WO 01/88159 | 11/2001 |
| WO | WO 02/06469 | 1/2002 |
| WO | WO 02/32925 | 4/2002 |
| WO | WO 02/44215 | 6/2002 |
| WO | WO 02/059263 | 8/2002 |
| WO | WO 02/060919 | 8/2002 |
| WO | WO 02/066636 | 8/2002 |
| WO | WO 02/088171 | 11/2002 |
| WO | WO 03/012100 | 2/2003 |
| WO | WO 03/029456 | 4/2003 |
| WO | WO 03/075840 | 9/2003 |
| WO | WO 2004/018674 | 3/2004 |
| WO | WO 2004/033685 | 4/2004 |
| WO | WO 2004/041862 | 5/2004 |
| WO | WO 2004/044004 | 5/2004 |
| WO | WO 2004/044011 | 5/2004 |
| WO | WO 2004/050705 | 6/2004 |
| WO | WO 2004/074322 | 9/2004 |
| WO | WO 2005/021595 | 3/2005 |
| WO | WO 2005/113595 | 12/2005 |
| WO | WO 2005/114215 | 12/2005 |
| WO | WO 2005/116646 | 12/2005 |
| WO | WO 2006/033700 | 3/2006 |
| WO | 2006/036834 | 4/2006 |
| WO | WO 2006/037960 | 4/2006 |
| WO | WO-2006036834 A2 * | 4/2006 ............. C07K 16/00 |
| WO | WO 2006/054096 | 5/2006 |
| WO | WO 2006/056733 | 6/2006 |
| WO | 2006/072620 | 7/2006 |
| WO | WO-2006072620 A1 * | 7/2006 ............. C07K 16/00 |
| WO | WO 2006/087637 | 8/2006 |
| WO | WO 2008/003103 | 1/2008 |
| WO | WO 2008/003116 | 1/2008 |
| WO | WO 2008/119096 | 10/2008 |
| WO | WO 2009/000006 | 12/2008 |
| WO | WO 2009/099961 | 8/2009 |
| WO | WO 2009/132876 | 11/2009 |
| WO | WO 2011/003811 | 1/2011 |
| WO | WO 2012/007167 | 1/2012 |
| WO | WO 2015/049537 | 4/2015 |

OTHER PUBLICATIONS

Sudarsanam, Proteins: Structure, Function, and Genetics, 1998, 30:228-231.*

Bowie J.U., et al., "Deciphering the Message in Protein Sequences: Tolerance to Amino Acid Substitutions," *Science*, vol. 247, Issue No. 4948, pp. 1306-1310 (Mar. 1990).

Burgess W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology*, vol. III, pp. 2129-2138 (Nov. 1990).

Haurum J., Poster: "How to Leverage Oncogene Addiction: Targeted Biological Therapy Inducing Growth Factor Receptor Internalization and Degradation," PEPtalk: The Protein Science Week, 1 page, Jan. 19, 2015.

Lazar E., et al., "Transforming Growth Factor α: Mutation of Aspartic Acid 47 and Leucine 48 Results in Different Biological Activities," *Molecular and Cellular Biology*, pp. 1247-1252 (Mar. 1988).

Mrhalova M., et al., "Relative Quantification of ERBB2 mRNA in Invasive Duct Carcinoma of the Breast: Correlation with ERBB-2 Protein Expression and ERBB2 Gene Copy Number," *Pathology Research and Practice*, vol. 199, pp. 453-461 (2003).

National Science Foundation, "ABI Innovation: Predicting the combined impact of multiple mutations on protein functional adaptation," Award Abstract #1262435, 2 pages (2012).

Ngo, J.T., et al., "Computational Complexity, Protein Structure Prediction, and the Levinthal Paradox," Chapter 14, excerpts from *The Protein Folding Problem and Tertiary Structure Prediction* (including cover and title pages), pp. 491-495 (1994).

Rüker F., "Modular Antibody Technology", F-Star Fact Sheet, 2 pages (Feb. 2008) Retrieved online: [www.boku.ac.at/fileadmin/BOKU-Topstories/20080702_Rueker_Factsheet.pdf] [English Translation].

Wolff A.C., et al., "American Society of Clinical Oncology/College of American Pathologists Guideline Recommendations for Human Epidermal Growth Factor Receptor 2 Testing in Breast Cancer," *Journal of Clinical Oncology*, vol. 25(1), pp. 118-145 (Jan. 2007).

Ying, T., et al., "Soluble Monomeric IgG1 Fc," *The Journal of Biological Chemistry*, vol. 287, Issue No. 3, pp. 19399-19408 (Jun. 2003).

Japanese Patent Office, Office Action (Notice of Reasons for Rejection)—Application No. 2013-246485, 2 pages (dated Mar. 3, 2015 ) [English Translation].

U.S. Appl. No. 12/307,569, filed Jul. 5, 2007 (now U.S. Pat. No. 9,133,274, issued on Sep. 15, 2015).

(56) References Cited

OTHER PUBLICATIONS

U.S. Appl. No. 12/666,618, filed Dec. 23, 2009 (now U.S. Pat. No. 8,921,279, issued on Dec. 30, 2014).
U.S. Appl. No. 12/990,119, filed Oct. 28, 2010 (now U.S. Pat. No. 8,859,738, issued on Oct. 14, 2014).
U.S. Appl. No. 13/086,897, filed Apr. 14, 2011.
U.S. Appl. No. 13/149,871, filed May 31, 2011 (now U.S. Pat. No. 9,856,311 issued on Jan. 2, 2018).
U.S. Appl. No. 13/151,195, filed Jun. 1, 2011 (now U.S. Pat. No. 9,045,528, issued on Jun. 2, 2015).
U.S. Appl. No. 13/228,559, filed Sep. 9, 2011.
U.S. Appl. No. 14/470,425, filed Aug. 27, 2014.
U.S. Appl. No. 14/556,662, filed Dec. 1, 2014 (now U.S. Pat. No. 9,651,559, issued on May 16, 2017).
U.S. Appl. No. 14/629,760, filed Feb. 24, 2015 (now U.S. Pat. No. 9,255,149, issued on Feb. 9, 2016).
U.S. Appl. No. 15/004,692, filed Jan. 22, 2016.
U.S. Appl. No. 15/087,272, filed Mar. 31, 2016.
U.S. Appl. No. 15/284,471, filed Oct. 3, 2016.
U.S. Appl. No. 15/476,029, filed Mar. 31, 2017.
U.S. Appl. No. 15/596,596, filed May 16, 2017.
U.S. Appl. No. 15/676,737, filed Aug. 14, 2017.
Adachi M., et al., "Interaction between the antigen and antibody is controlled by the constant domains: Normal mode dynamics of the HEL-HyHEL-10 complex," *Protein Science*, Vol., Issue No. 10, pp. 2125-2131 (Oct. 2003).
Adib-Conquy M. et al., "Effect of amino acid substitutions in the heavy chain CDR3 of an autoantibody on its reactivity," *International Immunology*, vol. 10, Issue No. 3, pp. 341-346 (Mar. 1998).
Altschul S.F., et al, "Local Alignment Statistics," *Methods in Enzymology*, vol. 266, pp. 460-480 (1996).
Amstutz P., et al., "In vitro display technologies: novel developments and applications," *Current Opinion Biotechnology*, vol. 12, Issue No. 4, pp. 400-405 (Aug. 2001).
Ghahroudi Arabi M., et al., "Selection and identification of single domain antibody fragments from camel heavy-chain antibodies," *FEBS Letters*, vol. 414, Issue No. 3, pp. 521-526 (Sep. 1997).
Asano R., et al., "Humanization of the Bispecific Epidermal Growth Factor Receptor × CD3 Diabody and Its Efficacy as a Potential Clinical Reagent," *Clinical Cancer Research*, vol. 12, No. 13, pp. 4036-4042 (2006).
Auf der Maur A., et al., "Antigen-independent selection of intracellular stable antibody frameworks," *Methods*, vol. 34, No. 2, pp. 215-224 (Oct. 2004).
Barbas II., C.F. et al., "Semisynthetic combinatorial antibody libraries: a chemical solution to the diversity problem," *Proceedings of the National Academy of Sciences of the USA*, vol. 89, No. 10, pp. 4457-4461 (May 15, 1992).
Barclay A.N., "Membrane proteins with immunoglobulin-like domains—a master superfamily of interaction molecules," *Seminars in Immunology*, vol. 15, No. 4, pp. 215-223 (Aug. 2003).
Batey S., et al., "Abstract B123: Preclinical evaluation of FS102: A HER2-specific Fcab with a novel mechanism of action," *Molecular Cancer Therapeutics*, vol. 12, 1 page (Nov. 12, 2013) (Abstract).
Batey S., et al., Poster: "Preclinical evaluation of FS102: A HER2-specific Fcab with a novel mechanism of action," AACR-NCI-EORTC International Conference on Molecular Targets and Cancer Therapeutics, Boston, 1 page (Oct. 21, 2013).
Benhar I., et al., "Highly Efficient Selection of Phage Antibodies Mediated by Display of Antigen as Lpp-OmpA' Fusions on Live Bacteria," *Journal of Molecular Biology*, vol. 301, Issue No. 4, pp. 893-904 (Aug. 2000).
Berntzen G., et al., "Characterization of an FcγRI-binding peptide selected by phage display," *Protein Engineering, Design & Selection*, vol. 19, Issue No. 3, pp. 121-128 (Jan. 2006).
Berntzen G., et al., "Prolonged and increased expression of soluble Fc receptors, IgG and a TCR-Ig fusion protein by transiently transfected adherent 293E cells," *Journal Immunological Methods*, vol. 298, Issue Nos. 1-2, pp. 93-104 (March 2005).

Berry J.D., et al., "Development of Functional Human Monoclonal Single-Chain Variable Fragment Antibody Against HIV-1 from Human Cervical B Cells," *Hybridoma and Hybridomaics*, vol. 22, Issue No. 2, pp. 97-108 (Apr. 2003).
Binz H.K., et al., "High-affinity binders selected from designed ankyrin repeat protein libraries," *Nature Biotechnology*, vol. 22, Issue No. 5, pp. 575-582 (May 2004).
Binz H.K., et al., "Engineering novel binding proteins from nonimmunoglobulin domains," *Nature Biotechnology*, vol. 23, Issue No. 10, pp. 1257-1268 (Oct. 2005).
Bird R.E., et al., "Single-Chain Antigen-Binding Proteins," *Science*, vol. 242, Issue No. 4877, pp. 423-426 (Oct. 1988).
Boder E.T., et al., "Yeast surface display for screening combinatorial polypeptide libraries," *Nature Biotechnology*, vol. 15, Issue No. 6, pp. 553-557 (Jun. 1997).
Boder E.T., et al., "Yeast Surface Display for Directed Evolution of Protein Expression, Affinity, and Stability," *Methods in Enzymology*, vol. 328, pp. 430-444 (2000).
Boder E.T., et al., "Directed evolution of antibody fragments with monovalent femtomolar antigen-binding affinity," *Proceedings of the National Academy of Sciences of the USA*, vol. 97, Issue No. 20, pp. 10701-10705 (Sep. 2000).
Bork P., et al., "The Immunoglobulin Fold. Structural Classification, Sequence Patterns and Common Core," *Journal of Molecular Biology*, vol. 242, pp. 309-320 (1994).
Boulter J.M., et al., "Stable, soluble, high-affinity, engineered T cell receptors: novel antibody-like proteins for specific targeting of Peptide antigens," *Clinical and Experimental Immunology*, pp. 454-460 (2005).
Braren I., et al., "Comparative expression of different antibody formats in mammalian cells and *Pichia pastoris*," *Biotechnology and Applied Biochemistry*, vol. 47, Part 4, pp. 205-214 (Aug. 2007).
Brawley J.V., et al., "Complementarity-Determining Region 1 Sequence Requirements Drive Limited Vα Usage in Response to Influenza Hemagglutinin 307-319 Peptide" *The Journal of Immunology*, vol. 168, Issue No. 8, pp. 3894-3901 (Apr. 2002).
Brekke O.H., et al., "Therapeutic Antibodies for Human Diseases at the Dawn of the Twenty-First Century," *Nature Reviews Drug Discovery*, vol. 2, Issue No. 1, pp. 52-62 (Jan. 2003).
Bunn P.A., Jr., et al., "Expression of Her-2/neu in Human Lung Cancer Cell Lines by Immunohistochemistry and Fluorescence in Situ Hybridization and its Relationship to in Vitro Cytotoxicity by Trastuzumab and Chemotherapeutic Agents," *Clinical Cancer Research*, vol. 7, pp. 3239-3250 (Oct. 2001).
Cabilly S., et al., "Generation of antibody activity from immunoglobulin polypeptide chains produced in *Escherichia coli*," *Proceedings of National Academy of Sciences of the USA*, vol. 81, pp. 3273-3277 (Jun. 1984).
Caldas C., et al., "Humanization of the anti-CD18 antibody 6.7: an unexpected effect of a framework residue in binding to antigen," *Molecular Immunology*, vol. 39, Issue No. 15, pp. 941-952 (May 2003).
Calman A.F., et al., "Expression of T Cell Receptor Genes in Human B Cells", *The Journal of Experimental Medicine*, vol. 164, Issue No. 6, pp. 1940-1957 (Dec. 1986).
Carter P., "Bispecific human IgG by design," *Journal of Immunological Methods*, vol. 248, pp. 7-15 (Feb. 2001).
Carter P., et al., "High Level *Escherichia coli* Expression and Production of A Bivalent Humanized Antibody Fragment," *Biotechnology*, vol. 10, Issue No. 2, pp. 163-167 (Feb. 1992).
Chen G., et al., "Isolation of high-affinity ligand-binding proteins by periplasmic expression with cytometric screen (PECS)," *Nature Biotechnology*, vol. 19, pp. 537-542 (Jun. 2001).
Chien N.C., et al., "Significant structural and functional change of an antigen-binding site by a distant amino acid substitution: Proposal of a structural mechanism," *Proceeding of the National Academy of Sciences of the USA*, vol. 86, Issue No. 14, pp. 5532-5536 (Jul. 1989).
Chirino A.J., et al., "Minimizing the immunogenicity of protein therapeutics," *Drug Discovery Today*, vol. 9, Issue No. 2, pp. 82-90 (Jan. 2004).

(56) References Cited

OTHER PUBLICATIONS

Chlewicki L.K., et al., "High-affinity, Peptide-specific T Cell Receptors can be Generated by Mutations in CDR1, CDR2 or CDR3," *Journal of Molecular Biology*, vol. 346, Issue No. 1, pp. 223-239 (Feb. 2005).

Cho H.S., et al., "Structure of the extracellular region of HER2 alone and in complex with the Herceptin Fab," *Nature*, vol. 421, pp. 756-760 (Feb. 2003).

Coco W.M., et al., "DNA shuffling method for generating highly recombined genes and evolved enzymes," *Nature Biotechology*, vol. 19, pp. 354-359 (Apr. 2001).

Conrath K., et al., "Antigen Binding and Solubility Effects upon the Veneering of a Camel VHH in Framework-2 to Mimic a VH", *Journal of Molecular Biology*, vol. 350, pp. 112-125 (2005).

Cornish-Bowden A., "Nomenclature for incompletely specified bases in nucleic acid sequences: recommendations 1984," *Nucleic Acids Research*, vol. 3, Issue No. 9, pp. 3021-3030 (May 10, 1985).

Cortez-Retamozo V., et al., "Efficient Tumor Targeting By Single-Domain Antibody Fragments of Camels", *International Journal of Cancer*, vol. 98, pp. 456-462 (2002).

Crameri A., et al., "DNA shuffling of a family of genes from diverse species accelerates directed evolution," *Nature*, vol. 391, pp. 288-291 (Jan. 1998).

Dall'Acqua W.F., et al., "Modulation of the Effector Functions of a Human IgG1 through Engineering of Its Hinge Region," *The Journal of Immunology*, vol. 177, pp. 1129-1138 (2006).

Dall'Acqua W.F., et al., "Increasing the Affinity of a Human IgG1 for the Neonatal Fc Receptor: Biological Consequences," *The Journal of Immunology*, vol. 169, pp. 5171-5180 (2002).

De Jager et al., "Simultaneous Detection of 15 Human Cytokines in a Single Sample of Stimulated Peripheral Blood Mononuclear Cells," *Clinical Diagnostic Laboratory Immunology*, vol. 10, Issue No. 1, pp. 133-139 (2003).

DiGiusto D.L., "An Analysis of Sequence Variation in the β Chain Framework and Complementarity Determining Regions of an Allo-Reactive T Cell Receptor," *Molecular Immunology*, vol. 31, Issue No. 9, pp. 693-699 (Jan. 1994).

Doi N., et al., "Screening of conformationally constrained random polypeptide libraries displayed on a protein scaffold," *Cellular and Molecular Life Sciences*, vol. 54, Issue No. 5, pp. 394-404 (May 1998).

Dottorini T., et al., "Crystal Structure of a Human VH: Requirements for Maintaining a Monomeric Fragment," *Biochemistry*, vol. 43, Issue No. 3, pp. 622-628 (Jan. 2004).

Dunn S.M., et al., "Directed evolution of human T cell receptor CDR2 residues by phage display dramatically enhances affinity for cognate peptide-MHC without increasing apparent cross-reactivity," *Protein Science*, vol. 15, pp. 710-721 (2006).

Esteva F.J., et al., "Molecular predictors of response to trastuzumab and lapatinib in breast cancer," *Nature Reviews Clinical Oncology*, vol. 7, Issue No. 2, pp. 98-107 (Feb. 2010).

Ewert S., et al., "Stability improvement of antibodies for extracellular and intracellular applications: CDR grafting to stable frameworks and structure-based framework engineering," *Methods*, vol. 34, pp. 184-199 (2004).

F-star, "F-star Alpha: A new asset centric company," 15 pages (Feb. 11, 2014).

Felgenhauer M., et al., "Nucleotide sequences of the cDNAs encoding the V-regions of H- and L-chains of a human monoclonal antibody specific to HIV-1—gp41," *Nucleic Acids Research*, vol. 18, Issue No. 16, p. 4927 (1990).

Fellouse F.A., et al., "Synthetic antibodies from a four-amino-acid code: A dominant role for tyrosine in antigen recognition," *Proceeding of the National Academy of Sciences of the USA*, vol. 101, Issue No. 34, pp. 12467-12472 (Aug. 2004).

Fellouse F.A., et al., "Molecular Recognition by a Binary Code," *The Journal of Molecular Biology*, vol. 348, Issue No. 5, pp. 1153-1162 (May 2005).

Fellouse F.A., et al., "Tyrosine Plays a Dominant Functional Role in the Paratope of a Synthetic Antibody Derived from a Four Amino Acid Code," *The Journal of Molecular Biology*, vol. 357, pp. 100-114 (2006).

Fields S., et al., "A novel genetic system to detect proteinprotein interactions," *Nature*, vol. 340, pp. 245-246 (Jul. 1989).

Fitzgerald K., "In vitro display technologies—new tools for drug discovery," *Drug Discovery Today*, vol. 5, Issue No. 6, pp. 253-258 (Jun. 2000).

Foote J., et al., "Antibody Framework Residues Affecting the Conformation of the Hypervariable Loops," *Journal of Molecular Biology*, vol. 224, Issue No. 2, pp. 487-499 (Mar. 1992).

Fountzilas G., et al., "A randomized phase III study comparing three anthracycline-free taxane-based regimens, as first line chemotherapy, in metastatic breast cancer," *Breast Cancer Research and Treatment*, vol. 115, pp. 87-99 (2009).

Gao C., et al., "Making artificial antibodies: A format for phage display of combinatorial heterodimeric arrays," *Proceedings of the National Academy of Sciences of the USA*, vol. 96, Issue No. 11 pp. 6025-6030 (May 1999).

Gonçalves M.S.T., "Fluorescent Labeling of Biomolecules with Organic Probes," *Chemical Review*, vol. 109, Issue No. 1, pp. 190-212 (2009).

Georgiou G., et al., "Practical applications of engineering Gram-negative bacterial cell surfaces," *Trends in Biotechnology*, vol. 11, Issue No. 1, pp. 6-10 (Jan. 1993).

Georgiou G., et al., "Display of heterologous proteins on the surface of microorganisms: From the screening of combinatorial libraries to live recombinant vaccines," *Nature Biotechnology*, vol. 15, Issue No. 1, pp. 29-34 (Jan. 1997).

Giusti A.M., et al., "Somatic diversification of S107 from an antiphosphocholine to an anti-DNA autoantibody is due to a single base change in its heavy chain variable region," *Proceedings of the National Academy of Sciences of the USA*, vol. 84, Issue No. 9, pp. 2926-2930 (May 1987).

Gram H., et al., "In vitro selection and affinity maturation of antibodies from a naïve combinatorial immunoglobulin library," *Proceedings of the National Academy of Sciences of the USA*, vol. 89, Issue No. 8, pp. 3576-3580 (Apr. 1992).

Halaby D.M., et al., "The immunoglobulin fold family: sequence analysis and 3D structure comparisons," *Protein Engineering*, vol. 12, Issue No. 7, pp. 563-571 (Jul. 1999).

Hanes J., et al., "In vitro selection and evolution of functional proteins by using ribosome display," *Proceedings of the National Academy of Sciences of the USA*, vol. 94, Issue No. 19, pp. 4937-4942 (May 1997).

Harriman W.D, et al., "Multiplexed Elispot Assay," *Journal Immunology Methods*, vol. 341, Issue No. 1-2, pp. 127-134 (Feb. 2009).

Hasenhindl C., et al., "Stability assessment on a library scale: a rapid method for the evaluation of the commutability and insertion of residues In C-terminal loops of the CH3 domains of IgG1-Fc," *Protein Engineering, Design and Selection*, vol. 26, Issue No. 10, pp. 675-682 (Oct. 2013).

Hasenhindl C., et al., "Creating stable stem regions for loop elongation in Fcabs—Insights from combining yeast surface display, in silico loop reconstruction and molecular dynamics simulations", *Biochimica et Biophysica Acta*, vol. 1844, Issue No. 9, pp. 1530-1540 (Sep. 2014).

Haurum J., "How to Leverage Oncogene Addiction: Targeted Biological Therapy Inducing Growth Factor Receptor Internalization and Degradation," Pipeline 2: Antibody Therapeutics, Inaugural Cancer Targets for Antibody Therapeutics. Discovery, Engineering and Optimization of Next-Generation Oncology Targets, 1 page (Jan. 19-20, 2015).

Hayhurst A., et al., "High-throughput antibody isolation," *Current Opinion in Chemical Biology*, vol. 5, Issue No. 6, pp. 683-689 (Dec. 2001).

He X.M., et al., "Structure of a human monoclonal antibody Fab fragment against gp41 of human immunodeficiency virus type 1," *Proceedings of the National Academy of Science of the USA*, vol. 89, Issue No. 15, pp. 7154-7158 (Aug. 1992).

(56) References Cited

OTHER PUBLICATIONS

Hermeling S., et al., "Structure-Immunogenicity Relationships of Therapeutic Proteins," *Pharmaceutical Research*, vol. 21, Issue No. 6, pp. 897-903 (Jun. 2004).
Holler P.D., et al., "In vitro evolution of a T cell receptor with high affinity for peptide/MHC," *Proceedings of the National Academy of Sciences of the USA*, vol. 97, Issue No. 10, pp. 5387-5392 (May 2000).
Holliger P., et al., "Engineered antibody fragments and the rise of single domains," *Nature Biotechnology*, vol. 23, Issue No. 9, pp. 1126-1136 (Sep. 2005).
Hoogenboom H.R., et al., "Multi-subunit proteins on the surface of filamentous phage: methodologies for displaying antibody (Fab) heavy and light chains," *Nucleic Acids Research*, vol. 19, Issue No. 15, pp. 4133-4137 (Aug. 1991).
Hoogenboom H.R., "Selecting and screening recombinant antibody libraries," *Nature in Biotechnology*, vol. 23, Issue No. 9, pp. 1105-1116 (Sep. 2005).
Hoover D.M., et al., "DNAWorks: an automated method for designing oligonucleotides for PCR-based gene synthesis," *Nucleic Acids Research*, vol. 30, Issue No. 10 (May 2002).
Hosse R.J., et al., "A new generation of protein display scaffolds for molecular recognition," *Protein Science*, vol. 15, Issue No. 1, pp. 14-27 (Jan. 2006).
Hufton S.E., et al., "Development and application of cytotoxic T lymphocyte-associated antigen 4 as a protein scaffold for the generation of novel binding ligand," *FEBS Letters*, vol. 465, Issue No. 3, pp. 225-231 (Jun. 2000).
Huston J.S., et al., "Protein engineering of antibody binding sites: Recovery of specific activity in an anti-digoxin single-chain Fv analogue produced in *Escherichia coli*," *Proceedings of the National Academy of Sciences of the USA*, vol. 85, Issue No. 16, pp. 5879-5883 (Aug. 1988).
Isaac S., et al., Poster: "Pre-clinical evaluation of FS102: A HER2-specific Fcab with a novel mechanism of action," *AstraZeneca-MedImmune-Cambridge Cancer Centre Symposium*, 1 page (Mar. 25, 2014).
Iyengar N.M., et al., "A Pilot Study of Dose-Dense Paclitaxel With Trastuzumab and Lapatinib for Node-negative HER2-Overexpressed Breast Cancer," *Clinical Breast Cancer*, vol. 16, Issue No. 2, pp. 87-94 (Apr. 2016).
Janeway, Jr., C.A., et al., "The domains of an immunoglobulin molecule having similar structures," *Immunobiology, the Immune System in Health and Disease*, 6th edition, 3 pages (2005).
Jez, J., et al.,"Significant Impact of Single N-Glycan Residues on the Biological Activity of Fc-Based Antibody-Like Fragments," *The Journal of Biological Chemistry*, vol. 287, Issue No. 29, pp. 24313-24319 (Jul. 2012).
Johnsson N., et al., "Split ubiquitin as a sensor of protein interactions in vivo," *Proceedings of the National Academy of Sciences of the USA*, vol. 91, Issue No. 22, pp. 10340-10344 (Oct. 1994).
Jones P.T., et al., "Replacing the complementarity-determining regions in a human antibody with those from a mouse," *Nature*, vol. 321, Issue No. 6069, pp. 522-525 (May 1986).
Jung H.C., et al., "Surface display of *Zymomonas mobilis* Levansucrase by using the ice-nucleation protein of *Pseudomonas syringae*," *Nature Biotechnology*, vol. 16, Issue No. 6, pp. 576-580 (Jun. 1998).
Kainer M., et al., "Correlation between CD16a binding and immuno effector functionality of an antigen specific immunoglobulin Fc fragment (Fcab)," *Archives of Biochemistry and Biophysics*, vol. 526, Issue No. 2, pp. 154-158 (Oct. 2012).
Kang A.S., et al., "Linkage of recognition and replication functions by assembling combinatorial antibody Fab libraries along phage surfaces," *Proceedings of the National Academy of Sciences of the USA*, vol. 88, Issue No. 10, pp. 4363-4366 (May 1991).
Kang, X., et al., "Human Neutralizing Fab Molecules against Severe Acute Respiratory Syndrome Coronavirus Generated by Phage Display," *Clinical and Vaccine Immunology*, vol. 13, Issue No. 8, pp. 953-957 (Aug. 2006).

Kashmiri S.V.S., et al., "SDR grafting—a new approach to antibody humanization," *Methods*, vol. 36, Issue No. 1, pp. 25-34 (May 2005).
Kay B.K., et al. (Edtrs.), "Phage Display of Peptides and Proteins: A Laboratory Manual," 10 pages (1996).
Kettleborough C.A., et al., "Humanization of a mouse monoclonal antibody by CDR-grafting: the importance of framework residues on loop conformation," *Protein Engineering*, vol. 4, Issue No. 7, pp. 773-783 (Oct. 1991).
Kieke M.C., et al., "Selection of functional T cell receptor mutants from a yeast surface-display library," *Proceedings of the National Academy of Sciences of the USA*, vol. 96, Issue No. 10, pp. 5651-5656 (May 1999).
Kikuchi M., et al., "Novel family shuffling methods for the in vitro evolution of enzymes," *Gene*, vol. 236, Issue No. 1, pp. 159-167 (Aug. 1999).
Kikuchi M., et al., "An effective family shuffling method using single-stranded DNA," *Gene*, vol. 243, Issue No. 1-2, pp. 133-137 (Feb. 2000).
Kohl J., et al., "Cloning and Expression of an HIV-1 Specific Single-Chain Fv Region Fused to *Escherichia coli* Alkaline Phosphatase," *Annals of the New York Academy of Sciences*, vol. 646, pp. 106-114 (Dec. 1991).
Koide A., et al., "High-affinity single-domain binding proteins with a binary-code interface," *Proceedings of the National Academy of Sciences of the USA*, vol. 104, Issue No. 16, pp. 6632-6637 (Apr. 2007).
Koivunen E., et al., "Selection of Peptides Binding to the $\alpha_5\beta_1$ Integrin from Phage Display Library," The *Journal of Biological Chemistry*, vol. 268, Issue No. 27, pp. 20205-20210 (Sep. 1993).
Kolkman J.A., et al., "Directed evolution of proteins by exon shuffling," *Nature Biotechnology*, vol. 19, pp. 423-428 (May 2001).
König R., "Interactions between MHC molecules and co-receptors of the TCR," *Current Opinion in Immunology*, pp. 75-83 (Mar. 2002).
Kontermann R.E., "Dual targeting strategies with bispecific antibodies," *mAbs*, vol. 4, Issue No. 2, pp. 182-197 (Mar. 2012).
Koren E., et al., "Immune Responses to Therapeutic Proteins in Humans—Clinical Significance, Assessment and Prediction," *Current Pharmaceutical Biotechnology*, vol. 3, pp. 349-360 (2002).
Krebber C., et al., "Selectively-infective Phage (Sip): A Mechanistic Dissection of a Novel in vivo Selection for Protein-ligand Interactions," *Journal of Molecular Biology*, vol. 268, Issue No. 9, pp. 607-618 (May 1997).
Kunkel T.A., "Rapid and efficient site-specific mutagenesis without phenotype selection," *Proceedings of National Academy of Sciences of the USA*, vol. 82, pp. 488-492 (Jan. 1985).
Kufer P., et al., "A revival of bispecific antibodies," *Trends in Biotechnology*, vol. 22, Issue No. 5, pp. 238-244 (May 2004).
Laffly E., et al., "Monoclonal and recombinant antibodies, 30 years after . . . ," *Human Antibiotics*, vol. 14, pp. 33-55 (2005).
Laugel B., et al., "Design of Soluble Recombinant T Cell Receptors for Antigen Targeting and T Cell Inhibition," *The Journal of Biological Chemistry*, vol. 280, Issue No. 3, pp. 1882-1892 (Jan. 2005).
Lauvrak V., et al., "Identification and Characterisation of C1q-Binding Phage Displayed Peptides," *Biology Chemistry*, vol. 378, Issue No. 12, pp. 1509-1519 (Dec. 1997).
Le Gall F., et al., "Effect of linker sequences between the antibody variable domains on the formation, stability and biological activity of a bispecific tandem diabody," *Protein Engineering, Design & Selection*, vol. 17, Issue No. 4, pp. 357-366 (2004).
Lea S., et al., "Analysis of antigenic surfaces of proteins," *The FASEB Journal*, vol. 9, Issue No. 1, pp. 87-93 (Jan. 1995).
Lederman S., et al., "A Single Amino Acid Substitution In a Common African Allele of the CD4 Molecule Ablates Binding of the Monoclonal Antibody, OKT4," *Molecular Immunology*, vol. 28, Issue No. 11, pp. 1171-1181 (Nov. 1991).
Lee J.S., et al., "Surface-displayed viral antigens on *Salmonella* carrier vaccine," *Nature Biotechnology*, vol. 18, Issue No. 6, pp. 645-648 (Jun. 2000).

(56) References Cited

OTHER PUBLICATIONS

Lefranc M.P., et al., "IMGT, the international ImMunoGeneTics database," *Nucleic Acids Research*, vol. 27, Issue No. 1, pp. 209-212 (Jan. 1999).

Lefranc M.P., et al., "IMGT, the international ImMunoGeneTics database," *Nucleic Acids Research*, vol. 29, Issue No. 1, pp. 207-209 (2001).

Lefranc M.P., et al., "IMGT, the international ImMunoGeneTics database," *Nucleic Acids Research*, vol. 31, Issue No. 1, pp. 307-310 (2003).

Lefranc M.P., et al., "IMGT unique numbering for immunoglobulin and T cell receptor constant domains and Ig superfamily C-like domains," *Developmental and Comparative Immunology*, vol. 27, pp. 55-77 (2003).

Lefranc M.P., et al., "IMGT, the international ImMunoGeneTics Information System," *Nucleic Acids Research*, vol. 33, Database issue, pp. D593-D597 (2005).

Lefranc M.P., et al., "IMGT unique numbering for immunoglobulin and T cell receptor constant domains and Ig superfamily C-like domains," *Developmental and Comparative Immunology*, vol. 29, pp. 185-203 (2005).

Leung K.M., et al., "A HER2-specific Modified Fc Fragment (Fcab) Induces Antitumor Effects Through Degradation of HER2 and Apoptosis," *Molecular Therapy*, vol. 23, Issue No. 11, pp. 1722-1733 (Nov. 2015).

Li C.H., et al., "β-Endorphin omission analogs: Dissociation of immunoreactivity from other biological activities," *Proceedings of the National Academy of Sciences of the USA*, vol. 77, Issue No. 6, pp. 3211-3214 (Jun. 1980).

Li Y., et al., "Directed evolution of human T-cell receptors with picomolar affinities by phage display," *Nature Biotechnology*, vol. 23, Issue No. 3, pp. 349-354 (Mar. 2005).

Liang W.C., et al., "Cross-species Vascular Endothelial Growth Factor (VEGF)-blocking Antibodies Completely Inhibit the Growth of Human Tumor Xenografts and Measure the Contribution of Stromal VEGF," *The Journal of Biological Chemistry*, vol. 28, Issue No. 2, pp. 951-961 (Jan. 2006).

Lo Conte L., et al., "The Atomic Structure of Protein-Protein Recognition Sites," *Journal of Molecular Biology*, vol. 285, pp. 2177-2198 (Feb. 1999).

Lowman H.B., et al., "Selecting High-Affinity Binding Proteins by Monovalent Phage Display," *Biochemistry*, vol. 30, pp. 10832-10838 (Nov. 1991).

Lutz S., et al., "Creating multiple-crossover DNA libraries independent of sequence identity," *Proceedings of the National Academy of Sciences of the USA*, vol. 98, Issue No. 20, pp. 11248-11253 (Sep. 2001).

Malmborg A.C., et al., "Selective Phage Infection Mediated by Epitope Expression on F Pilus," *Journal of Molecular Biology*, vol. 273, pp. 544-551 (Oct. 1997).

Marvin J.S., et al., "Recombinant approaches to IgG-like bispecific antibodies," *Acta Pharmacologica Sinica*, vol. 6, pp. 649-658 (Jun. 2005).

Masuda K., et al., "The role of interface framework residues in determining antibody $V_H/V_L$ interaction strength and antigen-binding affinity," *The FEBS Journal*, vol. 273, pp. 2184-2194 (May 2006).

Matiheakis L.C., et al., "An in vitro polysome display system for identifying ligands from very large peptide libraries," *Proceedings of the National Academy of Sciences of the USA*, vol. 91, pp. 9022-9026 (Sep. 1994).

Maynard J., et al., "Antibody Engineering," *Annual Review of Biomedical Engineering*, vol. 2, pp. 339-376 (2000).

McCall A.M., et al., "Increasing the Affinity for Tumor Antigen Enhances Bispecific Antibody Cytotoxicity," *The Journal of Immunology*, vol. 6, pp. 6112-6117 (2001).

McCall A.M., et al., "Isolation and characterization of an anti-CD16 single-chain Fv fragment and construction of an anti-HER2/neu/anti-CD16 bispecific scFv that triggers CD 16-dependent tumor cytolysis," *Molecular Immunology*, vol. 36, pp. 433-446 (1999).

Miyazaki C., et al., "Changes in the specificity of antibodies by site-specific mutagenesis followed by random mutagenesis," *Protein Engineering*, vol. 12, Issue No. 5, pp. 407-415 (1999).

Molloy P.E., et al., "Soluble T cell receptors: novel immunotherapies," *Current Opinion in Pharmacology*, vol. 5, Issue No. 4, pp. 438-443 (Aug. 2005).

Mosquera L.A., et al., "In Vitro and In Vivo Characterization of a Novel Antibody-Like Single-Chain TCR Human IgG1 Fusion Protein," *The Journal of Immunology*, vol. 174, Issue No. 7, pp. 4381-4388 (Apr. 2005).

Moza B., et al., "Long-range cooperative binding effects in a T cell receptor variable domain," *Proceedings of the National Academy of Sciences of the USA*, vol. 103, Issue No. 26, pp. 9867-9872 (Jun. 2006).

Munoz-Olaya J.M., "Advancing Novel Bispecific Antibody Biologies," *Cambridge Healthtech Institute's Inaugural* Phase and Yeast Display of Antibodies, Empowering Novel Biologies, *Seventh Annual PEGS Europe Protein & Antibody Engineering Summit*, 6 pages (Nov. 3-4, 2014).

Nakauchi H., et al., "Molecular cloning of Lyt-2, a membrane glycoprotein marking a subset of mouse T lymphocytes: Molecular homology to its human counterpart, Leu-2/T8, and to immunoglobulin variable regions," *Proceeding of the National Academy of Sciences of the USA*, vol. 82, Issue No. 15, pp. 5126-5130 (Aug. 1985).

Nemoto N., et al., "In vitro virus: Bonding of mRNA bearing puromycin at the 3"-terminal end to the C-terminal end of its encoded protein on the ribosome in vitro," *FEBS Letters*, vol. 414, pp. 405-408 (Sep. 1997).

Nygren P.A., et al., "Scaffold for engineering novel binding sites in proteins," *Current Biology, Engineering and Design*, vol. 7, pp. 463-469 (1997).

Park B.W., et al., "Rationally designed anti-HER2/neu peptide mimetic disables $P185^{HER2/neu}$ tyrosine kinases in vitro and in vivo," *Nature Biotechnology*, vol. 18, pp. 194-198 (Feb. 2000).

Paul W.E. (Edtr.), "Structure and Function of Immunoglobulins", *Fundamental Immunology*, Chapter 9, Third Edition, Raven Press, pp. 292-295 (1993).

Pelletier J.N., et al., "Oligomerization domain-directed reassembly of active dihydrofolate reductase from rationally designed fragments," *Proceedings of the National Academy of Sciences of the USA*, vol. 95, pp. 12141-12146 (Oct. 1998).

Perosa F., et al., "CD20 Mimicry by a mAb Rituximab-Specific Linear Peptide. A Potential Tool for Active Immunotherapy of Autoimmune Diseases," *Annals New York Academy of Sciences*, pp. 672-683 (2005).

Philippidis A., "Companion Diagnostics: 52 Pick-Up," *Genetic Engineering & Biotechnology News, Insight & Intelligence*, 6 pages (May 2013).

Presta L.G., et al., "Engineering therapeutic antibodies for improved function," *Biochemical Society*, vol. 30, Issue No. 4, pp. 487-490 (Mar. 2002).

Privezentzev C.V., Poster: "F-star: Advancing Novel Bispecific Antibody Biologies," *Gordon Research Conference; Antibody Biology & Engineering*, 1 page (Mar. 2014).

Reiter Y., et al., "Construction of a Functional Disulfide-Stabilized TCR Fv Indicates that Antibody and TCR Fv Frameworks Are Very Similar in Structure," *Immunity*, vol. 2, Issue No. 3, pp. 281-287 (Mar. 1995).

Richman S.A., et al., "Development of a novel strategy for engineering high-affinity proteins by yeast display," *Protein Engineering, Design & Selection*, vol. 19, Issue No. 6, pp. 255-264 (2006).

Richman S.A., et al., "Structural features of T cell receptor variable regions that enhance domain stability and enable expression as single-chain VαVβ fragments," *Molecular Immunology*, vol. 46, Issue No. 5, pp. 902-916 (Feb. 2009).

Riechman L., et al., "Single domain antibodies: comparison of camel VH and camelised human VH domains," *Journal of Immunological Methods*, vol. 231, pp. 25-38 (1999).

Roberts R.W., et al., "RNA-peptide fusions for the in vitro selection of peptides and proteins," *Proceedings of the National Academy of Sciences of the USA*, vol. 94, pp. 12297-12302 (Nov. 1997).

(56) References Cited

OTHER PUBLICATIONS

Roitberg A., et al., "Modeling Side Chains in Peptides and Proteins with Locally Enhanced Sampling/Simulated Annealing Method", Chapter 1, *The Protein Folding Problem and Tertiary Structure Prediction*, excerpts from pp. 1-51, Merz K.M., et al. (Edtrs.) (1994).
Rondot S., et al., "A helper phage to improve single-chain antibody presentation in phage display," *Nature Biotechnology*, vol. 19, pp. 75-78 (Jan. 2001).
Roovers R.C., et al., "Efficient inhibition of EGFR signalling and of tumour growth by antagonistic anti-EFGR Nanobodies," *Cancer Immunology, Immunotherapy*, vol. 56, pp. 303-317 (2007).
Rudikoff S., et al., "Single amino acid substitution altering antigen-binding specificity," *Proceedings of the National Academy of Sciences of the USA*, vol. 79, pp. 1979-1983 (Mar. 1982).
Ruiz M., et al., "IMGT, the international ImMunoGeneTics database," *Nucleic Acids Research*, vol. 28, Issue No. 1, pp. 219-221 (2000).
Rüker F., et al., "Expression of a Human Monoclonal Anti-HIV-1 Antibody in CHO Cells," *Annals of New York Academy of Sciences*, vol. 646, pp. 212-219 (Dec. 1991).
Rüker F., "Modular Antibody Technology", F-Star Fact Sheet, 2 pages (Feb. 2008) Retrieved online: [www.boku.ac.at/fileadmin/BOKU-Topstories/20080702_Rueker_Factsheet.pdf].
Salfield J.G., "Isotype selection in antibody engineering," *Nature Biotechnology*, vol. 25, Issue No. 12, pp. 1369-1372 (Dec. 2007).
Saerens D., et al., "Identification of a Universal VHH Framework to Graft Non-canonical Antigen-binding Loops of Camel Single-domain Antibodies," *Journal of Molecular Biology*, vol. 352, pp. 597-607 (2005).
Schaffitzel C., et al., "Ribosome display: an in vitro method for selection and evolution of antibodies from libraries," *Journal of Immunological Methods*, vol. 231, pp. 119-135 (1999).
Schmittel A., et al., "Application of the IFN-γ ELISPOT assay to quantify T cell responses against proteins," *Journal of Immunological Methods*, vol. 247, pp. 17-24 (Jan. 2001).
Shao Z., et al., "Random-priming in vitro recombination: an effective tool for directed evolution," *Nucleic Acids Research*, vol. 26, Issue No. 2, pp. 681-683 (1998).
Shields R.L., et al., "High Resolution Mapping of the Binding Site on Human IgG1 for FcαRI, FcαRII, FcαRIII, and FcRn and Design of IgG1 Variants with Improved Binding to the FcαR," *The Journal of Biological Chemistry*, vol. 276, Issue No. 9, pp. 6591-6604 (Mar. 2001).
Short M.K., et al., "Contribution of Antibody Heavy Chain CDR1 to Digoxin Binding Analyzed by Random Mutagenesis of Phage-displayed Fab 26-10," *The Journal of Biologival Chemistry*, vol. 270, Issue No. 48, pp. 28541-28550 (Dec. 1995).
Shusta E.V., et al., "Directed evolution of a stable scaffold for T-cell receptor engineering," *Nature Biotechnology*, vol. 18, No. 7, pp. 754-759 (Jul. 2000).
Sidhu S.S., et al., "Synthetic therapeutic antibodies," *Nature Chemical Biology*, vol. 2, Issue No. 12, pp. 682-688 (Dec. 2006).
Simon T., et al., "A functional antibody mutant with an insertion in the framework region 3 loop of the $V_H$ domain: implications for antibody engineering," *Protein Engineering*, vol. 5, Issue No. 3, pp. 229-234 (1992).
Skolnick J., et al., "From genes to protein structure and function: novel applications of computational approaches in the genomic era," *Trends in Biotechnology*, vol. 18, pp. 34-39 (Jan. 2000).
Smith G.P., "Filamentous Fusion Phage: Novel Expression Vectors That Display Cloned Antigens on the Virion Surface," *Science*, vol. 228, Issue No. 4705, pp. 1315-1317 (Jun. 1985).
Spiridon C.I., et al., "Targeting Multiple Her-2 Epitopes with Monoclonal Antibodies Results in Improved Antigrowth Activity of a Human Breast Cancer Cell Line in Vitro and in Vivo," *Clinical Cancer Research*, vol. 8, pp. 1720-1730 (Jun. 2002).
Stagg J., et al., "Anti-ErbB-2 mAb therapy requires type I and II interferons and synergizes with anti-PD-1 or anti-CD137 mAb therapy," *Proceedings of the National Academy of Sciences of the USA*, vol. 108, Issue No. 17, pp. 7142-7147 (Apr. 2011).
Tangri S., et al., "Rationally Engineered Therapeutic Proteins with Reduced Immunogenicity," *The Journal of Immunology*, vol. 174, Issue No. 6, pp. 3187-3196 (Mar. 2005).
Tolaney S.M., et al., "Adjuvant Paclitaxel and Trastuzumab for Node-Negative, HER2-Positive Breast Cancer," *The New England Journal of Medicine*, vol. 372, pp. 134-141 (Jan. 2015).
Traxlmayr M.W., et al., "Directed evolution of Her2/neu-binding IgG1-Fc for improved stability And resistance to aggregation by using yeast surface display," *Protein Engineering, Design & Selection*, vol. 26, Issue No. 4, pp. 255-265 (2013).
Traxlmayr M.W., "Construction of pH-Sensitive Her2-binding IgG1-Fc by Directed Evolution," *Biotechnology*, vol. 9, pp. 1013-1022 (2014).
Uhlenbroich S., Poster: "F-star: Advancing Novel Bispecific Antibody Biologies," *Empowered Antibodies Congress*, 1 page (Jun. 18-19, 2014) [Abstract].
Vajdos F.F., et al., "Comprehensive Functional Maps of the Antigen-binding Site of an Anti-ErbB2 Antibody Obtained with Shotgun Scanning Mutagenesis," *Journal of Molecular Biology*, vol. 320, Issue No. 2, pp. 415-428 (Jul. 2002).
Virnekäs B., et al., "Trinucleotide Phosphoramidites: Ideal Reagents For The Synthesis Of Mixed Oligonucleotides For Random Mutagenesis," *Nucleic Acids Research*, vol. 22, Issue No. 25, pp. 5600-5607 (1994).
Visintin M., et al., "Selection of antibodies for intracellular function using a two-hybrid in vivo system," *Proceedings of the National Academy of Sciences of the USA*, vol. 96, Issue No. 21, pp. 11723-11728 (Oct. 1999).
Vogt M., et al., "Construction of an Artificial Receptor Protein ("Anticalin") Based on the Human Apolipoprotein D," *ChemBioChem*, vol. 5, Issue No. 2, pp. 191-199 (Feb. 2004).
Wang W., et al., "Expression Patterns and Transcript Processing of ftt-1 and ftt-2, two *C. elegans* 14-3-3 Homologues," *Journal of Molecular Biology*, vol. 268, pp. 619-630(1997).
Wang L., et al., "Retargeting T Cells for HER2-Positive Tumor Killing by a Bispecific Fv-Fc Antibody," *PLOS One*, vol. 8, Issue No. 9, pp. e75589-1-e75589-11 (Sep. 2013).
Weaver-Feldhaus J.M., et al., "Yeast mating or combinatorial Fab library generation and surface display," *FEBS Letters*, vol. 564, Issue Nos. 1-2, pp. 24-34 (Apr. 2004).
Weber K.S., et al., "Class II-restricted T cell receptor engineered in vitro for higher affinity retains peptide specificity and function," *Proceedings of the National Academy of Sciences of the USA*, vol. 102, Issue No. 52, pp. 19033-19038 (Dec. 2005).
Weiner M.P., et al., "Site-directed mutagenesis of double-stranded DNA by the polymerase chain reaction," *Gene*, vol. 151, Issue No. 1-2, pp. 119-124 (Dec. 1994).
Whitehorn E.A., et al., "A Generic Method for Expression and Use of "Tagged" Soluble Versions of Cell Surface Receptors," *Biotechnology*, vol. 13, Issue No. 11, pp. 1215-1219 (Nov. 1995).
Willcox B.E., et al., "Production of soluble αβ T-cell receptor heterodimers suitable for biophysical analysis of ligand binding," *Protein Science*, vol. 8, Issue No. 11, pp. 2418-2423 (Nov. 1999).
Winter G., et al., "Humanized antibodies," *Immunology Today*, vol. 14, Issue No. 6, pp. 243-246 (1993).
Winkler K., et al., "Changing the Antigen Binding Specificity by Single Point Mutations of an Anti-p24 (HIV-1) Antibody," *The Journal of Immunology*, vol. 165, Issue No. 8, pp. 4505-4514 (Oct. 2000).
Wittrup K.D., "Protein engineering by cell-surface display," *Current Opinion in Biotechnology*, vol. 12, Issue No. 4, pp. 395-399 (Aug. 2001).
Woisetschläger M., et al., "In vivo and in vitro activity of an immunoglobulin Fc fragment (Fcab) with engineered Her-2/neu binding sites," *Biotechnology Journal*, vol. 9, Issue No. 6, pp. 844-851 (Jun. 2014).
Wozniak-Knopp G., et al., "Introducing antigen-binding sites in structural loops of immunoglobulin constant domains: Fc fragments with engineered HER2/neu-binding sites and antibody properties," *Protein Engineering, Design & Selection*, vol. 23, Issue No. 4, pp. 289-297 (Apr. 2010).

(56) References Cited

OTHER PUBLICATIONS

Wu H., et al., "Humanization of a Murine Monoclonal Antibody by Simultaneous Optimization of Framework and CDR Residues," *Journal of Molecular Biology*, vol. 294, Issue No. 1, pp. 151-162 (Nov. 1999).
Wülfing C., et al., "Correctly Folded T-cell Receptor Fragments in the Periplasm of *Escherichia coli*: Influence of Folding Catalysts," *Journal of Molecular Biology*, vol. 242, Issue No. 5, pp. 655-669 (Oct. 1994).
Xiao X., et al., "A large library based on a novel (CH2) scaffold: identification of HIV-1 inhibitors," *Biochemical and Biophysical Research Communications*, vol. 387, Issue No. 2, pp. 387-392 (Sep. 2009).
Yánez J., et al., "Combinatorial condon-based amino acid substitutions," *Nucleic Acids Research*, vol. 32, Issue No. 20, pp. 1-10 (Nov. 2004).
Yau K.Y.F., et al., "Affinity maturation of a VHH by mutational hotspot randomization," *Journal of Immunological Methods*, vol. 297, Issue Nos. 1-2, pp. 213-224 (Feb. 2005).
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, vol. 334, Issue No. 4, pp. 733-749 (Dec. 2003).
Zhou J.M., et al., "A Novel Strategy by the Action of Ricin that Connects Phenotype and Genotype without Loss of the Diversity of Libraries," *Journal of American Chemical Society*, vol. 124, Issue No. 4, pp. 538-543 (Jan. 2002).
Zhao H., et al., "Molecular evolution by staggered extension process (StEP) in vitro recombination," *Nature Biotechnology*, vol. 16, pp. 258-261 (Mar. 1998).
Canadian Intellectual Property Office, Official Action—Application No. 2,721,614, 3 pages (dated Mar. 16, 2015).
Michael Huang Chemical & Biotech Dept. China Patent Agent (H.K.) Ltd., Response to Office Action —Application No. 200780032991.X, 7 pages (filed Oct. 6, 2015).
State Intellectual Property Office of People's Republic of China, Third Office Action—Application No. 200780032857, 4 pages (dated Sep. 23, 2015).
State Intellectual Property Office of People's Republic of China, Third Office Action—Application No. 200780032857, 4 pages (dated Sep. 23, 2015) [English Translation].
Archana Shanker Anand and Anand, Response to First Examination Report—Application No. 4657/DELNP/2007, 8 pages (dated Jan. 17, 2014).
European Patent Office, Communication pursuant to Article 94(3) EPC—Application No. 08 756 842.4, 7 pages (dated Jun. 14, 2010).
European Patent Office—The Hague, Extended European Search Report—Application No. EP 14191631.2-1405, 11 pages (dated Jun. 16, 2015).
European Patent Office, Communication Under Rule 71(3) EPC—Application No. 14 781 645.8-1403, 7 pages (dated Aug. 14, 2017).
European Patent Office, Munich, Extended European Search Report—Application No. EP 17 18 2619, 9 pages (dated Nov. 15, 2017).
Japanese Patent Office, Office Action—Application No. 2013-246485, 2 pages (dated Mar. 3, 2015).
Rebecca Hix, Authorized officer International Searching Authority, International Search Report—International Application No. PCT/AT2007/000313, 3 pages (dated Feb. 29, 2008).
Rebecca Hix, Authorized officer International Searching Authority, Written Opinion of the International Searching Authority, Application No. PCT/AT2007/000313, 9 pages (dated Jan. 5, 2009).
Yolaine Cussac, Authorized officer International Bureau of WIPO, International Preliminary Report on Patentability, International Application PCT/AT2007/000313, 10 pages, together along with the Written Opinion of the International Searching Authority (dated Jan. 6, 2009).
European Patent Office, International Search Report—International Application No. PCT/AT2008/000232, dated Oct. 13, 2008, 4 pages.
Yolaine Cussac, Authorized officer International Bureau of WIPO, International Preliminary Report on Patentability, International Application PCT/AT2008/000232, 10 pages, together along with the Written Opinion of the International Searching Authority (dated Jan. 5, 2010).
Zoran Cilensek, Authorized officer International Searching Authority, International Search Report—Application No. PCT/EP2009/052509, 14 pages, together with the Written Opinion of the International Searching Authority (dated Jun. 3, 2009).
The International Bureau of WIPO, International Preliminary Report on Patentability, Application No. PCT/EP2009/052509, 8 pages (dated Nov. 2, 2010).
Miguel Aguilera, Authorized officer European Patent Officer, International Search Report—Application No. PCT/GB2014/052994, 5 pages (dated Jan. 9, 2015).
International Searching Authority, Written Opinion of International Searching Authority, Application No. PCT/GB2014/052994, 6 pages (dated Jan. 9, 2015).
Athina Nickitas-Etienne, Authorized officer The International Bureau of WIPO, Switzerland, International Preliminary Report on Patability—Application PCT/GB2014/052994, 7 pages, together with the Written Opinion of the International Searching Authority (dated Apr. 5, 2016).
Rebecca Hix, Authorized officer European Patent Office, International Search Report—Application No. PCT/EP2016/057800, 15 pages, together with the Written Opinion of the International Searching Authority (dated Jun. 24, 2016).
Fu Yilong (Dr.), Authorized officer Intellectual Property Office of Singapore, Written Opinion—Application No. 11201602605T, 7 pages (dated Dec. 20, 2016).
U.S. Appl. No. 12/307,578, filed Jun. 26, 2007.
U.S. Appl. No. 12/307,582, filed Jul. 5, 2007.
U.S. Appl. No. 14/853,919, filed Sep. 14, 2015.

* cited by examiner

SEQUENCE LISTING

```
<160> NUMBER OF SEQ ID NOS: 35

<210> SEQ ID NO 1
<211> LENGTH: 324
<212> TYPE: DNA
<213> ORGANISM: Artificial Sequence
<220> FEATURE:
<223> OTHER INFORMATION: Nucleotide Sequence of the first CH3 library
<220> FEATURE:
<221> NAME/KEY: misc_feature
<222> LOCATION: (217)..(218)
<223> OTHER INFORMATION: n is a, c, g, or t
<220> FEATURE:
<221> NAME/KEY: misc_feature
<222> LOCATION: (220)..(221)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (229)..(230)
<223> OTHER INFORMATION: n is a, c, g, or t
<220> FEATURE:
<221> NAME/KEY: misc_feature
<222> LOCATION: (232)..(233)
<223> OTHER INFORMATION: n is a, c, g, or t
<220> FEATURE:
<221> NAME/KEY: misc_feature
<222> LOCATION: (235)..(236)
<223> OTHER INFORMATION: n is a, c, g, or t
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t

<400> SEQUENCE: 1
```

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgcccnnsn nsnhsttgnn snnsnnsnns     240
nnsnnsacct acatctgcaa cgtgaatcac aagcccagca caccaaggt ggacaagaaa     300 gttgagccca aatctgcggc cgca                                           324
```

```
<210> SEQ ID NO 2
<211> LENGTH: 130
<212> TYPE: PRT
<213> ORGANISM: Artificial Sequence
<220> FEATURE:
<223> OTHER INFORMATION: Amino Acid sequence of the first CH1 library
<220> FEATURE:
<221> NAME/KEY: misc_feature
<222> LOCATION: (95)..(97)
<223> OTHER INFORMATION: Xaa can be any naturally occurring amino acid
<220> FEATURE:
<221> NAME/KEY: misc_feature
<222> LOCATION: (99)..(104)
<223> OTHER INFORMATION: Xaa can be any naturally occurring amino acid

<400> SEQUENCE: 2

Met Lys Tyr Leu Leu Pro Thr Ala Ala Ala Gly Leu Leu Leu Leu Ala
1               5                  10                  15

Ala Gln Pro Ala Met Ala Ala Ser Thr Lys Gly Pro Ser Val Phe Pro
            20                  25                  30

Leu Ala Pro Ser Ser Lys Ser Thr Ser Gly Gly Thr Ala Ala Leu Gly
        35                  40                  45

Cys Leu Val Lys Asp Tyr Phe Pro Glu Pro Val Thr Val Ser Trp Asn
    50                  55                  60

Ser Gly Ala Leu Thr Ser Gly Val His Thr Phe Pro Ala Val Leu Gln
65                  70                  75                  80

Ser Ser Gly Leu Tyr Ser Leu Ser Ser Val Val Thr Val Pro Xaa Xaa
                85                  90                  95

Xaa Leu Xaa Xaa Xaa Xaa Xaa Xaa Thr Tyr Ile Cys Asn Val Asn His
            100                 105                 110

Lys Pro Ser Asn Thr Lys Val Asp Lys Lys Val Glu Pro Lys Ser Ala
        115                 120                 125

Ala Ala
    130
```

```
<210> SEQ ID NO 3
<211> LENGTH: 324
<212> TYPE: DNA
<213> ORGANISM: Artificial Sequence
<220> FEATURE:
<223> OTHER INFORMATION: Nucleotide sequence of the second CH1 library
<220> FEATURE:
<221> NAME/KEY: misc_feature
<222> LOCATION: (214)..(215)
<223> OTHER INFORMATION: n is a, c, g, or t
<220> FEATURE:
<221> NAME/KEY: misc_feature
<222> LOCATION: (217)..(218)
<223> OTHER INFORMATION: n is a, c, g, or t
<220> FEATURE:
<221> NAME/KEY: misc_feature
<222> LOCATION: (220)..(221)
<223> OTHER INFORMATION: n is a, c, g, or t
<220> FEATURE:
<221> NAME/KEY: misc_feature
<222> LOCATION: (223)..(224)
```

```
<223> OTHER INFORMATION: n is a, c, g, or t
<220> FEATURE:
<221> NAME/KEY: misc_feature
<222> LOCATION: (226)..(227)
<223> OTHER INFORMATION: n is a, c, g, or t
<220> FEATURE:
<221> NAME/KEY: misc_feature
<222> LOCATION: (229)..(230)
<223> OTHER INFORMATION: n is a, c, g, or t
<220> FEATURE:
<221> NAME/KEY: misc_feature
<222> LOCATION: (232)..(233)
<223> OTHER INFORMATION: n is a, c, g, or t
<220> FEATURE:
<221> NAME/KEY: misc_feature
<222> LOCATION: (235)..(236)
<223> OTHER INFORMATION: n is a, c, g, or t
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (247)..(248)
<223> OTHER INFORMATION: n is a, c, g, or t

<400> SEQUENCE: 3
gcctccacca agggcccatc ggtcttcccc ctggcaccct cctccaagag cacctctggg      60
ggcacagcag ccctgggctg cctggtcaag gactacttcc ccgaaccggt gacggtgtcg     120
tggaactcag gcgccctgac cagcggcgtg cacaccttcc cggctgtcct gcagtcctca     180
ggactctact ccctcagcag cgtggtgacc gtgnnsnnsn nsnnsnnsnn snnsnnsnns     240
nnsnnsnnst acatctgcaa cgtgaatcac aagcccagca acaccaaggt ggacaagaaa     300
gttgagccca aatctgcggc cgct                                            324

<210> SEQ ID NO 4
<211> LENGTH: 108
<212> TYPE: PRT
<213> ORGANISM: Artificial Sequence
<220> FEATURE:
<223> OTHER INFORMATION: Amino acid sequence of the second CH1 library
<220> FEATURE:
<221> NAME/KEY: misc_feature
<222> LOCATION: (72)..(83)
<223> OTHER INFORMATION: Xaa can be any naturally occurring amino acid
      that is substituted or inserted

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Tyr Phe Pro Ala Val Leu Gln Ser Ser Gly Leu Tyr Ser
    50                  55                  60

Leu Ser Ser Val Val Thr Val Xaa Xaa Xaa Xaa Xaa Xaa Xaa Xaa Xaa
65                  70                  75                  80

Xaa Xaa Xaa Tyr Ile Cys Asn Val Asn His Lys Pro Ser Asn Thr Lys
```

```
                    85                  90                  95
Val Asp Lys Lys Val Glu Pro Lys Ser Ala Ala Ala
            100                 105

<210> SEQ ID NO 5
<211> LENGTH: 321
<212> TYPE: DNA
<213> ORGANISM: Artificial Sequence
<220> FEATURE:
<223> OTHER INFORMATION: Nucleotide sequence of the CL library
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (226)..(227)
<223> OTHER INFORMATION: n is a, c, g, or t
<220> FEATURE:
<221> NAME/KEY: misc_feature
<222> LOCATION: (229)..(230)
<223> OTHER INFORMATION: n is a, c, g, or t
<220> FEATURE:
<221> NAME/KEY: misc_feature
<222> LOCATION: (232)..(233)
<223> OTHER INFORMATION: n is a, c, g, or t
<220> FEATURE:
<221> NAME/KEY: misc_feature
<222> LOCATION: (235)..(236)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (247)..(248)
<223> OTHER INFORMATION: n is a, c, g, or t

<400> SEQUENCE: 5
gtggctgcac catctgtctt catcttcccg ccatctgatg agcagttgaa atctnnsnns      60
nnsggaactg cctctgttgt gtgcctgctg aataacttct atcccagaga ggccaaagta     120
cagtggaagg tggataacgc cctccaatcg ggtaactccc aggagagtgt cacagagcag     180
gacagcaagg acagcaccta cagcctcagg tcgaccctga cgctgnnsnn snnsnnstac     240
nnsnnsnnsa aagtctacgc ctgcgaagtc acccatcagg gcctgagctc gcccgtcaca     300
aagagcttca acaggggaga g                                              321

<210> SEQ ID NO 6
<211> LENGTH: 107
<212> TYPE: PRT
<213> ORGANISM: Artificial Sequence
<220> FEATURE:
<223> OTHER INFORMATION: Aminio acid sequence if the CL library
<220> FEATURE:
<221> NAME/KEY: misc_feature
<222> LOCATION: (19)..(21)
<223> OTHER INFORMATION: Xaa can be any naturally occurring amino acid
      that is substituted or inserted
```

```
<220> FEATURE:
<221> NAME/KEY: misc_feature
<222> LOCATION: (76)..(79)
<223> OTHER INFORMATION: Xaa can be any naturally occurring amino acid
      that is substituted or inserted
<220> FEATURE:
<221> NAME/KEY: misc_feature
<222> LOCATION: (81)..(83)
<223> OTHER INFORMATION: Xaa can be any naturally occurring amino acid
      that is substituted or inserted

<400> SEQUENCE: 6

Val Ala Ala Pro Ser Val Phe Ile Phe Pro Pro Ser Asp Glu Gln Leu
1               5                   10                  15

Lys Ser Xaa Xaa Xaa Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Arg Ser Thr Leu Thr Leu Xaa Xaa Xaa Xaa Tyr
65                  70                  75                  80

Xaa Xaa Xaa Lys Val Tyr Ala Cys Glu Val Thr His Gln Gly Leu Ser
            85                  90                  95

Ser Pro Val Thr Lys Ser Phe Asn Arg Gly Glu
        100                 105

<210> SEQ ID NO 7
<211> LENGTH: 12
<212> TYPE: PRT
<213> ORGANISM: Artificial Sequence
<220> FEATURE:
<223> OTHER INFORMATION: synthetic peptide RpIO-L

<400> SEQUENCE: 7

Ile Thr Pro Trp Pro His Trp Leu Glu Arg Ser Ser
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Clone A21 second group

<400> SEQUENCE: 8

Pro Trp Gly Pro Arg Asp
1               5

<210> SEQ ID NO 9
<211> LENGTH: 6
<212> TYPE: PRT
<213> ORGANISM: Artificial Sequence
<220> FEATURE:
<223> OTHER INFORMATION: Clone C50 2nd group

<400> SEQUENCE: 9

Ala Leu Cys Arg Trp Phe
1               5

<210> SEQ ID NO 10
<211> LENGTH: 6
<212> TYPE: PRT
<213> ORGANISM: Artificial Sequence
<220> FEATURE:
```

<223> OTHER INFORMATION: Clone D5 second group

<400> SEQUENCE: 10

Phe Cys Gly Gly Val Val
1               5

<210> SEQ ID NO 11
<211> LENGTH: 6
<212> TYPE: PRT
<213> ORGANISM: Artificial Sequence
<220> FEATURE:
<223> OTHER INFORMATION: Clone D39 second group

<400> SEQUENCE: 11

Gln Gln Lys Pro Phe Ala
1               5

<210> SEQ ID NO 12
<211> LENGTH: 6
<212> TYPE: PRT
<213> ORGANISM: Artificial Sequence
<220> FEATURE:
<223> OTHER INFORMATION: Clone D83, second group

<400> SEQUENCE: 12

Asp Leu Val His Val Ala
1               5

<210> SEQ ID NO 13
<211> LENGTH: 113
<212> TYPE: PRT
<213> ORGANISM: Artificial Sequence
<220> FEATURE:
<223> OTHER INFORMATION: Sequence of CD20 specific CH3+3 Library clone
      D83

<400> SEQUENCE: 13

Met Ala Pro Arg Glu Pro Gln Val Tyr Thr Leu Pro Pro Ser Arg Asp
1               5                   10                  15

Glu Leu Ala Pro Pro Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Leu Val His Val Ala Arg Trp
65                  70                  75                  80

Met Val Gly Asn Val Phe Ser Cys Ser Val Met His Glu Ala Leu His
                85                  90                  95

Asn His Tyr Thr Gln Lys Ser Leu Ser Leu Ser Pro Gly Lys Ala Ala
                100                 105                 110

Ala

<210> SEQ ID NO 14
<211> LENGTH: 324
<212> TYPE: DNA
<213> ORGANISM: Artificial Sequence
<220> FEATURE:
<223> OTHER INFORMATION: Locus C45

<400> SEQUENCE: 14
gcctccacca agggcccatc ggtcttcccc ctggcaccct cctccaagag cacctctggg      60

```
ggcacagcag ccctgggctg cctggtcaag gactacttcc ccgaaccggt gacggtgtcg      120
tggaactcag gcgccctgac cagcggcgtg cacaccttcc cggctgtcct gcagtcctca      180
ggactctact ccctcagcag cgtggtgacc gtggcccctc tgggtgttgg tgggcatctc      240
gtcctgcact acatctgcaa gctgaatcac aagcccagca acaccaaggt ggacaagaaa      300
gttgagccca aatctgcggc cgct                                             324
```

<210> SEQ ID NO 15
<211> LENGTH: 108
<212> TYPE: PRT
<213> ORGANISM: Artificial Sequence
<220> FEATURE:
<223> OTHER INFORMATION: Amino acid sequence C45

<400> SEQUENCE: 15

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Ala Pro Leu Gly Val Gly Gly His Leu
65                  70                  75                  80

Val Leu His Tyr Ile Cys Asn Val Asn His Lys Pro Ser Asn Thr Lys
                85                  90                  95

Val Asp Lys Lys Val Glu Pro Lys Ser Ala Ala Ala
            100                 105
```

<210> SEQ ID NO 16
<211> LENGTH: 290
<212> TYPE: PRT
<213> ORGANISM: Artificial Sequence
<220> FEATURE:
<223> OTHER INFORMATION: Fcab-RG4

<400> SEQUENCE: 16

```
Met Lys Tyr Leu Leu Pro Thr Ala Ala Ala Gly Leu Leu Leu Leu Ala
1               5                   10                  15

Ala Gln Pro Ala Met Ala Met Ala Glu Pro Lys Ser Cys Asp Lys Thr
            20                  25                  30

His Thr Cys Pro Pro Cys Pro Ala Pro Glu Leu Leu Gly Gly Pro Ser
        35                  40                  45

Val Phe Leu Phe Pro Pro Lys Pro Lys Asp Thr Leu Met Ile Ser Arg
    50                  55                  60

Thr Pro Glu Val Thr Cys Val Val Val Asp Val Ser His Glu Asp Pro
65                  70                  75                  80

Glu Val Lys Phe Asn Trp Tyr Val Asp Gly Tyr Glu Val His Asn Ala
                85                  90                  95

Lys Thr Lys Pro Arg Glu Glu Gln Tyr Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Ala Leu Pro Ala Pro Ile Glu Lys Thr
    130                 135                 140

Ile Ser Lys Ala Lys Gly Gln Pro Arg Glu Pro Gln Val Tyr Thr Leu
```

|   |   |   | 145 |   |   |   | 150 |   |   |   | 155 |   |   |   | 160 |
|---|---|---|---|---|---|---|---|---|---|---|---|---|---|---|---|
| Pro | Pro | Ser | Arg | Asp | Glu | Leu | Thr | Lys | Asn | Gln | Val | Ser | Leu | Thr | Cys |
|   |   |   | 165 |   |   |   | 170 |   |   |   | 175 |   |   |   |   |
| Leu | Val | Lys | Gly | Phe | Tyr | Pro | Ser | Asp | Ile | Ala | Val | Glu | Trp | Glu | Ser |
|   |   |   | 180 |   |   |   | 185 |   |   |   | 190 |   |   |   |   |
| Asn | Gly | Gln | Pro | Glu | Asn | Asn | Tyr | Lys | Thr | Thr | Pro | Pro | Val | Leu | Asp |
|   |   |   | 195 |   |   |   | 200 |   |   |   | 205 |   |   |   |   |
| Ser | Asp | Gly | Ser | Phe | Phe | Leu | Tyr | Ser | Lys | Leu | Thr | Val | Gly | Cys | Arg |
|   |   |   | 210 |   |   |   | 215 |   |   |   | 220 |   |   |   |   |
| Gly | Asp | Cys | Leu | Ser | Arg | Trp | Gln | Gln | Gly | Asn | Val | Phe | Ser | Cys | Ser |
| 225 |   |   |   |   | 230 |   |   |   |   | 235 |   |   |   |   | 240 |
| Val | Met | His | Glu | Ala | Leu | His | Asn | His | Tyr | Thr | Gln | Lys | Ser | Leu | Ser |
|   |   |   |   | 245 |   |   |   |   | 250 |   |   |   |   | 255 |   |
| Leu | Ser | Pro | Gly | Lys | Ala | Ala | Ala | Leu | Glu | Ile | Lys | Arg | Ala | Ser | Gln |
|   |   |   | 260 |   |   |   | 265 |   |   |   | 270 |   |   |   |   |
| Pro | Glu | Leu | Ala | Pro | Glu | Asp | Pro | Glu | Asp | Val | Glu | His | His | His | His |
|   |   |   | 275 |   |   |   | 280 |   |   |   | 285 |   |   |   |   |
| His | His |   |   |   |   |   |   |   |   |   |   |   |   |   |   |
| 290 |   |   |   |   |   |   |   |   |   |   |   |   |   |   |   |

<210> SEQ ID NO 17
<211> LENGTH: 869
<212> TYPE: DNA
<213> ORGANISM: Artificial Sequence
<220> FEATURE:
<223> OTHER INFORMATION: Fcab-RGD4 DNA

<400> SEQUENCE: 17

```
atgaaatacc tgctgccgac cgctgctgct ggtctgctgc tcctcgcggc ccagccggcg      60
atggccatgc ccgagcccaa atcttgtgac aaaactcaca catgcccacc gtgcccagca     120
cctgaactcc tggggggacc gtcgtcttcc tcttccccc  aaaacccaag gacacccctca     180
tgatctcccg accctgag    gtcacatgcg tggtggtgga cgtgagccac gaagaccctg    240
aggtcaagtt caactggtac gtggacggcg tggaggtgca taatgccaag acaaagccgc    300
gggaggagca gtacaacagc acgtaccgtg tggtcagcgt cctcaccgtc ctgcaccagg    360
actggctgaa tggcaaggag tacaagtgca aggtctccaa caaagccctc ccagccccca    420
tcgagaaaac catctccaaa gccaaagggc agccccgaga accacaggtg tacaccctgc    480
ccccatcccg ggatgagctg accaagaacc aggtcagcct gacctgcctg gtcaaaggct    540
tctatcccag cgacatcgcc gtggagtggg agagcaatgg gcagccggag aacaactaca    600
agaccacgcc tcccgtgctg gactccgacg gctccttctt cctctacagc aagcttaccg    660
tgggttgccg cggtgattgt ctgagcaggt ggcagcaggg gaacgtcttc tcatgctccg    720
tgatgcatga ggctctgcac aaccactaca cgcagaagag cctctccctg tctccgggta    780
aagcggccgc actcgagatc aaacgggcta gccagccaga actcgccccg gaagaccccg    840
aggatgtcga gcaccaccac caccaccac                                      869
```

<210> SEQ ID NO 18
<211> LENGTH: 869
<212> TYPE: DNA
<213> ORGANISM: Artificial Sequence
<220> FEATURE:
<223> OTHER INFORMATION: complementary DNA strand for fcab-RGD4

<400> SEQUENCE: 18

```
tactttatgg acgacggctg gcgacgacga ccagacgacg aggagcgccg ggtcggccgc    60
taccggtacg ggctcgggtt tagaacactg ttttgagtgt gtacgggtgg cacgggtcgt   120
ggacttgagg accccctgg cagcagaagg agaaggggg ttttgggttc ctgtgggagt    180
actagagggc ctggggactc cagtgtacgc accaccacct gcactcggtg cttctgggac   240
tccagttcaa gttgaccatg cacctgccgc acctccacgt attacggttc tgtttcggcg   300
ccctcctcgt catgttgtcg tgcatggcac accagtcgca ggagtggcag gacgtggtcc   360
tgaccgactt accgttcctc atgttcacgt tccagaggtt gtttcgggag gtcggggggt   420
agctcttttg gtagaggttt cggtttcccg tcggggctct tggtgtccac atgtgggacg   480
ggggtagggc cctactcgac tggttcttgg tccagtcgga ctggacggac cagtttccga   540
agatagggtc gctgtagcgg cacctcaccc tctcgttacc cgtcggcctc ttgttgatgt   600
tctggtgcgg agggcacgac ctgaggctgc cgaggaagaa ggagatgtcg ttcgaatggc   660
acccaacggc gccactaaca gactcgtcca ccgtcgtccc cttgcagaag agtacgaggc   720
actacgtact ccgagacgtg ttggtgatgt gcgtcttctc ggagagggac agaggcccat   780
ttcgccggcg tgagctctag tttgcccgat cggtcggtct tgagcggggc cttctggggc   840
tcctacagct cgtggtggtg gtggtggtg                                      869
```

```
<210> SEQ ID NO 19
<211> LENGTH: 6
<212> TYPE: PRT
<213> ORGANISM: Artificial Sequence
<220> FEATURE:
<223> OTHER INFORMATION: potentially cyclic peptide isolated from
      library by Koivunen

<400> SEQUENCE: 19

Cys Arg Gly Asp Cys Leu
1               5

<210> SEQ ID NO 20
<211> LENGTH: 7
<212> TYPE: PRT
<213> ORGANISM: Artificial Sequence
<220> FEATURE:
<223> OTHER INFORMATION: peptide sequence for insertion into EF loop

<400> SEQUENCE: 20

Gly Cys Arg Gly Asp Cys Leu
1               5

<210> SEQ ID NO 21
<211> LENGTH: 108
<212> TYPE: PRT
<213> ORGANISM: Homo sapiens

<400> SEQUENCE: 21

Pro Arg Glu Pro Gln Val Tyr Thr Leu Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80
```

Phe Ser Cys Ser Val Met His Glu Ala Leu His Asn His Tyr Thr Gln
            85                  90                  95

Lys Ser Leu Ser Leu Ser Pro Gly Lys Ala Ala Ala
            100                 105

<210> SEQ ID NO 22
<211> LENGTH: 332
<212> TYPE: DNA
<213> ORGANISM: Artificial Sequence
<220> FEATURE:
<223> OTHER INFORMATION: synthetic oligonucleotide; engineered CH3
      library
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (225)..(226)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (237)..(238)
<223> OTHER INFORMATION: n is a, c, g, or t

<400> SEQUENCE: 22
ccatggcccc cgagaaccca caggtgtaca ccctgccccc atcccgtgac gagctcnnsn      60
nsnnscaagt cagcctgacc tgcctggtca aaggcttcta tcccagcgac atcgccgtgg    120
agtgggagag caatgggcag ccggagaaca actacaagac cacgcctccc gtgctggact    180
ccgacggctc cttcttcctc tacagcaagc ttaccgtgnn snnsnnsagg tggnnsnnsg    240
ggaacgtctt ctcatgctcc gtgatgcatg aggctctgca caaccactac acacagaaga    300
gcctctccct gtctccgggt aaagcggccg ca                                   332

<210> SEQ ID NO 23
<211> LENGTH: 110
<212> TYPE: PRT
<213> ORGANISM: Artificial Sequence
<220> FEATURE:
<223> OTHER INFORMATION: Synthetic peptide - translation of SEQ ID NO:2
<220> FEATURE:
<221> NAME/KEY: MISC_FEATURE
<222> LOCATION: (19)..(21)
<223> OTHER INFORMATION: Xaa can be any naturally occurring amino acid
<220> FEATURE:
<221> NAME/KEY: MISC_FEATURE
<222> LOCATION: (73)..(75)
<223> OTHER INFORMATION: Xaa can be any naturally occurring amino acid
<220> FEATURE:
<221> NAME/KEY: MISC_FEATURE

```
<222> LOCATION: (78)..(79)
<223> OTHER INFORMATION: Xaa can be any naturally occurring amino acid

<400> SEQUENCE: 23

Met Ala Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Xaa Xaa Xaa Arg Trp Xaa Xaa Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys Ala Ala Ala
            100                 105                 110

<210> SEQ ID NO 24
<211> LENGTH: 33
<212> TYPE: DNA
<213> ORGANISM: Artificial Sequence
<220> FEATURE:
<223> OTHER INFORMATION: Synthetic oligonucleotide primer for assembly
      of SEQ ID NO:22

<400> SEQUENCE: 24
cttgccatgg cccccccgaga accacaggtg tac                              33

<210> SEQ ID NO 25
<211> LENGTH: 30
<212> TYPE: DNA
<213> ORGANISM: Artificial Sequence
<220> FEATURE:
<223> OTHER INFORMATION: Synthetic oligonucleotide primer for generating
      SEQ ID NO:22

<400> SEQUENCE: 25
agtcgagctc gtcacgggat gggggcaggg                                   30

<210> SEQ ID NO 26
<211> LENGTH: 41
<212> TYPE: DNA
<213> ORGANISM: Artificial Sequence
<220> FEATURE:
<223> OTHER INFORMATION: Artificial sequence Primer used to generate SEQ
      ID NO;22
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 26
gtacgagctc nnsnnsnnsc aagtcagcct gacctgcctg g                      41

<210> SEQ ID NO 27
```

```
<211> LENGTH: 32
<212> TYPE: DNA
<213> ORGANISM: Artificial Sequence
<220> FEATURE:
<223> OTHER INFORMATION: Synthetic oligonucleotide Primer used to
      generate SEQ ID NO: 22

<400> SEQUENCE: 27
tgccaagctt gctgtagagg aagaaggagc cg                                   32

<210> SEQ ID NO 28
<211> LENGTH: 59
<212> TYPE: DNA
<213> ORGANISM: Artificial Sequence
<220> FEATURE:
<223> OTHER INFORMATION: Synthetic oligonucleotide used to generate SEQ
      ID NO:22
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 28
tgccaagctt accgtgnnsn nsnnsaggtg gnnsnnsggg aacgtcttct catgctccg      59

<210> SEQ ID NO 29
<211> LENGTH: 33
<212> TYPE: DNA
<213> ORGANISM: Artificial Sequence
<220> FEATURE:
<223> OTHER INFORMATION: Synthetic oligonucleotide Primer used to
      generate SEQ ID NO:22

<400> SEQUENCE: 29
agttgcggcc gctttacccg gagacaggga gag                                  33

<210> SEQ ID NO 30
<211> LENGTH: 113
<212> TYPE: PRT
<213> ORGANISM: Artificial Sequence
<220> FEATURE:
<223> OTHER INFORMATION: Synthetic peptide amino acid sequence of CH3+3
      library construct
<220> FEATURE:
<221> NAME/KEY: MISC_FEATURE
<222> LOCATION: (19)..(21)
<223> OTHER INFORMATION: Xaa can be any naturally occurring amino acid
      that is substituted or inserted
<220> FEATURE:
<221> NAME/KEY: MISC_FEATURE
<222> LOCATION: (73)..(78)
<223> OTHER INFORMATION: Xaa can be any naturally occurring amino acid
      that is substituted or inserted
<220> FEATURE:
<221> NAME/KEY: MISC_FEATURE
<222> LOCATION: (81)..(82)
<223> OTHER INFORMATION: Xaa can be any naturally occurring amino acid
``` that is substituted or inserted

<400> SEQUENCE: 30

Met Ala Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Xaa Xaa Xaa Xaa Xaa Arg Trp
65                  70                  75                  80

Xaa Xaa Gly Asn Val Phe Ser Cys Ser Val Met His Glu Ala Leu His
            85                  90                  95

Asn His Tyr Thr Gln Lys Ser Leu Ser Leu Ser Pro Gly Lys Ala Ala
            100                 105                 110

Ala

<210> SEQ ID NO 31
<211> LENGTH: 341
<212> TYPE: DNA
<213> ORGANISM: Artificial Sequence
<220> FEATURE:
<223> OTHER INFORMATION: Synthetic oligonucleotide nucleotide sequence
      of construct for CH3+3 library
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (225)..(226)
<223> OTHER INFORMATION: n is a, c, g, or t
<220> FEATURE:
<221> NAME/KEY: misc_feature
<222> LOCATION: (228)..(229)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (243)..(244)
<223> OTHER INFORMATION: n is a, c, g, or t
<220> FEATURE:
<221> NAME/KEY: misc_feature
<222> LOCATION: (246)..(247)
<223> OTHER INFORMATION: n is a, c, g, or t

<400> SEQUENCE: 31

```
ccatggcccc cgagaacca caggtgtaca ccctgccccc atcccgtgac gagctcnnsn      60
nsnnscaagt cagcctgacc tgcctggtca aaggcttcta tcccagcgac atcgccgtgg    120
agtgggagag caatgggcag ccggagaaca actacaagac cacgcctccc gtgctggact    180
ccgacggctc cttcttcctc tacagcaagc ttaccgtgnn snnsnnsnns nnsnnsaggt    240
ggnnsnnsgg gaacgtcttc tcatgctccg tgatgcatga ggctctgcac aaccactaca    300
cacagaagag cctctccctg tctccgggta aagcggccgc a                       341
```

<210> SEQ ID NO 32
<211> LENGTH: 68
<212> TYPE: DNA
<213> ORGANISM: Artificial Sequence
<220> FEATURE:
<223> OTHER INFORMATION: Synthetic oligonucleotide Primer used to construct SEQ ID NO:31
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 32

```
tgccaagctt accgtgnnsn nsnnsnnsnn snnsaggtgg nnsnnsggga acgtcttctc     60
atgctccg                                                            68
```

<210> SEQ ID NO 33
<211> LENGTH: 115
<212> TYPE: PRT
<213> ORGANISM: Artificial Sequence
<220> FEATURE:
<223> OTHER INFORMATION: Synthetic peptide amino acid sequence of construct for CH3+5 library
<220> FEATURE:
<221> NAME/KEY: MISC_FEATURE
<222> LOCATION: (19)..(21)
<223> OTHER INFORMATION: Xaa can be any naturally occurring amino acid that is substituted or inserted

```
<220> FEATURE:
<221> NAME/KEY: MISC_FEATURE
<222> LOCATION: (73)..(75)
<223> OTHER INFORMATION: Xaa can be any naturally occurring amino acid
      that is substituted or inserted
<220> FEATURE:
<221> NAME/KEY: MISC_FEATURE
<222> LOCATION: (76)..(80)
<223> OTHER INFORMATION: Xaa can be absent or any naturally occurring
      amino acid that is substituted or inserted
<220> FEATURE:
<221> NAME/KEY: MISC_FEATURE
<222> LOCATION: (83)..(84)
<223> OTHER INFORMATION: Xaa can be any naturally occurring amino acid
      that is substituted or inserted

<400> SEQUENCE: 33

Met Ala Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Xaa Xaa Xaa Xaa Xaa Xaa Xaa Xaa
65                  70                  75                  80

Arg Trp Xaa Xaa Gly Asn Val Phe Ser Cys Ser Val Met His Glu Ala
            85                  90                  95

Leu His Asn His Tyr Thr Gln Lys Ser Leu Ser Leu Ser Pro Gly Lys
            100                 105                 110

Ala Ala Ala
        115

<210> SEQ ID NO 34
<211> LENGTH: 347
<212> TYPE: DNA
<213> ORGANISM: Artificial Sequence
<220> FEATURE:
<223> OTHER INFORMATION: Synthetic oligonucleotide nucleotide sequence
      for CH3+5 library
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (225)..(226)
<223> OTHER INFORMATION: n is a, c, g, or t
<220> FEATURE:
<221> NAME/KEY: misc_feature
<222> LOCATION: (228)..(229)
<223> OTHER INFORMATION: n is a, c, g, or t
<220> FEATURE:
```

```
<221> NAME/KEY: misc_feature
<222> LOCATION: (231)..(232)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (237)..(238)
<223> OTHER INFORMATION: n is a, c, g, or t
<220> FEATURE:
<221> NAME/KEY: misc_feature
<222> LOCATION: (240)..(241)
<223> OTHER INFORMATION: n is a, c, g, or t
<220> FEATURE:
<221> NAME/KEY: misc_feature
<222> LOCATION: (249)..(250)
<223> OTHER INFORMATION: n is a, c, g, or t
<220> FEATURE:
<221> NAME/KEY: misc_feature
<222> LOCATION: (252)..(253)
<223> OTHER INFORMATION: n is a, c, g, or t

<400> SEQUENCE: 34
ccatggcccc ccgagaacca caggtgtaca ccctgccccc atcccgtgac gagctcnnsn      60
nsnnscaagt cagcctgacc tgcctggtca aaggcttcta tcccagcgac atcgccgtgg     120
agtgggagag caatgggcag ccggagaaca actacaagac cacgcctccc gtgctggact     180
ccgacggctc cttcttcctc tacagcaagc ttaccgtgnn snnsnnsnns nnsnnsnnsn     240
nsaggtggnn snnsgggaac gtcttctcat gctccgtgat gcatgaggct ctgcacaacc     300
actacacaca gaagagcctc tccctgtctc cgggtaaagc ggccgca                   347

<210> SEQ ID NO 35
<211> LENGTH: 74
<212> TYPE: DNA
<213> ORGANISM: Artificial Sequence
<220> FEATURE:
<223> OTHER INFORMATION: Synthetic oligonucleotide Primer used for
      construction of SEQ ID NO:34
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
```

```
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 35
tgccaagctt accgtgnnsn nsnnsnnsnn snnsnnsnns aggtggnnsn nsgggaacgt      60
cttctcatgc tccg                                                       74
```

MULTIVALENT IMMUNOGLOBULINS

This application is a continuation of U.S. application Ser. No. 12/307,578, filed Sep. 14, 2009, now abandoned, which is the U.S. national stage of International Application No. PCT/AT2007/000313, filed Jun. 26, 2007, which claims the benefit of priority from Austrian Patent Application No. A 1147/2006, filed Jul. 5, 2006, each of which is incorporated herein in its entirety.

SEQUENCE LISTING

This application contains a Sequence Listing which has been submitted electronically in ASCII format and is hereby incorporated by reference in its entirety. Said ASCII copy, created on Nov. 12, 2021, is named Revised_Sequence_Listing5.txt and is 32,768 bytes in size.

The present invention provides a multivalent immunoglobulin or part thereof binding specifically to at least two cell surface molecules of a single cell, with at least one modification in at least one structural loop region of said immunoglobulin determining binding to an epitope of said cell surface molecules wherein the unmodified immunoglobulin does not significantly bind to said epitope.

Monoclonal antibodies have found use in many therapeutic, diagnostic and analytical applications.

The basic antibody structure will be explained here using as example an intact IgG1 immunoglobulin. Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy-terminal CH3, at the base of the Y's stem. A short stretch, the switch, connects the heavy chain variable and constant regions. The hinge connects CH2 and CH3 (the Fe fragment) to the remainder of the antibody (the Fab fragments). One Fc and two identical Fab fragments can be produced by proteolytic cleavage of the hinge in an intact antibody molecule. The light chains are constructed of two domains, variable {VL) and constant (CL), separated by a switch.

Disulfide bonds in the hinge region connect the two heavy chains. The light chains are coupled to the heavy chains by additional disulfide bonds. Asn-linked carbohydrate moieties are attached at different positions in constant domains depending on the class of immunoglobulin. For IgG1 two disulfide bonds in the hinge region, between Cys235 and Cys238 pairs, unite the two heavy chains. The light chains are coupled to the heavy chains by two additional disulfide bonds, between Cys229s in the CH1 domains and Cys214s in the CL domains. Carbohydrate moieties are attached to Asn306 of each CH2, generating a pronounced bulge in the stem of the Y.

These features have profound functional consequences. The variable regions of both the heavy and light chains (VH) and (VL) lie at the "tips" of the Y, where they are positioned to react with antigen. This tip of the molecule is the side on which the N-terminus of the amino acid sequence is located. The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y.

Two types of light chain, termed lambda (λ) and kappa (κ), are found in antibodies. A given immunoglobulin either has κ chains or λ chains, never one of each. No functional difference has been found between antibodies having λ or κ light chains.

Each domain in an antibody molecule has a similar structure of two beta sheets packed tightly against each other in a com-pressed antiparallel beta barrel. This conserved structure is termed the immunoglobulin fold. The immunoglobulin fold of constant domains contains a 3-stranded sheet packed against a 4-stranded sheet. The fold is stabilized by hydrogen bonding between the beta strands of each sheet, by hydrophobic bonding between residues of opposite sheets in the interior, and by a disulfide bond between the sheets. The 3-stranded sheet comprises strands C, F, and G, and the 4-stranded sheet has strands A, B, E, and D. The letters A through G denote the sequential positions of the beta strands along the amino acid sequence of the immunoglobulin fold.

The fold of variable domains has 9 beta strands arranged in two sheets of 4 and 5 strands. The 5-stranded sheet is structurally homologous to the 3-stranded sheet of constant domains, but contains the extra strands C' and C". The remainder of the strands (A, B, C, D, E, F, G) have the same topology and similar structure as their counterparts in constant domain immunoglobulin folds. A disulfide bond links strands B and F in opposite sheets, as in constant domains.

The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B-C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B-C, C'-C", and F-G of the light chain variable domain and strands B-C, C'-C", and F-G of the heavy chain variable domain.

The loops which are not CDR-loops in a native immunoglobulin, or not part of the antigen-binding pocket as determined by the CDR loops, do not have antigen binding or epitope binding specificity, but contribute to the correct folding of the entire immunoglobulin molecule and/or its effector or other functions and are therefore called structural loops for the purpose of this invention. Prior art documents show that the immunoglobulin-like scaffold has been employed so far for the purpose of manipulating the existing antigen binding site, thereby introducing novel binding properties. So far, however, only the CDR regions have been engineered for antigen binding, in other words, in the case of the immunoglobulin fold, only the natural antigen binding site has been modified in order to change its binding affinity or specificity. A vast body of literature exists which describes different formats of such manipulated immunoglobulins, frequently expressed in the form of single-chain Fv fragments (scFv) or Fab fragments, either displayed on the surface of phage particles or solubly expressed in various prokaryotic or eukaryotic expression systems.

PCT/EP2006/050059 describes a method of engineering an immunoglobulin which comprises a modification in a structural loop region to obtain a new antigen binding sites. This method is broadly applicable to immunoglobulins and may be used to produce a series of immunoglobulins targeting a variety of antigens. Multivalent binders of cell-surface targets are not explicitly described.

US2005/266000A1 describes polypeptides comprising a variant heavy chain variable framework domain (VFR). A VFR is part of the antigen binding pocket or groove that may contact antigen. VFRs are part of the CDR loop region and located at a variable domain at the side of the CDR loops to support the antigen binding via the CDR loop region. Framework loops other than VFR have not been mutated for the purpose of engineering an antigen binding site.

Cell surface proteins associated with human cancers can be effective targets for monoclonal therapy. Antibodies can elicit antitumor responses by modulating cellular activation or through recruitment of the immune system.

Some mAbs exert part of their effect by cross-linking of the target, which may cluster the targets and result in activation, inhibition, or amplification of cell signalling, finally ending in cell arrest and/or apoptosis to the cellular target.

It has been demonstrated that some MAbs (anti-CD19, -CD20, -CD21, and -CD22) that have little or no inherent anti-growth activity on lymphoma cell lines can be converted into potent antitumor agents by using them as tetravalent homodimers. These activities might be enhanced in vivo by the recruitment of effector cells and/or complement. Another strategy used for therapeutic mAbs is to couple a cytotoxic drug to the mAb. Such an immunotoxin may bind to the cell surface target followed by internalization, releasing the drug to kill the cell. Clustering of the target as a prerequisite to internalization may be necessary.

To enhance the potency of mAbs that exert their effect through the clustering of target molecules, various multivalent Ab formats have been designed. Covalently linked full-length IgGs that form tetravalent Abs and naturally occurring IgM and IgG Abs mimicking polymeric IgM and IgA via the use of their secretory tailpiece have been devised. Another tetravalent format was designed by adding Fab at the C terminus of each H chain of a full-length IgG.

To improve tumor penetration, smaller constructs using single-chain Fv (scFv)$_2$ fragments (each Fv consisting of variable light and variable heavy domains connected by peptide linkers) have been joined together to form multivalent complexes. Such constructs may have relatively short half-lives (compared with those of full-length mAbs), consequently this has been addressed by joining these scFv multimers to IgG Fc fragments. With scFv and similar formats it is difficult to control formation of the exact multimerization degree, i.e., dimers, trimers, tetramers, and larger complexes may form in varying ratios depending on the basic construct and expression method.

Any of the known formats to produce multivalent immunoglobulins have certain disadvantages, be it immunogenicity, in vivo-half life or production issues.

It is the object of the present invention to provide a modular system which allows designing a cell targeting multivalent immunoglobulin according to the respective need, to solve prior art problems.

BRIEF DESCRIPTION OF THE INVENTION

The present invention provides immunoglobulin domains which bind to cell surface proteins via modified structural loops to provide additional binding to a cell surface molecule thus enabling crosslinking of cell-surface receptors.

According to the present invention a multivalent immunoglobulin or binding part thereof is provided that specifically binds to at least two cell surface molecules of a single cell with at least one modification in at least one structural loop region of said immunoglobulin determining binding to an epitope of said cell surface molecules, including structures of antigenic properties, located on a single cell or available within a homogenous cell population, wherein the unmodified immunoglobulin does not significantly bind to said epitope.

According to the present invention, the inventive multivalent immunoglobulin can be further combined with one or more modified immunoglobulins or with unmodified immunoglobulins, or parts thereof, to obtain a combination immunoglobulin.

Preferably, the modification of the structural loop domain within the nucleotide or amino acid sequence is a deletion, a substitution, an insertion or a combination thereof.

The present invention also provides a nucleic acid encoding the inventive immunoglobulin or part thereof and a method for engineering a multivalent immunoglobulin according to the invention comprising the steps of:

providing a nucleic acid encoding an immunoglobulin comprising at least one structural loop region, modifying at least one nucleotide residue of said structural loop region, transferring said modified nucleic acid in an expression system, expressing said multivalent immunoglobulin, contacting the expressed multivalent immunoglobulin with an epitope, and determining whether said multivalent immunoglobulin binds to said epitope.

Further, the use of the multivalent immunoglobulin according to the invention for the preparation of a medicament for therapeutic use, for example for tumor cell treatment and pathogen infected cells is provided.

DETAILED DESCRIPTION OF THE INVENTION

The modified immunoglobulin domains according to the invention can be used as such or incorporated into various known antibody formats such as complete antibodies, Fabs, single chain Fvs, Fab2, minibodies and the like to provide additional binding sites for cell surface epitopes or receptors.

In particular, the present invention relates to a method for engineering an immunoglobulin binding specifically to epitopes of antigens. Through the modification in the structural loop region the immunoglobulin may be engineered to bind to the epitope. In a preferred embodiment the immunoglobulin is binding specifically to at least two such epitopes that differ from each other, originating from or mimicking either the same antigen or different antigens.

For example, the method according to the invention refers to engineering an immunoglobulin binding specifically to at least one first epitope and comprising at least one modification in at least one structural loop region of said immunoglobulin and determining the specific binding of said at least one loop region to at least one second epitope, wherein the unmodified structural loop region (non-CDR region) does not specifically bind to said at least one second epitope, comprising the steps of:

providing a nucleic acid encoding an immunoglobulin binding specifically to at least one first epitope and comprising at least one structural loop region, modifying at least one nucleotide residue of at least one of said loop regions encoded by said nucleic acid, transferring said modified nucleic acid in an expression system, expressing said modified immunoglobulin,
contacting the expressed modified immunoglobulin with said at least one second epitope, and
determining whether said modified immunoglobulin binds specifically to the second epitope.

The method according to the invention preferably refers to at least one modification in at least one structural loop region of said immunoglobulin and determining the specific binding of said at least one loop region to at least one molecule selected from the group consisting of cell surface antigens, wherein the immunoglobulin containing an unmodified structural loop region does not specifically bind to said at least one molecule.

The term "immunoglobulin" as used herein is including immunoglobulins or parts or fragments or derivatives of immunoglobulins. Thus, it includes an "immunoglobulin domain peptide" to be modified according to the present invention (as used herein the terms immunoglobulin and antibody are interchangeable) as well as immunoglobulin domains or parts thereof that contain a structural loop, or a structural loop of such domains, such as a minidomain. The immunoglobulins can be used as isolated peptides or as combination molecules with other peptides. In some cases it is preferable to use a defined modified structural loop or a structural loop region, or parts thereof, as isolated molecules for binding or combination purposes. The "immunoglobulin domain" as defined herein contains such immunoglobulin domain peptides or polypeptides that may have specific binding characteristics upon modifying and engineering. The peptides are homologous to immunoglobulin domain sequences, and are preferably at least 5 amino acids long, more preferably at least 10 or even at least 50 or 100 amino acids long, and constitute at least partially a structural loop or the structural loop region, or the non-CDR loop region of the domain. Preferably the peptides exclude those insertions that are considered non-functional amino acids, hybrid or chimeric CDR-regions or CDR-like regions and/or canonical structures of CDR regions. The binding characteristics relate to specific epitope binding, affinity and avidity.

A derivative of an iummunoglobulin according to the invention is any combination of one or more imunoglobulins of the invention and or a fusion protein in which any domain or minidomain of the immunoglobulin of the invention may be fused at any position of one ore more other proteins (such as other immunoglobulins, ligands, scaffold proteins, enzymes, toxins and the like). A derivative of the immunoglobulin of the invention may also be obtained by recombination techniques or binding to other substances by various chemical techniques such as covalent coupling, electrostatic interaction, di-sulphide bonding etc.

The other substances bound to the immunoglobulins may be lipids, carbohydrates, nucleic acids, organic and anorganic molecules or any combination thereof (e.g. PEG, prodrugs or drugs). A derivative is also an immunoglobulin with the same amino acid sequence but made completely or partly from non-natural or chemically modified amino acids.

The engineered molecules according to the present invention will be useful as stand-alone proteins as well as fusion proteins or derivatives, most typically fused in such a way as to be part of larger antibody structures or complete antibody molecules, or parts thereof such as Fab fragments, Fc fragments, Fv fragments and others. It will be possible to use the engineered proteins to produce molecules which are bispecific, trispecific, and maybe even carry more specificities at the same time, and it will be possible at the same time to control and preselect the valency of binding at the same time according to the requirements of the planned use of such molecules.

Another aspect of the present invention relates to an immunoglobulin with at least one loop region, characterised in that said at least one loop region comprises at least one amino acid modification forming at least one modified loop region, wherein said at least one modified loop region binds specifically to at least one epitope of an antigen It is preferred to molecularly combine at least one modified antibody domain, which is binding to the specific partner via the non-variable sequences or a structural loop) with at least one other binding molecule which can be an antibody, antibody fragment, a soluble receptor, a ligand or another modified antibody domain.

The molecule that functions as a part of a binding pair that is specifically recognized by the immunoglobulin according to the invention is preferably selected from the group consisting of proteinaceous molecules, nucleic acids and carbohydrates.

The loop regions of the modified immunoglobulins may specifically bind to any kind of binding molecules or structures, in particular to antigens, proteinaceous molecules, proteins, peptides, polypeptides, nucleic acids, glycans, carbohydrates, lipids, small organic molecules, anorganic molecules, or combinations or fusions thereof. Of course, the modified immunoglobulins may comprise at least two loops or loop regions whereby each of the loops or loop regions may specifically bind to different molecules or epitopes.

According to the present invention, binding regions to antigens or antigen binding sites of all kinds of cell surface antigens, may be introduced into a structural loop of a given antibody structure.

The term "antigen" according to the present invention shall mean molecules or structures known to interact or capable of interacting with the CDR-loop region of immunoglobulins. Structural loop regions of the prior art referring to native antibodies, do not interact with antigens but rather contribute to the overall structure and/or to the binding to effector molecules. Only upon engineering according to the invention structural loops may form antigen binding pockets without involvement of CDR loops or the CDR region.

The term "cell surface antigens" according to the present invention shall include all antigens on capable of being recognised by an antibody structure on the surface of a cell, and fragments of such molecules. Preferred "cell surface antigens" are those antigens, which have already been proven to be or which are capable of being immunologically or therapeutically relevant, especially those, for which a preclinical or clinical efficacy has been tested. Those cell surface molecules are specifically relevant for the purpose of the present invention, which mediate cell killing activity. Upon binding of the immunoglobulin according to the invention to at least two of those cell surface molecules the immune system provides for cytolysis or cell death, thus a potent means for attacking human cells may be provided.

Preferably the antigen is selected from cell surface antigens, including receptors, in particular from the group consisting of erbB receptor tyrosine kinases (such as EGFR, HER2, HER3 and HER4, but not limited to these), molecules of the TNF-receptor superfamily, such as Apo-1 receptor, TNFR1, TNFR2, nerve growth factor receptor NGFR, CD40, T-cell surface molecules, T-cell receptors, T-cell antigen OX40, TACI-receptor, BCMA, Apo-3, DR4, DR5, DR6, decoy receptors such as DcR1, DcR2, CAR1, HVEM, GITR, ZTNFR-5, NTR-1, TNFL1 but not limited to these molecules, B-cell surface antigens, such as CD10, CD19, CD20, CD21, CD22, antigens or markers of solid tumors or hematologic cancer cells, cells of lymphoma or leukaemia, other blood cells including blood platelets, but not limited to these molecules.

According to a further preferred embodiment the antigen or the molecule binding to the modified structural loop region is selected from the group consisting of tumor associated antigens, in particular EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, allergy related molecules IgE, cKIT and Fc-epsilon-receptorI, IRp60, IL-5 receptor, CCR3, red blood cell receptor (CR1), human serum albumin, mouse serum albumin, rat serum albumin, neonatal Fc-gamma-receptor FcRn, Fc-gamma-receptors Fc-gamma RI, Fc-gamma-RII, Fc-gamma RIII, Fc-alpha-receptors, Fc-epsilon-receptors, fluorescein, lysozyme, toll-like receptor 9, erythropoietin, CD2, CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD64, CD80, CD147, GD3, IL-1, IL-1R, IL-2, IL-2R, IL-4, IL-5, IL-6, IL-6R, IL-8, IL-12, IL-15, IL-17, IL-18, IL-23, LIF, OSM, interferon alpha, interferon beta, interferon gamma; TNF-alpha, TNFbeta2, TNFalpha, TNFalphabeta, TNF-R1, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF-R, EPO; LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, GM-CSF, M-CSF, RANKL, VLA-1, VLA-4, L-selectin, anti-Id, E-selectin, HLA, HLA-DR, CTLA-4, T cell receptor, B7-1, B7-2, VNRintegrin, TGFbeta1, TGFbeta2, eotaxin1, BLyS (B-lymphocyte Stimulator), complement C5, IgE, IgA, IgD, IgM, IgG, factor VII, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, carbohydrates such as blood group antigens and related carbohydrates, Galili-Glycosylation, Gastrin, Gastrin receptors, tumor associated carbohydrates, Hapten NP-cap or NIP-cap, T cell receptor alpha/beta, E-selectin, P-glycoprotein, MRP3, MRP5, glutathione-S-transferase pi (multi drug resistance proteins), alpha-granule membrane protein (GMP) 140, digoxin, placental alkaline phosphatase (PLAP) and testicular PLAP-like alkaline phosphatase, transferrin receptor, Heparanase I, human cardiac myosin, Glycoprotein IIb/IIIa (GPIIb/IIIa), human cytomegalovirus (HCMV) gH envelope glycoprotein, HIV gp120, HCMV, respiratory syncital virus RSV F, RSVF Fgp, VNRintegrin, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, *Clostridium perfringens* toxin and fragments thereof.

Substructures of antigens are generally referred to as "epitopes" (e.g. B-cell epitopes, T-cell epitopes), as long as they are immunologically relevant, i.e. are also recognisable by natural or monoclonal antibodies. The term "epitope" according to the present invention shall mean a molecular structure which may completely make up a specific binding partner or be part of a specific binding partner to the binding domain or the immunoglobulin of the present invention.

Chemically, an epitope may either be composed of a carbohydrate, a peptide, a fatty acid, an anorganic substance or derivatives thereof and any combinations thereof. If an epitope is a peptide or polypeptide, there will usually be at least 3 amino acids, preferably 8 to 50 amino acids, and more preferably between about 10-20 amino acids included in the peptide. There is no critical upper limit to the length of the peptide, which could comprise nearly the full length of the polypeptide sequence. Epitopes can be either be linear or conformational epitopes. A linear epitope is comprised of a single segment of a primary sequence of a polypeptide chain. Linear epitopes can be contiguous or overlapping. Conformational epitopes are comprised of amino acids brought together by folding of the polypeptide to form a tertiary structure and the amino acids are not necessarily adjacent to one another in the linear sequence.

Specifically, epitopes are at least part of diagnostically relevant molecules, i.e. the absence or presence of an epitope in a sample is qualitatively or quantitatively correlated to either a disease or to the health status or to a process status in manufacturing or to environmental and food status. Epitopes may also be at least part of therapeutically relevant molecules, i.e. molecules which can be targeted by the specific binding domain which changes the course of the disease.

Preferably, the new antigen binding sites in the structural loops are introduced by substitution, deletion and/or insertion of one or more elements in the sequence of the immunoglobulin, in particular of the nucleotide sequence.

According to another preferred embodiment of the present invention the modification of at least one nucleotide results in a substitution, deletion and/or insertion of the amino acid sequence of the immunoglobulin encoded by said nucleic acid.

The modification of the at least one loop region may result in a substitution, deletion and/or insertion of 1 or more nucleotides or amino acids, preferably a point mutation, or even the exchange of whole loops, more preferred the change of at least 2, 3, 4, 5, 6, 7, 8, 9, 10, 11, 12, 13, 14 or 15, up to 30 amino acids. Thereby the modified sequence comprises amino acids not included in the conserved regions of the structural loops, the newly introduced amino acids being naturally occurring, but foreign to the site of modification, or substitutes of naturally occurring amino acids. When the foreign amino acid is selected from a specific group of amino acids, such as amino acids with specific polarity, or hydrophobicity, a library enriched in the specific group of amino acids at the randomized positions can be obtained according to the invention. Such libraries are also called "focused" libraries.

The randomly modified nucleic acid molecule may comprise the herein identified repeating units, which code for all known naturally occurring amino acids or a subset thereof. Those libraries that contain modified sequences wherein a specific subset of amino acids are used for modification purposes are called "focused" libraries. The member of such libraries have an increased probability of an amino acid of such a subset at the modified position, which is at least two times higher than usual, preferably at least 3 times or even at least 4 times higher. Such libraries have also a limited or lower number of library members, so that the number of actual library members reaches the number of theoretical library members. In some cases the number of library members of a focused library is not less than $10^3$ times the theoretical number, preferably not less than $10^2$ times, most preferably not less than 10 times.

A library according to the invention may be designed as a dedicated library that contains at least 50% specific formats, preferably at least 60%, more preferred at least 70%, more preferred at least 80%, more preferred at least 90%, or those that mainly consist of specific antibody formats. Specific antibody formats are preferred, such that the preferred library according to the invention it is selected from the group consisting of a VH library, VHH library, Vkappa library, Vlambda library, Fab library, a CH1/CL library and a CH3 library. Libraries characterized by the content of composite molecules containing more than one antibody domains, such as an IgG library or Fc library are specially preferred. Other preferred libraries are those containing T-cell receptors, forming T-cell receptor libraries. Further preferred libraries are epitope libraries, wherein the fusion protein comprises a molecule with a variant of an epitope, also enabling the selection of competitive molecules having similar binding function, but different functionality. Exemplary is a TNFalpha library, wherein trimers of the TNFalpha fusion protein are displayed by a single genetic package.

However, the maximum number of amino acids inserted into a loop region of an immunoglobulin preferably may not exceed the number of 30, preferably 25, more preferably 20 amino acids at a maximum. The substitution and the insertion of the amino acids occurs preferably randomly or semi-randomly using all possible amino acids or a selection of preferred amino acids for randomization purposes, by methods known in the art and as disclosed in the present patent application.

The site of modification may be at a specific single structural loop or a structural loop region. A loop regions usually is composed of at least two, preferably at least 3 or at least 4 loops that are adjacent to each other, and which may contribute to the binding of an antigen through forming an antigen binding site or antigen binding pocket. It is preferred that the one or more sites of modification are located within the area of 10 amino acids, more preferably within 20, 30, 40, 50, 60, 70, 80, 90 up to 100 amino acids, in particular within a structural region to form a surface or pocket where the antigen can sterically access the loop regions.

The at least one loop region is preferably mutated or modified to produce libraries, preferably by random, semi-random or, in particular, by site-directed random mutagenesis methods, in particular to delete, exchange or introduce randomly generated inserts into structural loops. Alternatively preferred is the use of combinatorial approaches. Any of the known mutagenesis methods may be employed, among them cassette mutagenesis. These methods may be used to make amino acid modifications at desired positions of the immunoglobulin of the present invention. In some cases positions are chosen randomly, e.g. with either any of the possible amino acids or a selection of preferred amino acids to randomize loop sequences, or amino acid changes are made using simplistic rules. For example all residues may be mutated preferably to specific amino acids, such as alanine, referred to as amino acid or alanine scanning. Such methods may be coupled with more sophisticated engineering approaches that employ selection methods to screen higher levels of sequence diversity.

A preferred method according to the invention refers to a randomly modified nucleic acid molecule coding for an immunoglobulin, immunoglobulin domain or a part thereof which comprises at least one nucleotide repeating unit within a structural loop coding region having the sequence 5'-NNS-3', 5'-NNN-3', 5'-NNB-3' or 5'-NNK-3'. In some embodiments the modified nucleic acid comprises nucleotide codons selected from the group of TMT, WMT, BMT, RMC, RMG, MRT, SRC, KMT, RST, YMT, MKC, RSA, RRC, NNK, NNN, NNS or any combination thereof (the coding is according to IUPAC).

The modification of the nucleic acid molecule may be performed by introducing synthetic oligonuleotides into a larger segment of nucleic acid or by de novo synthesis of a complete nucleic acid molecule. Synthesis of nucleic acid may be performed with tri-nucleotide building blocks which would reduce the number of nonsense sequence combinations if a subset of amino acids is to be encoded (e.g. Yanez et al. Nucleic Acids Res. (2004) 32:e158; Virnekas et al. Nucleic Acids Res. (1994) 22:5600-5607).

The randomly modified nucleic acid molecule may comprise the above identified repeating units, which code for all known naturally occurring amino acids.

As is well-known in the art, there are a variety of selection technologies that may be used for the identification and isolation of proteins with certain binding characteristics and affinities, including, for example, display technologies such as phage display, ribosome display, cell surface display, and the like, as described below. Methods for production and screening of antibody variants are well-known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76.

A "structural loop" or "non-CDR-loop" according to the present invention is to be understood in the following manner: immunoglobulins are made of domains with a so called immunoglobulin fold. In essence, antiparallel beta sheets are connected by loops to form a compressed antiparallel beta barrel. In the variable region, some of the loops of the domains contribute essentially to the specificity of the antibody, i.e. the binding to an antigen by the natural binding site of an antibody. These loops are called CDR-loops. The CDR loops are located within the CDR loop region, which may in some cases also the variable framework region (called "VFR") adjacent to the CDR loops. It is known that VFRs may contribute to the antigen binding pocket of an antibody, which generally is mainly determined by the CDR loops. Thus, those VFRs are considered as part of the CDR loop region, and would not be appropriately used for the purpose of the invention. Contrary to those VFRs within the CDR loop region or located proximal to the CDR loops, other VFRs of variable domains would be particularly suitable to be used according to the invention. Those are the structural loops of the VFRs located opposite to the CDR loop region, or at the C-terminal side of a variable immunoglobulin domain.

All other loops of antibody domains are rather contributing to the structure of the molecule and/or the effector function. These loops are defined herein as "structural loops" or non-CDR-loops, which would also exclude any VFRs within the CDR loop region.

The nucleic acid molecules encoding the modified immunoglobulins (and always included throughout the whole specification below: immunoglobulin fragments or derivatives) may be cloned into host cells, expressed and assayed for their binding specificities. These practices are carried out using well-known procedures, and a variety of methods that may find use in the present invention are described in Molecular Cloning-A Laboratory Manual, 3.sup.rd Ed. (Maniatis, Cold Spring Harbor Laboratory Press, New York, 2001), and Current Protocols in Molecular Biology (John Wiley & Sons). The nucleic acids that encode the modified immunoglobulins of the present invention may be incorporated into an expression vector in order to express said immunoglobulins. Expression vectors typically comprise an immunoglobulin operably linked that is placed in a functional relationship, with control or regulatory sequences, selectable markers, any fusion partners, and/or additional elements. The modified immunoglobulins of the present invention may be produced by culturing a host cell transformed with nucleic acid, preferably an expression vector, containing nucleic acid encoding the modified immunoglobulins, under the appropriate conditions to induce or cause expression of the modified immunoglobulins. The methods of introducing exogenous nucleic acid molecules into a host are well known in the art, and will vary with the host used. Of course, also acellular or cell free expression systems for the expression of modified immunoglobulins may be employed.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may than also be integrated into the host chromosome.

According to a preferred embodiment of the present invention the expression system comprises a vector. Any expression vector known in the art may be used for this purpose as appropriate.

The modified immunoglobulin is preferably expressed in a host, preferably in a bacterial, a yeast, a plant cell, in an animal cell or in a plant or animal.

A wide variety of appropriate host cells may be used to express the modified immunoglobulin, including but not limited to mammalian cells (animal cells) or and plant cells), bacteria (e.g. *Bacillus subtilis, Escherichia coli*), insect cells, and yeast (e.g. *Pichia pastoris, Saccharomyces cerevisiae*). For example, a variety of cell lines that may find use in the present invention are described in the ATCC cell line catalog, available from the American Type Culture Collection. Furthermore, also plants and animals may be used as hosts for the expression of the immunoglobulin according to the present invention. The expression as well as the transfection vectors or cassettes may be selected according to the host used.

Of course also acellular or cell free protein expression systems may be used. In vitro transcription/translation protein expression platforms, that produce sufficient amounts of protein offer many advantages of a cell-free protein expression, eliminating the need for laborious up- and downstream steps (e.g. host cell transformation, culturing, or lysis) typically associated with cell-based expression systems.

In a preferred embodiment of the present invention, the modified immunoglobulins are purified or isolated after expression. Modified immunoglobulins may be isolated or purified in a variety of ways known to those skilled in the art. Standard purification methods include chromatographic techniques, including affinity chromatography, ion exchange or hydrophobix chromatography, electrophoretic, immunological, precipitation, dialysis, filtration, concentration, and chromatofocusing techniques. Purification is often enabled by a particular fusion partner. For example, antibodies may be purified using glutathione resin if a GST fusion is employed, Ni+2 affinity chromatography if a His-tag is employed or immobilized anti-flag antibody if a flag-tag is used. For general guidance in suitable purification techniques, see Antibody Purification: Principles and Practice, 3.sup.rd Ed., Scopes, Springer-Verlag, NY, 1994. Of course, it is also possible to express the modified immunoglobulins according to the present invention on the surface of a host, in particular on the surface of a bacterial, insect or yeast cell or on the surface of phages or viruses.

Modified immunoglobulins may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label, for example an enzyme, an immune label, isotopic label, or small molecule label such as a fluorescent or colorimetric dye or a luminogenic molecule.

In a preferred embodiment, the functional and/or biophysical properties of the immunoglobulins are screened in an in vitro assay. In a preferred embodiment, the antibody is screened for functionality, for example its ability to catalyze a reaction or its binding affinity to its target.

Assays may employ a variety of detection methods including but not limited to chromogenic, fluorescent, luminescent, or isotopic labels.

As is known in the art, a subset of screening methods are those that select for favorable members of a library. The methods are herein referred to as "selection methods", and these methods find use in the present invention for screening modified immunoglobulins. When immunoglobulins libraries are screened using a selection method, only those members of a library that are favorable, that is which meet some selection criteria, are propagated, isolated, and/or observed. As will be appreciated, because only the most fit variants are observed, such methods enable the screening of libraries that are larger than those screenable by methods that assay the fitness of library members individually. Selection is enabled by any method, technique, or fusion partner that links, covalently or noncovalently, the phenotype of immunoglobulins with its genotype, that is the function of a antibody with the nucleic acid that encodes it. For example the use of phage display as a selection method is enabled by the fusion of library members to the gene III protein. In this way, selection or isolation of modified immunoglobulins that meet some criteria, for example binding affinity to the immunoglobulin's target, also selects for or isolates the nucleic acid that encodes it. Once isolated, the gene or genes encoding modified immunoglobulins may then be amplified. This process of isolation and amplification, referred to as panning, may be repeated, allowing favorable antibody variants in the library to be enriched. Nucleic acid sequencing of the attached nucleic acid ultimately allows for gene identification.

A variety of selection methods are known in the art that may find use in the present invention for screening immunoglobulin libraries. These include but are not limited to phage display (Phage display of peptides and antibodies: a laboratory manual, Kay et al., 1996, Academic Press, San Diego, Calif., 1996; Low-man et al., 1991, Biochemistry 30:10832-10838; Smith, 1985, Science 228:1315-1317) and its derivatives such as selective phage infection (Malmborg et al., 1997, J Mol Biol 273:544-551), selectively infective phage (Krebber et al., 1997, J Mol Biol 268:619-630), and delayed infectivity panning (Benhar et al., 2000, J Mol Biol 301:893-904), cell surface display (Witrrup, 2001, Curr Opin Biotechnol, 12:395-399) such as display on bacteria (Georgiou et al., 1997, Nat Biotechnol 15:29-34; Georgiou et al., 1993, Trends Biotechnol 11:6-10; Lee et al., 2000, Nat Biotechnol 18:645-648; Jun et al., 1998, Nat Biotechnol 16:576-80), yeast (Boder & Wittrup, 2000, Methods Enzymol 328:430-44; Boder & Wittrup, 1997, Nat Biotechnol 15:553-557), and mammalian cells (Whitehorn et al., 1995, Bio/technology 13:1215-1219), as well as in vitro display technologies (Amstutz et al., 2001, Curr Opin Biotechnol 12:400-405) such as polysome display (Mattheakis et al., 1994, Proc Natl Acad Sci USA 91:9022-9026), ribosome display (Hanes et al., 1997, Proc Natl Acad Sci USA 94:4937-4942), mRNA display (Roberts & Szostak, 1997, Proc Natl Acad Sci USA 94:12297-12302; Nemoto et al., 1997, FEBS Lett 414:405-408), and ribosome-inactivation display system (Zhou et al., 2002, J Am Chem Soc 124, 538-543).

Other selection methods that may find use in the present invention include methods that do not rely on display, such as in vivo methods including but not limited to periplasmic expression and cytometric screening (Chen et al., 2001, Nat Biotechnol 19:537-542), the antibody fragment complementation assay (Johnsson & Varshaysky, 1994, Proc Natl Acad Sci USA 91:10340-10344; Pelletier et al., 1998, Proc Natl Acad Sci USA 95:12141-12146), and the yeast two hybrid screen (Fields & Song, 1989, Nature 340:245-246) used in selection mode (Visintin et al., 1999, Proc Natl Acad Sci USA 96:11723-11728). In an alternate embodiment, selection is enabled by a fusion partner that binds to a specific sequence on the expression vector, thus linking covalently or noncovalently the fusion partner and associated Fc variant library member with the nucleic acid that encodes them.

In an alternative embodiment, in vivo selection can occur if expression of the antibody imparts some growth, reproduction, or survival advantage to the cell.

A subset of selection methods referred to as "directed evolution" methods are those that include the mating or breeding of favourable sequences during selection, sometimes with the incorporation of new mutations. As will be appreciated by those skilled in the art, directed evolution methods can facilitate identification of the most favourable sequences in a library, and can increase the diversity of sequences that are screened. A variety of directed evolution methods are known in the art that may find use in the present invention for screening antibody variants, including but not limited to DNA shuffling (PCT WO 00/42561 A3; PCT WO 01/70947 A3), exon shuffling (U.S. Pat. No. 6,365,377; Kolkman & Stemmer, 2001, Nat Biotechnol 19:423-428), family shuffling (Crameri et al., 1998, Nature 391:288-291; U.S. Pat. No. 6,376,246), RACHITT™ (Coco et al., 2001, Nat Bio-technol 19:354-359; PCT WO 02/06469), STEP and random priming of in vitro recombination (Zhao et al., 1998, Nat Biotechnol 16:258-261; Shao et al., 1998, Nucleic Acids Res 26:681-683), exonuclease mediated gene assembly (U.S. Pat. Nos. 6,352,842; 6,361,974), Gene Site Saturation Mutagenesis™ (U.S. Pat. No. 6,358,709), Gene Reassembly™ (U.S. Pat. No. 6,358,709), SCRATCHY (Lutz et al., 2001, Proc Natl Acad Sci USA 98:11248-11253), DNA fragmentation methods (Kikuchi et al., Gene 236:159-167), single-stranded DNA shuffling (Kikuchi et al., 2000, Gene 243:133-137), and AMEsystem™ directed evolution antibody engineering technology (Applied Molecular Evolution) (U.S. Pat. Nos. 5,824,514; 5,817,483; 5,814,476; 5,763,192; 5,723,323).

According to a preferred embodiment of the present invention the specific binding of the modified immunoglobulin to the molecule is determined by a binding assay selected from the group consisting of immunological assays, preferably enzyme linked immunosorbent assays (ELISA), surface plasmon resonance assays, saturation transfer difference nuclear magnetic resonance spectroscopy, transfer NOE (trNOE) nuclear magnetic resonance spectroscopy, competitive assays, tissue binding assays, live cell binding assays and cellular extract assays.

Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE™), isothermal titration calorimetry, differential scanning calorimetry, gel electrophoresis, and chromatography including gel filtration. These and other methods may take advantage of some fusion partner or label.

The modified immunoglobulin is preferably conjugated to a label or reporter molecule, selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Modified immunoglobulins conjugated to labels or reporter molecules may be used, for instance, in diagnostic methods.

The modified immunoglobulin may be conjugated to other molecules which allow the simple detection of said conjugate in, for instance, binding assays (e.g. ELISA) and binding studies.

In a preferred embodiment, antibody variants are screened using one or more cell-based or in vivo assays. For such assays, purified or unpurified modified immunoglobulins are typically added exogenously such that cells are exposed to individual immunoglobulins or pools of immunoglobulins belonging to a library. These assays are typically, but not always, based on the function of the immunoglobulin; that is, the ability of the antibody to bind to its target and mediate some biochemical event, for example effector function, ligand/receptor binding inhibition, apoptosis, and the like. Such assays often involve monitoring the response of cells to the antibody, for example cell survival, cell death, change in cellular morphology, or transcriptional activation such as cellular expression of a natural gene or reporter gene. For example, such assays may measure the ability of antibody variants to elicit ADCC, ADCP, or CDC. For some assays additional cells or components, that is in addition to the target cells, may need to be added, for example example serum complement, or effector cells such as peripheral blood monocytes (PBMCs), NK cells, macrophages, and the like. Such additional cells may be from any organism, preferably humans, mice, rat, rabbit, and monkey. Immunoglobulins may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored.

In a preferred embodiment, the DELFIART EuTDA-based cytotoxicity assay (Perkin Elmer, MA) may be used. Alternatively, dead or damaged target cells may be monitored by measuring the release of one or more natural intracellular components, for example lactate dehydrogenase. Transcriptional activation may also serve as a method for assaying function in cell-based assays. In this case, response may be monitored by assaying for natural genes or immunoglobulins which may be upregulated, for example the release of certain interleukins may be measured, or alternatively readout may be via a reporter construct. Cell-based assays may also involve the measure of morphological changes of cells as a response to the presence of modified immunoglobulins. Cell types for such assays may be prokaryotic or eukaryotic, and a variety of cell lines that are known in the art may be employed. Alternatively, cell-based screens are per-formed using cells that have been transformed or transfected with nucleic acids encoding the variants. That is, antibody variants are not added exogenously to the cells. For example, in one embodiment, the cell-based screen utilizes cell surface display. A fusion partner can be employed that enables display of modified immunoglobulins on the surface of cells (Witrrup, 2001, Curr Opin Biotechnol, 12:395-399).

In a preferred embodiment, the immunogenicity of the modified immunoglobulins may be determined experimentally using one or more cell-based assays. In a preferred embodiment, ex vivo T-cell activation assays are used to experimentally quantitate immunogenicity. In this method, antigen presenting cells and naive T cells from matched donors are challenged with a peptide or whole antibody of interest one or more times. Then, T cell activation can be detected using a number of methods, for example by monitoring production of cytokines or measuring uptake of tritiated thymidine. In the most preferred embodiment, interferon gamma production is monitored using Elispot assays (Schmittel et. al., 2000, J. Immunol. Meth., 24: 17-24).

The biological properties of the modified immunoglobulins of the present invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic with the appropriate half-life, effector function, apoptotic activity, cytotoxic or cytolytic activity. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the modified immunoglobulins of the present invention. Tests of the substances in humans are ultimately required for approval as drugs, and thus of course these experiments are contemplated. Thus the modified immunoglobulins of the present invention may be tested in humans to determine their therapeutic efficacy, toxicity, immunogenicity, pharmacokinetics, and/or other clinical properties. Especially those multivalent immunoglobulins according to the invention that bind to single cell through at least two surface antigens, preferably binding of at least three structures cross-linking target cells, would be considered preapoptotic and exert apoptotic activity upon cell targeting and cross-linking. Multivalent binding provides a relatively large association of binding partners, also called cross-linking, which is a prerequisite for apoptosis.

The modified immunoglobulins of the present invention may find use in a wide range of antibody products. In one embodiment the antibody variant of the present invention is used for therapy or prophylaxis, e.g. as an active or passive immunotherapy, for preparative, industrial or analytic use, as a diagnostic, an industrial compound or a research reagent, preferably a therapeutic. The modified immunoglobulin or antibody variant may find use in an antibody composition that is monoclonal or polyclonal. In a preferred embodiment, the modified immunoglobulins of the present invention are used to capture or kill target cells that bear the target antigen, for example cancer cells. In an alternate embodiment, the modified immunoglobulins of the present invention are used to block, antagonize, or agonize the target antigen, for example by antagonizing a cytokine or cytokine receptor.

In an alternately preferred embodiment, the modified immunoglobulins of the present invention are used to block, antagonize, or agonize growth factors or growth factor receptors and thereby mediate killing the target cells that bear or need the target antigen.

In an alternately preferred embodiment, the modified immunoglobulins of the present invention are used to block, antagonize, or agonize enzymes and substrate of enzymes.

The modified immunoglobulins of the present invention may be used for various therapeutic purposes, preferably for active or passive immunotherapy.

Specifically the immunoglobulin according to the present invention or obtainable by a method according to the present invention can be used for the preparation of a vaccine for active immunization. Hereby the immunoglobulin is either used as an antigenic drug substance to formulate a vaccine or used for fishing or capturing antigenic structures ex vivo or in vivo for use in a vaccine formulation.

In a preferred embodiment, an antibody comprising the modified immunoglobulins is ad-ministered to a patient to treat a specific disorder. A "patient" for the purposes of the present invention includes both humans and other animals, preferably mammals and most preferably humans. By "specific disorder" herein is meant a disorder that may be ameliorated by the administration of a pharmaceutical composition comprising a modified immunoglobulin of the present invention.

In one embodiment, a modified immunoglobulin according to the present invention is the only therapeutically active agent administered to a patient. Alternatively, the modified immunoglobulin according the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The modified immunoglobulins may be administered concomitantly with one or more other therapeutic regimens. For example, an antibody variant of the present invention may be administered to the patient along with chemotherapy, radiation therapy, or both chemotherapy and radiation therapy. In one embodiment, the modified immunoglobulins of the present invention may be administered in conjunction with one or more antibodies, which may or may not comprise a antibody variant of the present invention. In accordance with another embodiment of the invention, the modified immunoglobulins of the present invention and one or more other anti-cancer therapies are employed to treat cancer cells ex vivo. It is contemplated that such ex vivo treatment may be useful in bone marrow transplantation and particularly, autologous bone marrow transplantation. It is of course contemplated that the antibodies of the invention can be employed in combination with still other therapeutic techniques such as surgery.

A variety of other therapeutic agents may find use for administration with the modified immunoglobulins of the present invention. In one embodiment, the modified immunoglobulin is administered with an anti-angiogenic agent, which is a compound that blocks, or interferes to some degree, the development of blood vessels. The anti-angiogenic factor may, for instance, be a small molecule or a protein, for example an antibody, Fc fusion molecule, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the modified immunoglobulin is administered with a therapeutic agent that induces or enhances adaptive immune response, for example an antibody that targets CTLA-4. In an alternate embodiment, the modified immunoglobulin is administered with a tyrosine kinase inhibitor, which is a molecule that inhibits to some extent tyrosine kinase activity of a tyrosine kinase. In an alternate embodiment, the modified immunoglobulins of the pre-sent invention are administered with a cytokine. By "cytokine" as used herein is meant a generic term for proteins released by one cell population that act on another cell as intercellular mediators including chemokines.

Pharmaceutical compositions are contemplated wherein modified immunoglobulins of the present invention and one or more therapeutically active agents are formulated. Stable formulations of the antibody variants of the present invention are prepared for storage by mixing said immunoglobulin having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. The formulations to be used for in vivo administration are preferably sterile. This is readily accomplished by filtration through sterile filtration membranes or other methods. The modified immunoglobulins and other therapeutically active agents disclosed herein may also be formulated as immunoliposomes, and/or entrapped in microcapsules Administration of the pharmaceutical composition comprising a modified immunoglobulin of the present invention, preferably in the form of a sterile aqueous solution, may be done in a variety of ways, including, but not limited to, orally, subcutaneously, intravenously, intranasally, intraotically, transdermally, mucosal, topically (e.g., gels, salves, lotions, creams, etc.), intraperitoneally, intramuscularly, intrapulmonary (e.g., AERx™ inhalable technology commercially available from Aradigm, or Inhance™ pulmonary delivery system commercially available from Inhale Therapeutics), vaginally, parenterally, rectally, or intraocularly.

As used herein, the term "specifically binds" refers to a binding reaction which is determinative of the cognate ligand of interest in a heterogeneous population of molecules. Thus, under designated conditions (e.g. immunoassay conditions in the case of an immunoglobulin), the specified antibody binds to its particular "target" and does not bind in a significant amount to other molecules present in a sample. Comparable to CDRs of antibodies the modified structural loop regions are antigen-, structure- or molecule-binding protein moieties and not antigens as such.

Another aspect of the present invention relates to a method for manufacturing an immunoglobulin or a pharmaceutical preparation thereof comprising at least one modification in a structural loop region of said immunoglobulin and determining the binding of said immunoglobulin to an epitope of an antigen, wherein the unmodified immunoglobulin does not significantly bind to said epitope, comprising the steps of:
  providing a nucleic acid encoding an immunoglobulin comprising at least one loop region,
- modifying at least one nucleotide residue of at least one of said loop regions,
- transferring said modified nucleic acid in an expression system,
- expressing said modified immunoglobulin,
- contacting the expressed modified immunoglobulin with an epitope,
- determining whether said modified immunoglobulin binds to said epitope, and
- providing the modified immunoglobulin binding to said epitope and optionally finishing it to a pharmaceutical preparation.

In a preferred embodiment the immunoglobulin according to the invention is a bispecific antibody or a bispecific single chain antibody. Further preferred is that the immunoglobulin comprises a bispecific domain or a part thereof including a minidomain.

In particular the present invention relates to a method for manufacturing a multi-specific immunoglobulin binding specifically to at least one first molecule or a pharmaceutical preparation thereof comprising at least one modification in at least one structural loop region of said immunoglobulin and determining the specific binding of said at least one loop region to at least one second molecule, which is an antigen such as selected from the group consisting of allergens, tumor associated antigens, self antigens, enzymes, bacterial antigens, fungal antigens, protozooal antigens and viral antigens, wherein the immunoglobulin containing an unmodified structural loop region does not specifically bind to said at least one second molecule, comprising the steps of:

- providing a nucleic acid encoding an immunoglobulin binding specifically to at least one first molecule comprising at least one structural loop region,
- modifying at least one nucleotide residue of at least one of said loop regions encoded by said nucleic acid,
- transferring said modified nucleic acid in an expression system,
- expressing said modified immunoglobulin,
- contacting the expressed modified immunoglobulin with said at least one second molecule, and
- determining whether said modified immunoglobulin binds specifically to the second molecule and
- providing the modified immunoglobulin binding specifically to said at least one second molecule and optionally finishing it to a pharmaceutical preparation.

The engineering of more than one specificity into a member of a specific binding pair is preferred (Kufer et al. (2004) Trends in Biotechnology vol. 22 pages 238-244).

Numerous attempts have been made to produce multi-specific, e.g. bispecific, monoclonal antibodies or antibody fragments. One problem in the production of bispecific antibodies made of two different polypeptide chains (heavy and light chain) is the necessity to express four different chains (two heavy and two light chains) in one cell resulting in a number of various combinations of molecules which have to be separated from the desired bispecific molecule in the mixture. Due to their similarity the separation of these molecules is difficult and expensive. A number of techniques have been employed to minimize the occurrence of such unwanted pairings (Carter (2001) Journal of Immunological Methods, vol 248, pages 7-15)

One solution to the problem is the production of one polypeptide chain with two specificities, like e.g. two scFvs linked to each other or the production of so-called diabodies. Such molecules have been shown to be far away from the fold of a natural molecule and are notoriously difficult to produce (Le-Gall et al. (2004) Protein Engineering, Design & Selection vol 17 pages 357-366).

Another problem of the current design of bispecific antibodies is the fact that even if the parent antibodies are bivalently binding to their respective binding partner (e.g. IgG), the resulting bispecific antibody is monovalent for each of the respective binding partner.

The preferred multi-specific molecules of the present invention solve these problems: Expression of a bispecific molecule as one polypeptide chain is possible (a modified Ig domain with two binding specificities, see example section), which is easier to accomplish than the expression of two antibody polypeptide chains (Cabilly et al. Proc. Natl. Acad. Sci. USA 81:3273-3277 (1984)).

It can also be produced as an antibody like molecule (i.e. made of two polypeptide chains, either homodimeric or heterodimeric), due to the fact that the second specificity is located in the non-variable part of the molecule there is no need for two different heavy chains or different light chains. Thus, there is no possibility of wrong pairing of the two chains.

An antibody of the present invention may consist of a heavy chain and a light chain, which form together a variable region binding to a specific binding partner by a first specificity. The second specificity may be formed by a modified loop of any of the structural loops of either the heavy chain or the light chain. The binding site may also be formed by more than one non-CDR loops which may be structurally neighboured (either on the heavy chain or on the light chain or on both chains).

The modified antibody or derivative may be a complete antibody or an antibody fragment (e.g. Fab, CH1-CH2, CH2-CH3, Fc, with or without the hinge region).

It may bind mono- or multivalently to the same or different binding partners or even with different valency for the different binding partners, depending on the design.

As there are a number of various loops available for selection and design of a specific binding site in the non-CDR regions of heavy and light chains it is possible to design antibody derivatives with even more than two specificities without the problems mentioned above.

The specific binding domains within one polypeptide chain may be connected with or without a peptide linker.

The modified structural loop region of said inventive immunoglobulin can be within the constant and/or the variable domain of said immunoglobulin. In case the modified structural loop is within the constant domain, it is preferably within CH1, CH2, CH3, CH4, Igk-C, Igl-C, or a part thereof.

According to a preferred embodiment of the present invention the immunoglobulin is of human or murine origin.

Since the modified immunoglobulin may be employed for various purposes, in particular in pharmaceutical compositions, the immunoglobulin is preferably of human or murine origin. Of course, the modified immunoglobulin may also be a humanized or chimeric immunoglobulin.

According to another preferred embodiment of the present invention the human immunoglobulin is selected from the group consisting of IgA1, IgA2, IgD, IgE, IgG1, IgG2, IgG3, IgG4 and IgM.

The murine immunoglobulin is preferably selected from the group consisting of IgA, IgD, IgE, IgG1, IgG2A, IgG2B, IgG2C, IgG3 and IgM.

The modified immunoglobulin may be derived from one of the above identified immunoglobulin classes, and structurally changed thereafter.

The immunoglobulin comprises preferably a heavy and/or light chain of the immunoglobulin or a part thereof. Either a heterodimeric or a homodimeric molecule may be preferably provided for the purpose of the invention, as well as monomeric immunoglobulins.

The modified immunoglobulin may comprise a heavy and/or light chain, and at least one variable and/or constant domain.

The immunoglobulin according to the present invention comprises preferably at least one constant and/or at least one variable domain of the immunoglobulin or a part thereof including a minidomain.

A constant domain is an immunoglobulin fold unit of the constant part of an immunoglobulin molecule, also referred to as a domain of the constant region (e.g. CH1, CH2, CH3, CH4, Ck, Cl).

A variable domain is an immunoglobulin fold unit of the variable part of an immunoglobulin, also refered to as a domain of the variable region (e.g. Vh, Vk, Vl, Vd)

A preferred immunoglobulin according to the invention consists of a constant domain selected from the group consisting of CH1, CH2, CH3, CH4, Igk-C, Igl-C, or a part or combinations thereof, including a mini-domain, with at least one loop region, and is characterised in that said at least one loop region comprises at least one amino acid modification forming at least one modified loop region, wherein said at least one modified loop region binds specifically to at least one epitope of an antigen.

The modified immunoglobulin according to the present invention may comprise one or more constant domains (e.g. at least two, three, four, five, six, ten domains). If more than one do-main is present in the modified immunoglobulin these domains may be of the same type or of varying types (e.g. CH1-CH1-CH2, CH3-CH3, Fc region, (CH2)2-(CH3) 2). Of course also the order of the single domains may be of any kind (e.g. CH1-CH3-CH2, CH4-CH1-CH3-CH2).

According to another preferred embodiment of the present invention the modified loop regions of CH1, CH2, CH3 and CH4 comprise amino acids 7 to 21, amino acids 25 to 39, amino acids 41 to 81, amino acids 83 to 85, amino acids 89 to 103 and amino acids 106 to 117.

According to another preferred embodiment of the present invention the amino acid residues of positions 15 to 17, 29 to 34, 85.4 to 85.3, 92 to 94, 97 to 98 and/or 108 to 110 of CH3 are modified.

The loop regions of Igk-C and Igl-C of human origin comprise preferably amino acids 8 to 18, amino acids 27 to 35, amino acids 42 to 78, amino acids 83 to 85, amino acids 92 to 100, amino acids 108 to 117 and amino acids 123 to 126.

The loop regions of Igk-C and Igl-C of murine origin comprise preferably amino acids 8 to 20, amino acids 26 to 36, amino acids 43 to 79, amino acids 83 to 85, amino acids 90 to 101, amino acids 108 to 116 and amino acids 122 to 125.

According to a specific embodiment the immunoglobulin according to the invention may contain a modification within the variable domain, which is selected from the group of VH, Vkappa, Vlambda, VHH and combinations thereof. More specifically, they comprise at least one modification within amino acids 7 to 21, amino acids 25 to 39, amino acids 41 to 81, amino acids 83 to 85, amino acids 89 to 103 or amino acids 106 to 117, where the numbering of the amino acid position of the domains is that of the IMGT.

Another preferred immunoglobulin according to the invention consists of a variable domain of a heavy or light chain, or a part thereof including a minidomain, with at least one loop region, preferably a structural loop region, and is characterised in that said at least one loop region comprises at least one amino acid modification forming at least one modified loop region, wherein said at least one modified loop region binds specifically to at least one epitope of an antigen.

In an alternative embodiment, the immunoglobulin according to the invention is characterised in that the loop regions of VH or Vkappa or Vlambda of human origin comprise at least one modification within amino acids 8 to 20, amino acids 44 to 50, amino acids 67 to 76 and amino acids 89 to 101, most preferably amino acid positions 12 to 17, amino acid positions 45 to 50, amino acid positions 69 to 75 and amino acid positions 93 to 98, where the numbering of the amino acid position of the domains is that of the IMGT.

The structural loop regions of the variable domain of the immunoglobulin of human origin, as possible selected for modification purposes according to the invention comprise preferably amino acids 8 to 20, amino acids 44 to 50, amino acids 67 to 76 and amino acids 89 to 101.

According to a preferred embodiment of the present invention the structural loop regions of the variable domain of the immunoglobulin of murine origin as possible selected for modification purposes according to the invention comprise amino acids 6 to 20, amino acids 44 to 52, amino acids 67 to 76 and amino acids 92 to 101.

The immunoglobulin according to the invention is preferably also of camel origin. Camel antibodies comprise only one heavy chain and have the same antigen affinity as normal antibodies consisting of light and heavy chains. Consequently camel antibodies are much smaller than, e.g., human antibodies, which allows them to penetrate dense tissues to reach the antigen, where larger proteins cannot. Moreover, the comparative simplicity, high affinity and specificity and the potential to reach and interact with active sites, camel's heavy chain antibodies present advantages over common antibodies in the design, production and application of clinically valuable compounds.

The immunoglobulin of camel or camelid origin comprises preferably at least one constant domain selected from the group consisting of CH1, CH2 and CH3. According to a preferred embodiment of the present invention the loop regions of CH1, CH2 and CH3 of the camel immunoglobulin comprise amino acids 8 to 20, amino acids 24 to 39, amino acids 42 to 78, amino acids 82 to 85, amino acids 91 to 103 and amino acids 108 to 117.

Even more specified, the immunoglobulin loop regions of VH of murine origin comprise at least one modification within amino acids 6 to 20, amino acids 44 to 52, amino acids 67 to 76 and amino acids 92 to 101, where the numbering of the amino acid position of the domains is that of the IMGT. The modified loop regions of a VHH of camelid origin preferably comprise at least one modification within amino acids 7 to 18, amino acids 43 to 55, amino acids 68 to 75 and amino acids 91 to 101, where the numbering of the amino acid position of the domains is that of the IMGT.

The above identified amino acid regions of the respective immunoglobulins are loop regions specified to be suitable for modification purposes according to the invention.

Yet another aspect of the present invention relates to a method for specifically binding and/or detecting a molecule comprising the steps of:
  (a) contacting a modified immunoglobulin according to the present invention or a modified immunoglobulin obtainable by a method according to the present invention with a test sample suspected to contain said molecule, and
  (b) detecting the potential formation of a specific immunoglobulin/molecule complex.

Another aspect of the present invention relates to a method for specifically isolating a molecule comprising the steps of:
  (a) contacting a modified immunoglobulin according to the present invention or a modified immunoglobulin obtainable by a method according to the present invention with a sample containing said molecule,
  (b) separating the specific immunoglobulin/molecule complex formed, and
  (c) optionally isolating the molecule from said complex.

The immunoglobulins according to the present invention may be used to isolate specifically molecules from a sample. If multi-specific immunoglobulins are used more than one molecules may be isolated from a sample. It is especially advantageous using modified immunoglobulins in such methods because it allows, e.g., to generate a matrix having a homogeneous surface with defined amounts of binding partners (i.e. Modified immunoglobulins) immobilised thereon which able to bind to the molecules to be isolated. In contrast thereto, if mono-specific binding partners are used no homogeneous matrix can be generated because the single binding partners do not bind with the same efficiency to the matrix.

Another aspect of the present invention relates to a method for targeting a compound to a target comprising the steps of:
  (a) contacting a modified immunoglobulin according to the present invention or a modified immunoglobulin obtainable by a method according to the present invention capable to specifically bind to said compound,
  (b) delivering the immunoglobulin/compound complex to the target.

Modified immunoglobulins according to the present invention may be used to deliver at least one compound bound to the CDRs and/or modified loop regions to a target. Such immunoglobulins may be used to target therapeutic substances to a preferred site of action in the course of the treatment of a disease.

Another aspect of the present invention relates to the use of an immunoglobulin according to the present invention or obtainable by a method according to the present invention for the preparation of a protein library of immunoglobulins. Further libraries according to the invention not just contain a variety of proteins or fusion proteins, genetic packages, but also precursors of proteins, nucleic acids, ribosomes, cells, virus, phages, and other display systems which express information encoding the proteins and/or the proteins as such.

Another aspect of the present invention relates to a protein library comprising an immunoglobulin according to the present invention or obtainable by the method according to the present invention.

Preferred methods for constructing said library can be found above and in the examples. The library according to the present invention may be used to identify immunoglobulins binding to a distinct molecule.

In particular the present invention relates to the use of a protein library comprising an immunoglobulin according to the present invention or obtainable by the method according to the present invention for the design of immunoglobulin derivatives.

An existing immunoglobulin can be changed to introduce antigen binding sites into any domain or minidomain by using a protein library of the respective domain of at least 10, preferably 100, more preferably 1000, more preferably 10000, more preferably 100000, most preferably more than 1000000 variant domains or minidomains with at least one modified loop, in particular one or more structural loops. The number of members of a library can even be higher, in most cases up to 10e12, with some display systems, such as ribosomal display the number can even be higher than that.

The library is then screened for binding to the specific antigen. After molecular characterization for the desired properties the selected domain or minidomain is cloned into the original immunoglobulin by genetic engineering techniques so that it replaces the wild type region. Alternatively, only the DNA coding for the loops or coding for the mutated amino acids may be exchanged to obtain an immunoglobulin with the additional binding site for the specific antigen.

The choice of the site for the mutated, antigen-specific structural loop is dependent on the structure of the original immunoglobulin and on the purpose of the additional binding site. If, for example, the original molecule is a complete immunoglobulin which needs to have inserted an additional antigen binding site without disturbance of the effector function, the loops to be modified would be selected from domains distant from CH2 and CH3 which are the natural binding partners to Fc-effector molecules. If the original immunoglobulin is a Fab fragment, modification of loops in constant domains of the light chains or the heavy chains or the respective variable domains is possible. To generate a library one may prepare libraries of mutant original molecules which have mutations in one ore more structural loops of one or more domains. The selection with complete mutated original molecules may have some advantages as the selection for antigen binding with a modified structural loop will deliver the sterically advantageous modifications if tested also for the other properties the mutated immunoglobulin should show. In particular an Fc library is preferred, e.g. with binding sites in the C-terminal loop region.

The size requirement (i.e. the number of variant proteins) of a protein library of a mutated domain or a minidomain or a fusion molecule of a domain is dependent on the task. In general, a library to generate an antigen binding site de novo needs to be larger than a library used to further modify an already existing engineered antigen binding site made of a modified structural loop (e.g. for enhancing affinity or changing fine specificity to the antigen).

The present invention also relates to an immunoglobulin library or a nucleic acid library comprising a plurality of immunoglobulins, e.g. a constant or variable domain, a minidomain and/or at least one structural loop region contained in a mini-domain, or nucleic acid molecules encoding the same. The library contains members with different modifications, wherein the plurality is defined by the modifications in the at least one structural loop region. The nucleic acid library preferably includes at least 10 different members with a difference in the nucleotide sequence to obtain at least one different amino acid (resulting in one amino acid exchange) and more preferably includes at least 100, more preferably 1000 or 10000 different members (e.g. designed by randomisation strategies or combinatory techniques). Even more diversified individual member numbers, such as at least 1000000 or at least 10000000 are also preferred.

A further aspect of the invention is the combination of two different immunoglobulins, domains or minidomains selected from at least two libraries according to the invention in order to generate multispecific immunoglobulins. These selected specific immunoglobulins may be combined with each other and with other molecules, similar to building blocks, to design the optimal arrangement of the domains or minidomains to get the desired properties. For example, a molecule based on Fc can be used as such, with antigen-binding properties, as a carrier for other binding motifs or as a building block to build an immunoglobulin with constant or variable domains, or else combined with constant domains only, such as multimeric Fc molecules, preferably with 2, 3, or 4 antigen binding sites.

Furthermore, one or more modified immunoglobulins according to the invention may be introduced at various or all the different sites of a protein possible without destruction of the structure of the protein. By such a "domain shuffling" technique new libraries are created which can again be selected for the desired properties.

Preferably, the immunoglobulin according to the present invention is composed of at least two immunoglobulin domains, or a part thereof including a minidomain, and each domain contains at least one antigen binding site.

Also preferred is an immunoglobulin according to the invention, which comprises at least one domain of the constant region and/or at least one domain of the variable region of the immunoglobulin, or a part thereof including a minidomain. Thus, a variable domain, which is for example modified in the C-terminal region, or the variable domain linked to a modified CH1 region, for instance a modified CH1 minidomain, is one of the preferred embodiments.

The preferred library contains immunoglobulins according to the invention, selected from the group consisting of domains of an immunoglobulin, minidomains or derivatives thereof.

A preferred embodiment of the present invention is a binding molecule for an antigen (antigen binding molecule) comprising at least one immunoglobulin domain and a structural loop region modified according to the present invention to bind to the antigen, wherein said binding molecule does not comprise variable domains of an antibody. It may comprise other parts useable for antibody activities (e.g. such as natural or modified effector regions (sequences); however, it lacks the "natural" binding region of antibodies, i.e. the variable domains or CDR loops, including VFR loops within the CDR region, in their naturally occurring position. These antigen binding molecules according to the present invention have the advantages described above for the present molecules, yet without the specific binding activity of antibodies mediated by CDR loops; however with a newly introduced specific binding activity in the structural loop region.

Preferably, these antigen binding molecules according to the present invention comprise CH1, CH2, CH3, CH4, Igk-C, Igl-C and combinations thereof; said combinations comprising at least two, preferably at least four, especially at least six constant domains and at least one structural loop or loop region modified according to the present invention. Preferably these structural loop regions are either connected via structural loop region modified according to the present invention or the structural loops being naturally present between such two constant domains. An embodiment of these antigen binding molecules according to the present invention consists of the Fc region of an antibody with at least one modification in a structural loop according to the present invention. Also for the antigen binding molecules according to the present invention it is preferred that the new antigen binding sites in the structural loops are introduced by randomising technologies, i.e. by exchanging one or more amino acid residues of the loop by randomisation techniques or by introducing randomly generated inserts into such structural loops. Alternatively preferred is the use of combinatorial approaches. Preferably the antigen binding sites in the modified structural loops are selected from suitable libraries.

According to another aspect, the present invention relates to a modified immunoglobulin having an antigen binding site to provide a specificity foreign to the unmodified immunoglobulin and incorporated in one or more structural loops. The term "foreign" means that the antigen is not recognized by the specific CDR binding region or other natural or intrinsic binding regions of the immunoglobulin. A foreign binding partner, but not the natural binding partner of an immunoglobulin, may thus be bound by the newly formed antigen binding site of a structural loop. This means that a natural binding partner, such as a an Fc-receptor or an effector of the immune system, is not considered to be bound by the antigen binding site foreign to the unmodified immunoglobulin.

Preferred immunoglobulins according to the present invention comprise at least two antigen binding sites, the first site binding to a first epitope, and the second site binding to a second epitope.

According to a preferred embodiment, the present immunoglobulin comprises at least two loop regions, the first loop region binding to a first epitope, and the second loop region binding to a second epitope. Either the at least first or at least second loop region or both may contain a structural loop. The immunoglobulins according to the present inventions include the fragments thereof known in the art to be functional which contain the essential elements according to the present invention: the structural loop or loop region modified according to the present invention.

The preferred immunoglobulin according to the invention comprises a domain that has at least 50% homology with the unmodified domain.

The term "homology" indicates that polypeptides have the same or conserved residues at a corresponding position in their primary, secondary or tertiary structure. The term also extends to two or more nucleotide sequences encoding the homologous polypeptides.

"Homologous immunoglobulin domain" means an immunoglobulin domain according to the invention having at least about 50% amino acid sequence identity with regard to a full-length native sequence immunoglobulin domain sequence or any other fragment of a full-length immunoglobulin domain sequence as disclosed herein. Preferably, a homologous immunoglobulin domain will have at least about 50% amino acid sequence identity, preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90% amino acid sequence identity, more preferably at least about 95% amino acid sequence identity to a native immunoglobulin domain sequence, or any other specifically defined fragment of a full-length immunoglobulin domain sequence as disclosed herein.

"Percent (%) amino acid sequence identity" with respect to the immunoglobulin domain sequences identified herein is defined as the percentage of amino acid residues in a candidate sequence that are identical with the amino acid residues in the specific immunoglobulin domain sequence, after aligning the sequence and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Percent (%) amino acid sequence identity values may be obtained as de-scribed below by using the WU-BLAST-2 computer program (Altschul et al., Methods in Enzymology 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the immunoglobulin domain of interest having a sequence derived from the native immunoglobulin domain and the comparison amino acid sequence of interest (i.e., the sequence against which the immunoglobulin domain of interest is being compared which may be the unmodified immunoglobulin domain) as determined by WU-BLAST-2 by (b) the total number of amino acid residues of the non-randomized parts of the immunoglobulin do-main of interest. For example, in the statement "a polypeptide comprising an amino acid sequence A which has or having at least 80% amino acid sequence identity to the amino acid sequence B", the amino acid sequence A is the comparison amino acid sequence of interest and the amino acid sequence B is the amino acid sequence of the immunoglobulin domain of interest.

Another aspect of the present invention relates to a kit of binding partners containing
  (a) a modified immunoglobulin having an antigen binding site foreign to the immunoglobulin incorporated in one or more structural loops, and
  (b) a binding molecule containing an epitope of said antigen.

Such a binding molecule of this kit according to the present invention may be used as a capturing agent for identifying the binding specificity of the modified immunoglobulin according to the present invention. By using the binding molecule of this kit according to the present invention, the potency of the modified immunoglobulins according to the present invention may be determined.

Potency as defined here is the binding property of the modified molecule to its antigen. The binding can be determined quantitatively and/or qualitatively in terms of specificity and/or affinity and/or avidity as used for quality control purposes.

The binding properties of the molecules according to the invention obtained upon modification may further be tuned by standard techniques, such as affinity maturation. Thereby the nucleotide sequence within or surrounding the antigen binding site is further exchanged for modulating the binding properties.

Moreover, the binding molecule of a kit according to the present invention may be used for selecting the modified immunoglobulin with the appropriate potency according to the present invention from a library consisting of at least 10, preferably at least 100, more preferably at least 1000, more preferred at least 10000, especially at least 100000 immunoglobulins with different modifications in the structural loops.

Examples have shown that one of the key features is engineer those immunoglobulin domains or regions which are not normally involved in the desirable intrinsic functions of a antibody, such as antigen binding. Thus, modifying in regions other than the CDR region, including those loops adjacent to the CDR loops, of an antibody would preserve its antigen binding function. It was observed that the specific fold of immunoglobulin domains allows the introduction of random mutations in regions which are structurally analogous to the CDRs but different in position and sequence. The regions identified by the present invention are, like CDRs, loop regions connecting the beta strands of the immunoglobulin fold.

More specifically, it is described herein that by introducing mutations, e.g. random mutations in the loops connecting beta strands A-B and E-F of a human IgG1 CH3 domain, mutated CH3 domains were selected that bind specifically to either Toll like receptor 9-peptide (TLR-9) or to hen egg lysozyme, which are a peptide and a protein, respectively, that are not normally recognized and bound by human CH3 domains of IgG1. The mutations introduced by us include mutations in which selected amino acid residues in the wildtype sequence were replaced by randomly chosen residues, and they also include insertions of extra amino acid residues in the loops mentioned above.

By analogy the immunoglobulin domains from any class of immunoglobulins and from immunoglobulins from any species are amenable to this type of engineering. Furthermore not only the specific loops targeted in the present invention can be manipulated, but any loop connecting beta strands in immunoglobulin domains can be manipulated in the same way.

Engineered immunoglobulin domains from any organism and from any class of immunoglobulin can be produced according to the present invention either as such (as single domains), or as part of a larger molecule. For example, they can be part of an intact immunoglobulin, which accordingly would have its "normal" antigen binding region formed by the 6 CDRs and the new, engineered antigen binding region. Like this, a multi-specific, e.g. bispecific, immunoglobulin could be generated. The engineered immunoglobulin domains can also be part of any fusion protein. The use of these engineered immunoglobulin domains is in the general field of the use of immunoglobulins.

Except where indicated otherwise all numbering of the amino acid sequences of the immunoglobulins is according to the IMGT numbering scheme (IMGT, the international ImMunoGeneTics information see SYSTEM at IMGT. CINES.FR; the URL imgt.cines.fr; Lefranc et al., 1999, Nucleic Acids Res. 27: 209-212; Ruiz et al., 2000 Nucleic Acids Res. 28: 219-221; Lefranc et al., 2001, Nucleic Acids Res. 29: 207-209; Lefranc et al., 2003, Nucleic Acids Res. 31: 307-310; Lefranc et al., 2005, Dev Comp Immunol 29:185-203).

```
SEQ ID No. 21
PREPQVYTLPPSRDELTKNQVSLTCLVKGF
YPSDIAVEWESNGQPENNYKTTPPVLDSDG
SFFLYSKLTVDKSRWQQGNVFSCSVMHEAL
HNHYTQKSLSLSPGKAAA

SEQ ID No. 22
ccatggcccc ccgagaacca caggtgtaca ccctgccccc
atcccgtgac gagctcnnsn nsnnscaagt
cagcctgacc tgcctggtca aaggcttcta tcccagcgac
atcgccgtgg agtgggagag caatgggcag
ccggagaaca actacaagac cacgcctccc gtgctggact
ccgacggctc cttcttcctc tacagcaagc
ttaccgtgnn snnsnnsagg tggnnsnnsg ggaacgtctt
ctcatgctcc gtgatgcatg aggctctgca
caaccactac acacagaaga gcctctccct gtctccgggt
aaagcggccg ca
//

SEQ ID No. 23
MAPREPQVYTLPPSRDELXXXQVSLTCLVK
GFYPSDIAVEWESNGQPENNYKTTPPVLDS
DGSFFLYSKLTVXXXRWXXGNVFSCSVMHE
ALHNHYTQKSLSLSPGKAAA

SEQ ID No. 24
cttgccatgg ccccccgaga accacaggtg tac

SEQ ID No. 25
agtcgagctc gtcacgggat gggggcaggg

SEQ ID No. 26
gtacgagctc nnsnnsnnsc aagtcagcct gacctgcctg g

SEQ ID No. 27
tgccaagctt gctgtagagg aagaaggagc cg

SEQ ID No. 28
tgccaagctt accgtgnnsn nsnnsaggtg gnnsnnsggg
aacgtcttct catgctccg

SEQ ID No. 29
agttgcggcc gctttacccg gagacaggga gag

SEQ ID No. 30
MAPREPQVYTLPPSRDELXXXQVSLTCLVK
GFYPSDIAVEWESNGQPENNYKTTPPVLDS
DGSFFLYSKLTVXXXXXXRWXXGNVFSCSV
MHEALHNHYTQKSLSLSPGKAAA
```

SEQ ID No. 31
```
ccatggcccc ccgagaacca caggtgtaca ccctgccccc atcccgtgac gagctcnnsn nsnnscaagt cagcctgacc tgcctggtca aaggcttcta tcccagcgac atcgccgtgg agtgggagag caatgggcag ccggagaaca actacaagac cacgcctccc gtgctggact ccgacggctc cttcttcctc tacagcaagc ttaccgtgnn snnsnnsnns nnsnnsaggt ggnnsnnsgg gaacgtcttc tcatgctccg tgatgcatga ggctctgcac aaccactaca cacagaagag cctctccctg tctccgggta aagcggccgc a
```

SEQ ID No. 32
```
tgccaagctt accgtgnnsn nsnnsnnsnn snnsaggtgg nnsnnsggga acgtcttctc atgctccg
```

SEQ ID No. 33
```
MAPREPQVYTLPPSRDELXXXQVSLTCLVK

GFYPSDIAVEWESNGQPENNYKTTPPVLDS

DGSFFLYSKLTVXXXXXXXXRWXXGNVFSCSV

MHEALHNHYTQKSLSLSPGKAAA
```

SEQ ID No. 34
```
ccatggcccc ccgagaacca caggtgtaca ccctgccccc atcccgtgac gagctcnnsn nsnnscaagt cagcctgacc tgcctggtca aaggcttcta tcccagcgac atcgccgtgg agtgggagag caatgggcag ccggagaaca actacaagac cacgcctccc gtgctggact ccgacggctc cttcttcctc tacagcaagc ttaccgtgnn snnsnnsnns nnsnnsnnsn nsaggtggnn snnsgggaac gtcttctcat gctccgtgat gcatgaggct ctgcacaacc actacacaca gaagagcctc tccctgtctc cgggtaaagc ggccgca
```

SEQ ID No. 35
```
tgccaagctt accgtgnnsn nsnnsnnsnn snnsnnsnns aggtggnnsn nsgggaacgt cttctcatgc tccg
```

Example 1: Construction of the CH3 Library and Phage Surface Display

The crystal structure of an IgG1 Fc fragment, which is published in the Brookhaven Database as entry 1OQO.pdb was used to aid in the design of the mutated CH3 domain.

The sequence which was used as the basis for construction of the CH3 library is given in SEQ ID No. 21. In this sequence, the first amino acid corresponds to Proline 343 of chain A of Brookhaven database entry loqo.pdb. The last residue contained in loqo.pdb is Serine 102 of SEQ ID No. 21. After detailed analysis of the structure of loqo.pdb and by visual inspection of the residues forming the loops which connect the beta strands, it was decided to randomize residues 17, 18 and 19, which are part of the loop connecting beta strand A-B as well as 71, 72, 73, 76, and 77, which are part of the loop connecting beta strand E-F of SEQ ID No. 21. The engineered gene was produced by a series of PCR reactions followed by ligation of the resulting PCR products. To facilitate ligation, some of the codons of the nucleotide sequence coding for SEQ ID No. 21 were modified to produce restriction sites without changing the amino acid sequences (silent mutations). For insertion into the cloning vector pHEN1 (Nucleic Acids Res. 1991 Aug. 11; 19(15): 4133-7. Multi-subunit proteins on the surface of filamentous phage: methodologies for displaying antibody (Fab) heavy and light chains. Hoogenboom H R, Griffiths A D, Johnson K S, Chiswell D J, Hudson P, Winter G.) in frame with the pelB secretion signal, extra nucleotide residues encoding Met-Ala were attached at the 5' end of the sequence to create an NcoI restriction site. For the randomized residues, the codon NNS (IUPAC code, where S means C or G) was chosen which encodes all 20 naturally occurring amino acids, but avoids 2 out of 3 stop codons. The engineered sequence is given as a nucleotide sequence in SEQ ID No. 22 and as an amino acid sequence in SEQ ID No. 23. The Letter X in SEQ ID No. 23 denotes randomized amino acid residues. The sequences of the PCR primers used for assembly of the mutated CH3 domain are given in SEQ ID No. 24 through 29.

cDNA of the heavy chain of the human monoclonal antibody 3D6 (Felgenhauer M, Kohl J, Rüker F. Nucleotide sequences of the cDNAs encoding the V-regions of H- and L-chains of a human mono-lonal antibody specific to HIV-1-gp41. Nucleic Acids Res. 1990 Aug. 25; 18(16):4927) were used as template for the PCR reactions. The 3 PCR products were digested with SacI and/or HindIII respectively and ligated together. The ligation product was further digested with NcoI and Not I and ligated into the surface display phagemid vector pHen1, which had previously been digested with NcoI and NotI. A number of selected clones were controlled by restriction analysis and by DNA sequencing and were found to contain the insert as planned, including the correctly inserted randomized sequences. For the following steps of phage preparation, standard protocols were followed. Briefly, the ligation mixture was transformed into E. coli TG1 cells by electroporation. Subsequently, phage particles were rescued from E. coli TG1 cells with helper phage M13-KO7. Phage particles were then precipitated from culture supernatant with PEG/NaCl in two steps, dissolved in water and used for selection by panning or, alternatively, they were stored at minus 80° C.

Example 2: Construction of the CH3+3 Library

This library was constructed and cloned in the same way as the CH3 library. The amino acid sequence of the construct is given in SEQ ID No. 30, the corresponding nucleotide sequence in SEQ ID No. 31, and the primers used for construction were SEQ ID No. 24-27, SEQ ID No. 29 and SEQ ID No. 32.

Example 3: Construction of the CH3+5 Library

This library was constructed and cloned in the same way as the CH3 library. The amino acid sequence of the construct is given in SEQ ID No. 33, the corresponding nucleotide sequence in SEQ ID No. 34, and the primers used for construction were SEQ ID No. 24-27, SEQ ID No. 29 and SEQ ID No. 35.

Example 4: Construction of a CH1 Library

In the human IgG1 CH1 library, Ser93, Ser94, Ser95, Gly98, Thr99 and Gln100 were randomized and 3 random residues additionally inserted using site directed random mutagenesis. Leu96 was not mutated. In another human IgG1 CH1 library, Pro92, Ser93, Ser94, Ser95 Leu96 Thr101, Gly98, Thr99 and Gln100 were randomized and 3 random residues additionally inserted using site directed random mutagenesis. The genes coding for the libraries were cloned in frame with the pelB leader at the N-terminus and in frame with protein III from fd phage at the C-terminus using the restriction sites NcoI and NotI of the phagemid vector pHEN1. Preparation of phage particles, panning and selection of specifically binding clones were performed using standard procedures.
Library Sequence:

Nucleotide sequence of the first CH1 library:
```
  1 GCCTCCACCA AGGGCCCATC GGTCTTCCCC CTGGCACCCT CCTCCAAGAG CACCTCTGGG GGCACAGCGG CCCTGGGCTG CCTGGTCAAG GACTACTTCC
101 CCGAACCGGT GACGGTGTCG TGGAACTCAG GCGCCCTGAC CAGCGGCGTG CACACCTTCC CGGCTGTCCT ACAGTCCTCA GGACTCTACT CCCTCAGCAG
201 CGTGGTGACC GTGCCCNNSN NSNNSTTGNN NSNNSNNSNN SNNSNNSNNS ACATCTGCAA CGTGAATCAC AAGCCCAGCA ACACCAAGGT GGACAAGAAA
301 GTTGAGCCCA AATCTGCGGC CGCCCA (SEQ ID NO: 1)
```

Amino acid sequence of the first CH1 library:
MKYLLPTAAAGLLLLAAQPAMAASTKGPSVFPLAPSSKSTSGGTAALGCLVKDYFPGPVTVSWNSGALTSGVHTFPAVLQSSGLYSLSSVVTPXXXLXXXXXXXTYICNVNHKPSNTKVDK
KVEPKSAAA (SEQ ID NO:2)

Nucleotide sequence of the second CH1 library:
```
  1 GCCTCCACCA AGGGCCCATC GGTCTTCCCC CTGGCACCCT CCTCCAAGAG CACCTCTGGG GGCACAGCAG CCCTGGGCTG CCTGGTCAAG GACTACTTCC
101 CCGAACCGGT GACGGTGTCG TGGAACTCAG GCGCCCTGAC CAGCGGCGTG CACACCTTCC CGGCTGTCCT GCAGTCCTCA GGACTCTACT CCCTCAGCAG
201 CGTGGTGACC GTGNNSNNSN NSNNSNNSNN SNNSNNSNNS ACATCTGCAA CGTGAATCAC AAGCCCAGCA ACACCAAGGT GGACAAGAAA
301 GTTGAGCCCA AATCTGCGGC CGCT (SEQ ID NO: 3)
```

Amino acid sequence of the second CH1 library:
ASTKGPSVFPLAPSSKSTSGGTAALGCLVKDYFPEPVTVSWNSGALTSGVHTFPAVLQSSGLYSLSSVVTVXXXXXXXXXXXXYICNVNHKPSNTKVDKKVEPKSAAA (SEQ ID NO: 4)

Example 4: Construction of a CL Library

In the human IgG1 CL library, Ser92, Lys93, Ala94, Asp95, Glu97, Lys98 and His99 were randomized and 3 random residues additionally inserted between Ser16 and Gly17 using site directed random mutagenesis. The genes coding for the libraries were cloned in frame with the pelB leader at the N-terminus and in frame with protein III from fd phage at the C-terminus using the restriction sites NcoI and NotI of the phagemid vector pHEN1. Preparation of phage particles, panning and selection of specifically binding clones were performed using standard procedures.

Nucleotide sequence of the CL library:
```
  1  GTGGCTGCAC CATCTGTCTT CATCTTCCCG CCATCTGATG AGCAGTTGAA ATCTNNSNNS NNSGGAACTG CCTCTGTTGT GTGCCTGCTG AATAACTTCT
101  ATCCCAGAGA GGCCAAGTA CAGTGGAAGG TGGATAACGC CCTCCAATCG GGTAACTCCC AGGAGAGTGT CACAGAGCAG GACAGCAAGG ACAGCACCTA
201  CAGCCTCAGG TCGACCCTGA CGCTGNNSNN SNNSNNSTAC NNSNNSNNSA AAGTCTACGC CTGCGAAGTC ACCCATCAGG GCCTGAGCTC GCCCGTCACA
301  AAGAGCTTCAACAGGGGAGAG (SEQ ID NO: 5)
```

Amino acid sequence of the CL library:
VAAPSVFIFPPSDEQLKSXXXGTASVVCLLNNFYPREAKVQWKVDNALQSGNSGESVTEQDSKDSTYSLRSTLTLXXXXYXXXKVYACEVTHQGLSSPVTKSFNRGE (SEQ ID NO: 6)

Example 5: Panning of the CH3-Phage Library on Rp10-L Peptide 3 panning rounds were performed. Maleimide activated plates (Pierce) were coated with a synthetic peptide RpIO-L, representing a mimotope of B-cell molecular marker CD20 (Perosa et al. Ann N Y Acad Sci. (2005) 51:672-83). Its deduced amino acid sequence is as follows: ITPWPHWLERSS (SEQ ID NO:7). 200 μl of the following solution were added per well: PBS, pH=7.2, with the following concentrations of dissolved peptide:

$1^{st}$ panning round: 100 μg/ml
$2^{nd}$ panning round: 100 μg/ml
$3^{rd}$ panning round: 50 μg/ml.

Incubation was overnight at 4° C., followed by blocking with 10 μg/ml cysteine-HCl in PBS, with 200 μl per well for 2 h at room temperature.

The surface display phage library, containing equal concentration of phage from libraries CH3, CH3+3, CH3+5, and CH3+7, was then allowed to react with the bound peptide by adding phage suspension and 2% BSA-PBS up to 200 μl, followed by incubation for 45 min with shaking and 90 min without shaking at room temperature.

Unbound phage particles were washed away as follows;
after the $1^{st}$ panning round: 15×200 μl T-PBS, 5×200 μl T-PBS
after the $1^{st}$ panning round: 15×200 μl T-PBS, 10×200 μl T-PBS
after the $1^{st}$ panning round: 20×200 μl T-PBS, 20×200 μl T-PBS.

Elution of bound particles was performed by adding 200 μl per well of 0.1 M glycine, pH=2.2, and incubation with shaking for 30 min at room temperature. Subsequently, the phage suspension was neutralised by the addition of 60 μl 2M Tris-base, followed by the infection of *E. coli* TG1 cells by mixing 10 ml exponentially growing culture with 0.5 ml eluted phage and incubation for 30 min at 37°. Finally, infected bacteria were plated on TYE medium with 1% glucose and 100 μg/ml ampicillin, and incubated at 30° C. overnight.

Results of the Panning of the CH3-Phage Library on Rp10-L Peptide
Phage Titers

| Panning round | concentration Rp10-L | input (phage/ml) | output (phage/ml) |
|---|---|---|---|
| $1^{st}$ | 100 μg/ml | $2 \times 10^{14}$ | $2 \times 10^{10}$ |
| $2^{nd}$ | 100 μg/ml | $3 \times 10^{17}$ | $3 \times 10^{10}$ |
| $3^{rd}$ | 50 μg/ml | $6.02 \times 10^{14}$ | $1.5 \times 10^{10}$ |

Example 6: Cloning of Selected Clones for Soluble Expression

Altered, CH3 domain-encoding sequences, contained within eluted phage particles, were batch amplified with PCR. After restriction with NcoI and NotI, they were inserted in pNOTBAD (Invitrogen vector pBAD with subsequently inserted NotI site). After transformation into *E. coli* E104, the cells were selected on TYE medium with 1% glucose and 100 μg/ml ampicillin at 30° C.

Soluble Expression of Selected Clones and Screening

4×96 ampicilline resistant colonies were cultured in 200 μl 2×YT medium with ampicillin in microtitre plates on a shaker overnight at 30° C. They were then induced with L-arabinose added to end concentration of 0.1%. After another overnight incubation, the cells were collected by centrifuging 15 min at 2000 rpm at room temperature and their periplasma proteins were released by resuspending in 100 μl Na-borate buffer (160 mM Na-borate, 200 mM NaCl, pH=8.0) and incubation for at least 6 hours.

For screening, 4 maleimide plates were coated with 100 μg/ml solution of 50 μg/ml peptide Rp10-L, dissolved in PBS, pH=7.2, overnight at 4° C. Plates were then blocked with 10 μg/ml cysteine-HCl in PBS, with 200 μl per well for 2 h at room temperature.

Released periplasmic protein was then allowed to react with the bound peptide by adding 50 μl lysate and 50 μl 2% BSA-PBS, followed by an overnight incubation at room temperature.

Binding of the his-tagged protein was revealed by 90-min-incubation with 100 μl per well solution of antibodies against tetra-his (QIAgen), diluted 1:1000 in 1% BSA-PBS, and a 90-min-incubation with 100 μl per well solution of goat anti-mouse antibodies, labelled with HRP (Sigma), diluted 1:1000 in 1% BSA-PBS. Signals were observed after the addition of substrate OPD (3 mg/ml) in Na-citrate/phosphate buffer, pH=4.5, and 0.4 μl/ml $H_2O_2$. The reaction was stopped with by adding 100 μl 1.25 M $H_2SO_4$.

Results of Screening for Binding of Rp10-L on a Single Well Per Clone

| | Clone | | | | | | | | | | | |
|---|---|---|---|---|---|---|---|---|---|---|---|---|
| | A21 | A57 | B63 | B78 | C50 | C55 | D5 | D37 | D39 | D80 | D83 | D91 |
| $A_{492/620}$ | 0.395 | 0.039 | 0.063 | 0.075 | 0.190 | 0.045 | 0.644 | 0.071 | 0.448 | 0.077 | 0.426 | 0.142 |

Background Reaction

| Plate | $A_{492/620}$ |
|---|---|
| A | 0.027 |
| B | 0.035 |
| C | 0.037 |
| D | 0.035 |

Clones revealing a positive signal were cultured in 20 ml 2×YT with ampicillin, at 30° C. overnight. Then they were inoculated 1:20 into fresh medium, and after 3 h at 30° C. they were induced with end concentration of 0.1% L-arabinose, and allowed to express the recombinant CH3-domain overnight at 16° C. Periplasma of the expressing cells was then lysed in 1 ml of Na-borate buffer, pH=8.0, for a minimum of 6 h. Periplasmic extract was allowed to react with Rp10-L peptide and the binding was revealed exactly as described above.

Results of Screening for Binding of Rp10-L

| Rp10-L | clone | | | | | | | | | | | |
|---|---|---|---|---|---|---|---|---|---|---|---|---|
| µg/ml | A21 | A57 | 363 | 378 | C50 | C55 | D5 | D37 | D39 | D80 | D83 | D91 |
| — | 0.265 | 0.006 | 0.006 | 0.005 | 0.803 | 0.006 | 0.035 | 0.006 | 0.469 | 0.004 | 0.088 | 0.009 |
| 0.81 | 0.362 | 0.005 | 0.007 | 0.006 | 1.202 | 0.008 | 0.052 | 0.008 | 0.660 | 0.007 | 0.106 | 0.009 |
| 1.63 | 0.383 | 0.006 | 0.007 | 0.006 | 1.308 | 0.014 | 0.050 | 0.014 | 0.719 | 0.008 | 0.129 | 0.005 |
| 3.13 | 0.352 | 0.008 | 0.010 | 0.005 | 1.453 | 0.006 | 0.060 | 0.006 | 0.719 | 0.008 | 0.210 | 0.006 |
| 6.25 | 0.343 | 0.005 | 0.008 | 0.006 | 1.516 | 0.007 | 0.057 | 0.007 | 0.694 | 0.006 | 0.114 | 0.008 |
| 12.5 | 0.315 | 0.007 | 0.009 | 0.006 | 1.495 | 0.007 | 0.064 | 0.007 | 0.770 | 0.007 | 0.130 | 0.009 |
| 25.0 | 0.335 | 0.008 | 0.010 | 0.008 | 1.603 | 0.009 | 0.063 | 0.009 | 0.868 | 0.008 | 0.120 | 0.007 |
| 50.0 | 0.398 | 0.009 | 0.011 | 0.009 | 1.632 | 0.009 | 0.070 | 0.009 | 0.765 | 0.008 | 0.125 | 0.008 |

Cloning of Selected Clones for Soluble Expression in pET27b

Altered CH3 domain-encoding sequences, contained within clones that produced a significant signal on binding to Rp10-L, were amplified with PCR. After restriction with NcoI and NotI, they were inserted in pET27b (Novagen). After transformation into *E. coli* BL21 (0E3), transformed cells were selected on TYE medium with 1% glucose and 50 µg/ml kanamycin at 30° C.

Clones revealing a positive signal were cultured in 20 ml M9ZB medium with 2% glucose and kanamycin, at 30° C. overnight. Then they were inoculated 1:20 into fresh medium, and after 3 h at 30° C. they were induced with medium containing 1% glycerin instead of glucose, kanamycin and 1 mM IPTG, and allowed to express the recombinant CH3-domain overnight at 16° C. Periplasma of the expressing cells was then lysed in 1 ml of Na-borate buffer, pH=8.0, for a minimum of 6 h. Periplasmic extract was analysed for the presence of recombinant protein with western blotting and detection with anti tetra-his antibodies (QIAgen).

Nucleotide Sequences and Inferred Protein Sequences of CD-20 Binding Clones

| clone | 1$^{st}$ group | 2$^{nd}$ group | 3$^{rd}$ group | source library |
|---|---|---|---|---|
| A21 | VDG | PWGPRD (SEQ ID NO: 8) | WP | CH3 + 3 |
| C50* | LTH | ALCRWF (SEQ ID NO: 9) | VQ | CH3 + 3 |
| D5 | ALR | FCGGVV (SEQ ID NO: 10) | GL | CH3 + 3 |
| D39 | GWW | QQKPFA (SEQ ID NO: 11) | TD | CH3 + 3 |
| D83 | APP | DLVHVA (SEQ ID NO: 12) | MV | CH3 + 3 |

*an insertion of 2 nucleotides in the 2$^{nd}$ group of mutated residues causes an insertion of G between otherwise constant residues R and W separating 2$^{nd}$ and 3$^{rd}$ group of mutated residues.

Protein Sequence of CD20 Specific CH3+3 Library Clone D83 (IMGT Numbering)

```
                                                   15-17
                                                   92-94
MAPREPQVYTLPPSRDEL APPQVSLTCLVKGFYPSDIAVEWESNGQPENNYKTTPPVLDSDGSFFLYSKLTV
DLV 97-98
HVARWMVGNVFSCSVMHEALENHYTQKSLSLSPGKAAA (SEQ ID NO: 13)
```

Analysis of Binding of CD-20, Expressed on Cells, Using FACS

Approximately $10^5$ Daudi cells were washed with PBS (800 rpm, 5 min, room temperature) and the recombinant CH3 domain in 1% BSA-PBS was allowed to bind for 2h on ice. Cells were washed again with PBS and the allowed to react with 2 µg/ml anti penta His-Alexa fluor 488 antibody (QIAgen), diluted in 1% BSA-PBS, for 30 min on ice. After washing, the cells were analysed in FACS. Unlabelled cells, wild-type CH3 domain and cell line K562 were used as controls.

Example 7: Isolation of CH1-Mutant Proteins Binding CD20 Antigen 3 panning rounds were performed. Maleimide activated plates (Pierce) were coated with a synthetic peptide, representing a mimotope of B-cell molecular marker CD20. 200 µl of the following solution were added per well: PBS, pH-7.2, with the following concentrations of dissolved peptide:

$1^{st}$ panning round: 100 µg/ml
$2^{nd}$ panning round: 100 µg/ml
$3^{rd}$ panning round: 50 µg/ml.

Incubation was overnight at 4° C., followed by blocking with 10 µg/ml cysteine-HCl in PBS, with 200 µl per well for 2 h at room temperature.

The surface display phage library, displaying mutated CH1 domain, was then allowed to react with the bound peptide by adding phage suspension and 2% BSA-PBS up to 200 µl, followed by incubation for 45 min with shaking and 90 min without shaking at room temperature.

Unbound phage particles were washed away as follows;
after the $1^{st}$ panning round: 10×200 µl T-PBS, 5×200 µl T-PBS
after the $1^{st}$ panning round: 15×200 µl T-PBS, 10×200 µl T-PBS
after the $1^{st}$ panning round: 20×200 µl T-PBS, 20×200 µl T-PBS.

Elution of bound particles was performed by adding 200 µl per well of 0.1 M glycine, pH=2.2, and incubation with shaking for 30 min at room temperature. Subsequently, the phage suspension was neutralised by the addition of 60 µl 2M Tris-base, followed by the infection of E. coli TG1 cells by mixing 10 ml exponentially growing culture with 0.5 ml eluted phage and incubation for 30 min at 37°. Finally, infected bacteria were plated on TYE medium with 1% glucose and 100 µg/ml ampicillin, and incubated at 30° C. overnight.

Results of the Panning of the CH1-Phage Library on Rp10-L Peptide
Phage Titers

| Panning round | concentration Rp10-L | input (phage/ml) | output (phage/ml) |
|---|---|---|---|
| $1^{st}$ | 100 µg/ml | $5.6 \times 10^{13}$ | $1.6 \times 10^{10}$ |
| $2^{nd}$ | 100 µg/ml | $4.04 \times 10^{14}$ | $8.55 \times 10^{8}$ |
| $3^{rd}$ | 50 µg/ml | $3.53 \times 10^{14}$ | $1.19 \times 10^{12}$ |

Cloning of Selected Clones for Soluble Expression

Altered CH1 domain-encoding sequences, contained within eluted phage particles, were batch amplified with PCR. After restriction with NcoI and NotI, they were inserted in pNOTBAD (Invitrogen vector pBAD with subsequently inserted NotI site). After transformation into E. coli E104, the cells were selected on TYE medium with 1% glucose and 100 µg/ml ampicillin at 30° C.

Soluble expression of Selected Clones and Screening

4×96 ampicilline resistant colonies were cultured in 200 µl 2×YT medium with ampicillin in microtitre plates on a shaker overnight at 30° C. They were then induced with L-arabinose added to end concentration of 0.1%. After another overnight incubation, the cells were collected by centrifuging 15 min at 2000 rpm at room temperature and their periplasma proteins were released by resuspending in 100 µl Na-borate buffer (160 mM Na-borate, 200 mM NaCl, pH=8.0) and incubation for at least 6 hours.

For screening, 4 maleimide plates were coated with 100 µg/ml solution of 50 µg/ml peptide Rp10-L, dissolved in PBS, pH=7.2, overnight at 4° C. Plates were then blocked with 10 µg/ml cysteine-HCl in PBS, with 200 µl per well for 2 h at room temperature.

Released periplasmic protein was then allowed to react with the bound peptide by adding 50 µl lysate and 50 µl 2% BSA-PBS, followed by an overnight incubation at room temperature.

Binding of the his-tagged protein was revealed by 90-min-incubation with 100 µl per well solution of antibodies against tetra-his (QIAgen), diluted 1:1000 in 1% BSA-PBS, and a 90-min-incubation with 100 µl per well solution of goat anti-mouse antibodies, labelled with HRP (Sigma), diluted 1:1000 in 1% BSA-PBS. Signals were observed after the addition of substrate OPD (3 mg/ml) in Na-citrate/phosphate buffer, pH=4.5, and 0.4 µl/ml $H_2O_2$. The reaction was stopped with by adding 100 µl 1.25 M $H_2SO_4$.

Results of Screening for Binding of Rp10-L on a Single Well Per Clone

| | clone | | | | | | | |
|---|---|---|---|---|---|---|---|---|
| | A13 | A79 | A96 | B6 | B17 | B19 | B21 | B23 |
| A492/620 | 0.027 | 0.353 | 0.023 | 0.038 | 0.036 | 0.037 | 0.032 | 0.035 |

| | clone | | | | | | | |
|---|---|---|---|---|---|---|---|---|
| | C14 | C45 | C49 | C68 | C79 | C81 | D36 | D82 |
| A492/620 | 0.025 | 0.021 | 0.044 | 0.025 | 0.051 | 0.021 | 0.027 | 0.086 |

Background Reaction

| Plate | $A_{492/620}$ |
|---|---|
| A | 0.008 |
| B | 0.012 |
| C | 0.015 |
| D | 0.015 |

Clones revealing a positive signal were cultured in 20 ml 2×YT with, ampicillin, at 30° C. overnight. Then they were inoculated 1:20 into fresh medium, and after 3 h at 30° C. they were induced with end concentration of 0.1% L-arabinose, and allowed to express the recombinant CH1-domain overnight at 16° C. Periplasma of the expressing cells was then lysed in 1 ml of Na-borate buffer, pH-8.0, for a minimum of 6 h. Periplasmic extract was allowed to react with Rp10-L peptide and the binding was revealed exactly as described above.

Results of Screening for Binding of Rp10-L

| clone | + | − |
|---|---|---|
| A13 | −0.002 | −0.006 |
| A79 | 0.004 | 0.001 |
| A96 | 0.010 | 0.006 |
| B6 | 0.004 | 0.001 |
| B17 | 0.002 | 0.007 |
| B19 | −0.002 | 0.007 |
| B21 | 0.002 | 0.001 |
| B23 | 0.055 | 0.020 |
| C14 | 0.015 | 0.017 |
| C45 | 0.004 | 0.001 |
| C49 | 0.005 | −0.001 |
| C68 | 0.003 | 0.001 |
| C79 | 0.005 | 0.002 |
| C81 | 0.004 | 0.002 |
| D36 | 0.029 | 0.019 |
| D62 | 0.137 | 0.126 |

Cloning of Selected Clones for Soluble Expression in pET27b

Altered CH1 domain-encoding sequences, contained within clones that produced a significant signal on binding to Rp10-L, were amplified with PCR. After restriction with NcoI and NotI, they were inserted in pET27b (Novagen). After transformation into *E. coli* BL21 (DE3), transformed cells were selected on TYE medium with 1% glucose and 50 µg/ml kanamycin at 30° C.

Clones revealing a positive signal were cultured in 20 ml M9ZB medium with 2% glucose and kanamycin, at 30° C. overnight. Then they were inoculated 1:20 into fresh medium, and after 3 h at 30° C. they were induced with medium containing 1% glycerin instead of glucose, kanamycin and 1 mM IPTG, and allowed to express the recombinant CH1-domain overnight at 16° C. Periplasma of the expressing cells was then lysed in 1 ml of Na-borate buffer, pH=8.0, for a minimum of 6 h. Periplasmic extract was analysed for the presence of recombinant protein with western blotting and detection with anti tetra-his antibodies (QIAgen).

Sequence of CD20 Specific CH1 SMID, Clone C45

Analysis of Binding of CD-20, Expressed on Cells, Using FACS

Approximately $10^5$ Daudi cells were washed with PBS (800 rpm, 5 min, room temperature) and the recombinant CH3 domain in 1% BSA-PBS was allowed to bind for 2 h on ice. Cells were washed again with PBS and the allowed to react with 2 µg/ml anti penta His-Alexa fluor 488 antibody (QIAgen), diluted in 1% BSA-PBS, for 30 min on ice. After washing, the cells were analysed in FACS. Unlabelled cells, wild-type CH1 domain and cell line K562 were used as controls.

Example 8: Isolation of CL-Mutant Proteins Binding CD20 Antigen 3 panning rounds were performed. Maleimide activated plates (Pierce) were coated with a synthetic peptide, representing a mimotope of B-cell molecular marker CD20. 200 µl of the following solution were added per well: PBS, pH=7.2, with the following concentrations of dissolved peptide:

$1^{st}$ panning round: 100 µg/ml $2^{nd}$ panning round: 100 µg/ml $3^{rd}$ panning round: 50 µg/ml.

Incubation was overnight at 4° C., followed by blocking with 10 µg/ml cysteine-HCl in PBS, with 200 µl per well for 2 h at room temperature.

The surface display phage library, displaying mutated CL domain, was then allowed to react with the bound peptide by adding phage suspension and 2% BSA-PBS up to 200 µl, followed by incubation for 45 min with shaking and 90 min without shaking at room temperature.

Unbound phage particles were washed away as follows;

after the $1^{st}$ panning round: 10×200 µl T-PBS, 5×200 µl T-PBS after the $1^{st}$ panning round: 15×200 µl T-PBS, 10×200 µl T-PBS after the $1^{st}$ panning round: 20×200 µl T-PBS, 20×200 µl T-PBS.

Elution of bound particles was performed by adding 200 µl per well of 0.1 M glycine, pH=2.2, and incubation with shaking for 30 min at room temperature. Subsequently, the phage suspension was neutralised by the addition of 60 µl 2M Tris-base, followed by the infection of *E. coli* TG1 cells by mixing 10 ml exponentially growing culture with 0.5 ml eluted phage and incubation for 30 min at 37°. Finally, infected bacteria were plated on TYE medium with 1% glucose and 100 µg/ml ampicillin, and incubated at 30° C. overnight.

```
LOCUS C45 324 bp ds-DNA SYN 4-JUL-2006
   1 gcctccacca agggcccatc ggtcttcccc ctggcaccct cctccaagag cacctctggg 61 ggcacagcag ccctgggctg cctggtcaag gactacttcc ccgaaccggt gacggtgtcg 121 tggaactcag gcgccctgac cagcggcgtg cacaccttcc cggctgtcct gcagtcctca 181 ggactctact ccctcagcag cgtggtgacc gtggcccctc tgggtgttgg tgggcatctc 241 gtcctgcact acatctgcaa cgtgaatcac aagcccagca acaccaaggt ggacaagaaa 301 gttgagccca aatctgcggc cgct (SEQ ID NO: 14)
//

ENTRY C45
             5          10          15          20          25          30
   1 A S T K G P S V F P L A P S S K S T S G G T A A L G C L V K

31 D Y F P E P V T V S W N S G A L T S G V H T F P A V L Q S S

61 G L Y S L S S V V T V A P L G V G G H L V L H Y I C N V N H

91 K P S N T K V D K K V E P K S A A A (SEQ ID NO: 15)
```

Results of the Panning of the CL-Phage Library on Rp10-L Peptide

Phage Titers

| Panning round | concentration Rp10-L | input (phage/ml) | output (phage/ml) |
|---|---|---|---|
| $1^{st}$ | 100 μg/ml | $2.8 \times 10^{13}$ | $3.6 \times 10^{7}$ |
| $2^{nd}$ | 100 μg/ml | $4.29 \times 10^{14}$ | $6.88 \times 10^{9}$ |
| $3^{rd}$ | 50 μg/ml | $1 \times 10^{15}$ | $6.54 \times 10^{11}$ |

Cloning of Selected Clones for Soluble Expression

Altered CL domain-encoding sequences, contained within eluted phage particles, were batch amplified with PCR. After restriction with NcoI and NotI, they were inserted in pNOT-BAD (Invitrogen vector pBAD with subsequently inserted NotI site). After transformation into E. coli E104, the cells were selected on TYE medium with 1% glucose and 100 μg/ml ampicillin at 30° C.

Soluble Expression of Selected Clones and Screening

4×96 ampicilline resistant colonies were cultured in 200 μl 2×YT medium with ampicillin in microtitre plates on a shaker overnight at 30° C. They were then induced with L-arabinose added to end concentration of 0.1%. After another overnight incubation, the cells were collected by centrifuging 15 min at 2000 rpm at room temperature and their periplasma proteins were released by resuspending in 100 μl Na-borate buffer (160 mM Na-borate, 200 mM NaCl, pH=8.0) and incubation for at least 6 hours.

For screening, 4 maleimide plates were coated with 100 μg/ml solution of 50 μg/ml peptide Rp10-L, dissolved in PBS, pH=7.2, overnight at 4° C. Plates were then blocked with 10 μg/ml cysteine-HCl in PBS, with 200 μl per well for 2 h at room temperature.

Released periplasmic protein was then allowed to react with the bound peptide by adding 50 μl lysate and 50 μl 2% BSA-PBS, followed by an overnight incubation at room temperature.

Binding of the his-tagged protein was revealed by 90-min-incubation with 100 μl per well solution of antibodies against tetra-his (QIAgen), diluted 1:1000 in 1% BSA-PBS, and a 90-min-incubation with 100 μl per well solution of goat anti-mouse antibodies, labelled with HRP (Sigma), diluted 1:1000 in 1% BSA-PBS. Signals were observed after the addition of substrate OPD (3 mg/ml) in Na-citrate/phosphate buffer, pH=4.5, and 0.4 μl/ml $H_2O_2$. The reaction was stopped with by adding 100 μl 1.25 M $H_2SO_4$.

Results of Screening for Binding of Rp10-L on a Single Well Per Clone

| clone | | | | | | | |
|---|---|---|---|---|---|---|---|
| A2 | A51 | A57 | A64 | B21 | B23 | B44 | B92 |
| A492/620 0.048 | 0.083 | 0.035 | 0.032 | 0.037 | 0.036 | 0.041 | 0.154 |

| clone | | | | | | | |
|---|---|---|---|---|---|---|---|
| C18 | C19 | C28 | C56 | C76 | D2 | D51 | D82 |
| A492/620 0.153 | 0.033 | 0.042 | 0.062 | 0.030 | 0.016 | 0.033 | 0.046 |

Background Reaction

| Plate | $A_{492/620}$ |
|---|---|
| A | 0.016 |
| B | 0.016 |
| C | 0.012 |
| D | 0.014 |

Clones revealing a positive signal were cultured in 20 ml 2×YT with ampicillin, at 30° C. overnight. Then they were inoculated 1:20 into fresh medium, and after 3 h at 30° C. they were induced with end concentration of 0.1% L-arabinose, and allowed to express the recombinant CL-domain overnight at 16° C. Periplasma of the expressing cells was then lysed in 1 ml of Na-borate buffer, pH=8.0, for a minimum of 6 h. Periplasmic extract was allowed to react with Rp10-L peptide and the binding was revealed exactly as described above.

Results of Screening for Binding of Rp10-L

| clone | + | − |
|---|---|---|
| A2 | 0.002 | 0.001 |
| A57 | 0.006 | 0.004 |
| A62 | 0.016 | 0.005 |
| A64 | 0.006 | 0.006 |
| B21 | 0.005 | −0.002 |
| B23 | 0.004 | 0.004 |
| B44 | 0.007 | 0.002 |
| B92 | 0.038 | 0.017 |
| C18 | 0.025 | 0.041 |
| C19 | 0.006 | 0.003 |
| C28 | 0.010 | 0.003 |
| C56 | 0.026 | 0.010 |
| C76 | 0.075 | 0.034 |
| D2 | 0.003 | 0.002 |
| D82 | 0.007 | −0.007 |

Cloning of Selected Clones for Soluble Expression in pET27b

Altered CL domain-encoding sequences, contained within clones that produced a significant signal on binding to Rp10-L, were amplified with PCR. After restriction with NoeI and NotI, they were inserted in pET27b (Novagen). After transformation into E. coli BL21 (DE3), transformed cells were selected on TYE medium with 1% glucose and 50 μg/ml kanamycin at 30° C.

Clones revealing a positive signal were cultured in 20 ml M9ZB medium with 2% glucose and kanamycin, at 30° C. overnight. Then they were inoculated 1:20 into fresh medium, and after 3 h at 30° C. they were induced with medium containing 1% glycerin instead of glucose, kanamycin and 1 mM IPTG, and allowed to express the recombinant CL-domain overnight at 16° C. Periplasma of the expressing cells was then lysed in 1 ml of Na-borate buffer, pH=8.0, for a minimum of 6 h. Periplasmic extract was analysed for the presence of recombinant protein with western blotting and detection with anti tetra-his antibodies (QIAgen).

Example 9: Cloning, Expression and Characterisation of an Integrin-Binding Fcab

The potentially cyclic peptide CRGDCL (SEQ ID NO:19) was originally isolated by Koivunen et al 1993 (J. Biol. Chem. 1993 Sep. 25; 268(27):20205-10) from a 6-amino acid peptide library expressed on filamentous phage and was shown to inhibit the binding of RGD-expressing phage to α$_v$β$_1$ integrin or the attachment of α$_v$β$_1$-expressing cells to fibronectin. The peptide also inhibited cell attachment mediated by the α$_v$β$_1$, α$_v$β$_3$, and α$_v$β$_5$ integrins.

We have inserted the sequence GCRGDCL (SEQ ID NO:20) in the structural loop (the "EF" loop) of the CH3 domain of human IgG1. For that purpose, residues Asp92 and Lys 93 (IMGT numbering) were mutated to Gly and Leu respectively, and the 5 residues CRGDC were inserted between these mutated residues 92 and 93 to create the loop with the integrin-binding RGD motif, using standard cloning techniques. At the C-terminus of the insert, the sequence was fused in frame with the multiple cloning site of the vector so that the HSV-tag and the His-tag are attached C-terminally to the recombinant protein. The name of this recombinant protein Fcab-RGD4, or short RGD4. The DNA sequence coding for Fcab-RGD4 and the translation in amino acid sequence are shown below.

```
    +3    M   K   Y   L   L   P   T   A   A   A   G   L   L   L   L   A   A   Q   P   A
     1  ATGAAATACC TGCTGCCGAC CGCTGCTGCT GGTCTGCTGC TCCTCGCGGC CCAGCCGGCG
        TACTTTATGG ACGACGGCTG GCGACGACGA CCAGACGACG AGGAGCGCCG GGTCGGCCGC

+3    M   A   M   A   E   P   K   S   C   D   K   T   H   T   C   P   P   C   P   A
    61  ATGGCCATGC CGAGCCCAA ATCTTGTGAC AAAACTCACA CATGCCCACC GTGCCCAGCA
        TACCGGTACG GGCTCGGGTT TAGAACACTG TTTTGAGTGT GTACGGGTGG CACGGGTCGT

+3    P   E   L   L   G   G   P   S   V   F   L   F   P   P   K   P   K   D   T   L
   121  CCTGAACTCC TGGGGGGACC GTCAGTCTTC CTCTTCCCCC CAAAACCCAA GGACACCCTC
        GGACTTGAGG ACCCCCCTGG CAGTCAGAAG GAGAAGGGGG GTTTTGGGTT CCTGTGGGAG

+3    M   I   S   R   T   P   E   V   T   C   V   V   V   D   V   S   H   E   D   P
   181  ATGATCTCCC GGACCCCTGA GGTCACATGC GTGGTGGTGG ACGTGAGCCA CGAAGACCCT
        TACTAGAGGG CCTGGGGACT CCAGTGTACG CACCACCACC TGCACTCGGT GCTTCTGGGA

+3    E   V   K   F   N   W   Y   V   D   G   Y   E   V   H   N   A   K   T   K   P
   241  GAGGTCAAGT TCAACTGGTA CGTGGACGGC GTGGAGGTGC ATAATGCCAA GACAAAGCCG
        CTCCAGTTCA AGTTGACCAT GCACCTGCCG CACCTCCACG TATTACGGTT CTGTTTCGGC

+3    R   E   E   Q   Y   N   S   T   Y   R   V   V   S   V   L   T   V   L   H   Q
   301  CGGGAGGAGC AGTACAACAG CACGTACCGT GTGGTCAGCG TCCTCACCGT CCTGCACCAG
        GCCCTCCTCG TCATGTTGTC GTGCATGGCA CACCAGTCGC AGGAGTGGCA GGACGTGGTC

+3    D   W   L   N   G   K   E   Y   K   C   K   V   S   N   K   A   L   P   A   P
   361  GACTGGCTGA ATGGCAAGGA GTACAAGTGC AAGGTCTCCA ACAAAGCCCT CCCAGCCCCC
        CTGACCGACT TACCGTTCCT CATGTTCACG TTCCAGAGGT TGTTTCGGGA GGGTCGGGGG

+3    I   E   K   T   I   S   K   A   K   G   Q   P   R   E   P   Q   V   Y   T   L
   421  ATCGAGAAAA CCATCTCCAA AGCCAAAGGG CAGCCCCGAG AACCACAGGT GTACACCCTG
        TAGCTCTTTT GGTAGAGGTT TCGGTTTCCC GTCGGGGCTC TTGGTGTCCA CATGTGGGAC

+3    P   P   S   R   D   E   L   T   K   N   Q   V   S   L   T   C   L   V   K   G
   481  CCCCCATCCC GGGATGAGCT GACCAAGAAC CAGGTCAGCC TGACCTGCCT GGTCAAAGGC
        GGGGGTAGGG CCCTACTCGA CTGGTTCTTG GTCCAGTCGG ACTGGACGGA CCAGTTTCCG

+3    F   Y   P   S   D   I   A   V   E   W   E   S   N   G   Q   P   E   N   N   Y
   541  TTCTATCCCA GCGACATCGC CGTGGAGTGG GAGAGCAATG GGCAGCCGGA GAACAACTAC
        AAGATAGGGT CGCTGTAGCG GCACCTCACC CTCTCGTTAC CCGTCGGCCT CTTGTTGATG

+3    K   T   T   P   P   V   L   D   S   D   G   S   F   F   L   Y   S   K   L   T
   601  AAGACCACGC CTCCCGTGCT GGACTCCGAC GGCTCCTTCT TCCTCTACAG CAAGCTTACC
        TTCTGGTGCG GAGGGCACGA CCTGAGGCTG CCGAGGAAGA AGGAGATGTC GTTCGAATGG

+3    V   G   C   R   G   D   C   L   S   R   W   Q   Q   G   N   V   F   S   C   S
   661  GTGGGTTGCC GCGGTGATTG TCTGAGCAGG TGGCAGCAGG GGAACGTCTT CTCATGCTCC
        CACCCAACGG CGCCACTAAC AGACTCGTCC ACCGTCGTCC CCTTGCAGAA GAGTACGAGG

+3    V   M   H   E   A   L   H   N   H   Y   T   Q   K   S   L   S   L   S   P   G
   721  GTGATGCATG AGGCTCTGCA CAACCACTAC ACGCAGAAGA GCCTCTCCCT GTCTCCGGGT
        CACTACGTAC TCCGAGACGT GTTGGTGATG TGCGTCTTCT CGGAGAGGGA CAGAGGCCCA

+3    K   A   A   A   L   E   I   K   R   A   S   Q   P   E   L   A   P   E   D   P
   781  AAAGCGGCCG CACTCGAGAT CAAACGGGCT AGCCAGCCAG AACTCGCCCC GGAAGACCCC
        TTTCGCCGGC GTGAGCTCTA GTTTGCCCGA TCGGTCGGTC TTGAGCGGGG CCTTCTGGGG

+3    E   D   V   E   H   H   H   H   H   H                    SEQ ID NO: 16
   841  GAGGATGTCG AGCACCACCA CCACCACCAC                             SEQ ID NO: 17
        CTCCTACAGC TCGTGGTGGT GGTGGTGGTG                             SEQ ID NO: 18
```

The sequences encoding Fcab-RGD4 and Fcab-wt, respectively, were introduced into the mammalian expression vector pCEP4 by conventional cloning techniques. HEK 293 cells were transiently transfected with these expression plasmids and the Fcab containing culture medium harvested after 3 days and after one week. The Fcabs were purified via a Protein A column and acidic elution from the column, followed by immediate neutralisation. The Fcabs were dialysed against PBS and tested in an ELISA for binding to human $\alpha_v\beta_3$ integrin (Chemicon).

For the integrin ELISA, 1 ug/ml human $\alpha_v\beta_3$ integrin in PBS was coated over night on Maxisorp plates and blocked for 1 h with BSA in PBS containing 1 mM Ca2+. Fcab-RGD4 and Fcab-wt, respectively, were allowed to bind for 1 h in various dilutions starting from 10 µg/ml purified protein. Bound Fcabs were detected by HRP labelled protein A and TMB as a substrate. Binding of RGD4 to integrin (red line) resulted in significant signals from 10 µg/ml protein down to 0.16 µg/ml. As negative controls, RGD4 did not bind to the plate in the absence of integrin (grey line), nor did Fcab-wt bind to the integrin coated plate (green line). The binding of the commercial mouse anti human $\alpha_v\beta_3$ integrin mAb LM609 (Chemicon; blue line) served as a positive control.

TABLE

ELISA data demonstrating the binding of RGD4 and LM609 to human $\alpha_v\beta_3$ integrin. The various proteins were tested in concentrations as indicated in the first column resulting in the signals at 450 nm in the respective rows. Values for HEK produced and protein A purified Fcab-RGD4 binding to integrin are shown in the second column, Fcab-wt negative control in the third, and Fcab-RGD4 coating blank control in the fourth column. The values for binding of mouse anti $\alpha_v\beta_3$ integrin mAb LM609 are shown in the last column.

| protein concentration (µg/ml) | Fcab-RGD4 (OD 450) | Fcab-wt (OD 450) | coating BLK Fcab-RGD4 (OD 450) | LM609 (anti integrin mAb) (OD 450) |
| --- | --- | --- | --- | --- |
| 10 | 3.4513 | 0.0485 | 0.0152 | 0.6475 |
| 2.500 | 1.7446 | 0.0338 | 0.0127 | 0.6443 |
| 0.625 | 0.7068 | 0.0337 | 0.0125 | 0.6570 |
| 0.156 | 0.2384 | 0.0327 | 0.0123 | 0.6257 |
| 0.039 | 0.0829 | 0.0295 | 0.0127 | 0.3907 |
| 0.010 | 0.0388 | 0.0276 | 0.0103 | 0.1567 |
| 0.002 | 0.0303 | 0.0273 | 0.0112 | 0.0770 |

The invention claimed is:

1. A polypeptide comprising a scaffold comprising an immunoglobulin fold comprising a human IgG1 antibody CH3 constant domain, wherein
   (i) said antibody CH3 constant domain comprises at least six structural loops, said antibody CH3 constant domain comprising one structural loop region comprising up to 5 amino acid residue changes relative to the amino acid residues of the corresponding wild type IgG1 antibody CH3 constant domain, wherein said one structural loop region is selected from the group consisting of the A-B loop region and the E-F loop region; and
   (ii) said antibody CH3 domain comprises a solvent accessible surface comprising at least three of said residue changes at positions 17-19, or at positions 71-73 and 76-77 of SEQ ID NO: 21 or at least four of said residue changes at positions 71-73 and 76-77 of SEQ ID NO: 21;
   wherein said immunoglobulin fold comprises said loop regions defined in part (i) and (ii),
   wherein said up to 5 amino acid residue changes in said one structural loop region does not encompass incorporation of a peptide of predetermined amino acid sequence that binds an epitope independently of its insertion into said one structural loop region.

2. The polypeptide of claim 1, wherein at least two solvent accessible surfaces comprise said residue changes.

3. The polypeptide of claim 1, wherein said residue changes of (i) is a combination of an insertion and at least one substitution.

4. The polypeptide of claim 1, wherein said polypeptide comprises an antibody comprising an Fc domain, wherein said Fc domain comprises said scaffold.

5. A kit comprising the polypeptide of claim 1.

* * * * *